(12) United States Patent
Lee et al.

(10) Patent No.: US 10,035,791 B2
(45) Date of Patent: Jul. 31, 2018

(54) BICYCLIC COMPOUND AND PHARMACEUTICAL COMPOSITION THEREOF FOR TREATING STROKE AND USE THEREOF

(71) Applicant: China Medical University, Taichung (TW)

(72) Inventors: Kuo-Hsiung Lee, Kaohsiung (TW); Yu Zhao, Chapel Hill, NC (US); Sheng-Chu Kuo, Tainan (TW); Chung-Y. Hsu, Taichung (TW); Woei-Cherng Shyu, Taipei (TW); Yu-Chian Chen, Taichung (TW); Chen-Huan Lin, Taichung (TW); Wei Lee, Taipei (TW); Chun-Wei Chiang, Taichung (TW); Chang-Hai Tsai, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 15/287,725

(22) Filed: Oct. 6, 2016

(65) Prior Publication Data
US 2017/0298049 A1    Oct. 19, 2017

(30) Foreign Application Priority Data

Apr. 19, 2016  (TW) .............................. 105112170 A

(51) Int. Cl.
| | | |
|---|---|---|
| *C07D 221/02* | (2006.01) | |
| *C07D 407/12* | (2006.01) | |
| *C07D 311/94* | (2006.01) | |
| *C07D 221/04* | (2006.01) | |

(52) U.S. Cl.
CPC ......... *C07D 407/12* (2013.01); *C07D 221/04* (2013.01); *C07D 311/94* (2013.01)

(58) Field of Classification Search
CPC .................................................. C07D 407/12
USPC ....................................................... 546/112
See application file for complete search history.

(56) References Cited

U.S. PATENT DOCUMENTS 7,649,014 B2    1/2010  Zhang et al.
8,093,288 B2    1/2012  Zhang et al.

FOREIGN PATENT DOCUMENTS

CN         104523676 A        4/2015
WO     WO 2014155016      * 10/2014  ........... C07D 311/94

OTHER PUBLICATIONS

Hughes et al Brain Research, 2014 1543 308-304.*
Yujian et al. Journal of International Pharmaceutical Research, 2008, 35(5), 377-387.*
Liang et al. Chemistry Online, 2015, 78(3), 4-5.*
Marriott et al. Pharmaceutical Compounding and Dispensing Second Edition, Pharmaceutical Press, 2010.*
Djerassi et al. Journal of Organic Chemistry (1960), 25, 2174.*
Venkatesh et al., J. Pharm. Sci. 89, 145-54 (2000) (p. 146, left column).*
Dorwald F. A. Side Reactions in Organic Synthesis, 2005, Wiley: VCH, Weinheim p. IX of Preface p. 1-15.*
Yujian Lu et al., "Prodrugs: design and clinical applications", Journal of International Pharmaceutical Research, published in Oct. 2008, vol. 35 No. 5, pp. 377-387, published by Institute of Pharmacology & toxicology of Academy of Military Medical Sciences, Beijin, China.
Jing Liang et al., "Research Progress in Methods of Improving Blood Brain Barrier Permeability", Chemistry Online, published in 2015, vol. 78(3), pp. 4-5, Paragraph 2.2, published by Chinese Chemical Society, Beijin, China.
Rebecca H. Hughes et al., "Neuroprotection by genipin against reactive oxygen and reactive nitrogen species-mediated injury in organotypic hippocampal slice cultures", Brain Research, published on Jan. 16, 2014, vol. 1543, pp. 308-314, published by Elsevier B.V., Netherlands.

* cited by examiner

*Primary Examiner* — Nizal S Chandrakumar
(74) *Attorney, Agent, or Firm* — Richard Aron Osman

(57) ABSTRACT

The present disclosure relates to a bicyclic compound, a pharmaceutical composition thereof, and its novel use. More particularly, the present disclosure relates to the bicyclic compound according to Formula I or Formula II, the pharmaceutical composition for treating a stroke, and the use of the bicyclic compound treating the stroke.

20 Claims, 71 Drawing Sheets
(17 of 71 Drawing Sheet(s) Filed in Color)

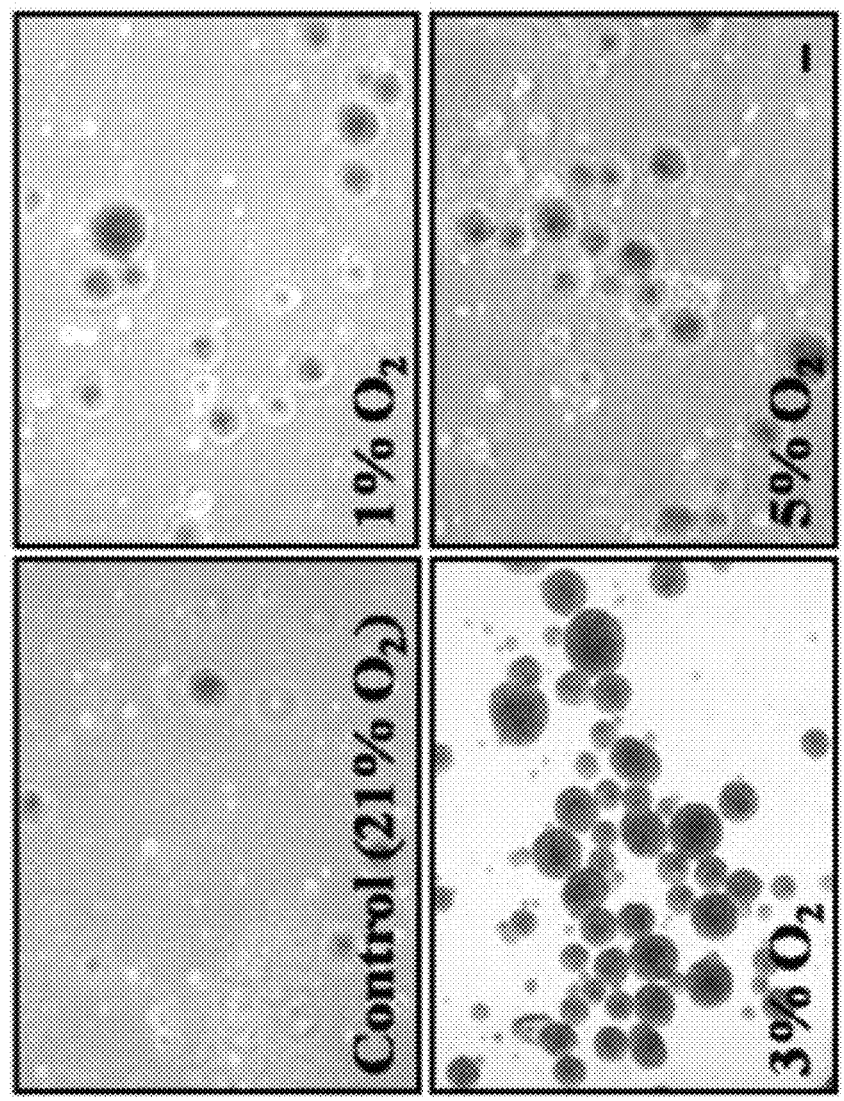

BICYCLIC COMPOUND AND PHARMACEUTICAL COMPOSITION THEREOF FOR TREATING STROKE AND USE THEREOF

RELATED APPLICATIONS

This application claims priority to Taiwan Application Serial Number 105112170, filed Apr. 19, 2016, which is herein incorporated by reference.

BACKGROUND

Technical Field

The present disclosure relates to a compound. More particularly, the present disclosure relates to a bicyclic compound and a pharmaceutical composition thereof.

Description of Related Art

A stroke ranks the third of ten leading causes of death in Taiwan. World Health Organization (WHO) also lists the stroke ranking the second of global leading causes of death. There are 5.8 million people died due to the stroke worldwide in 2005. It is expected to be 6.5 million people died due to the stroke worldwide in 2015. Population structure in Taiwan gradually becomes aging society, and the aging is an important risk factor for the stroke. According to a health care information in a local stroke center, a stroke risk in old people over 80 years old is 384 times higher than the stroke risk in young people under 30 years old.

The stroke, also known as a cerebrovascular accident (CVA), is a rapid development of a brain function loss caused by an abnormal blood supply to a brain. The stroke is due to a damage in a brain blood supply, so that local brain cells can not get enough nutrients and oxygen resulting in nerve function impairments. The stroke can be classified into two major categories: an ischemic stroke and a hemorrhagic stroke. In general, about 80% of the strokes are the ischemic strokes, and the rest being hemorrhagic strokes. The causes of hemorrhagic stroke and the ischemic stroke are different. The hemorrhagic stroke is caused by a blood vessel that breaks and bleeds into the brain, and the hemorrhagic stroke has a high mortality rate. The ischemic stroke is caused by a blood clot that blocks or plugs a blood vessel in the brain, and the ischemic stroke has a lower mortality rate compared to the hemorrhagic stroke. However, the ischemic stroke usually leads to neurobehavioral damages.

The only FDA (Food and Drug Administration) approved treatment for the ischemic stroke is tissue plasminogen activator (tPA) since 1996. The tPA works by dissolving the clot and improving blood flow to the part of the brain being deprived of blood flow, but the treatment of the tPA increases a probability of a cerebral hemorrhage by 10 times. In addition, physical disabilities of patients suffered from the ischemic stroke cause the problems in care-staffs and financial burdens at home and national health economic burdens. Therefore, a development of a drug for a stroke treatment to reduce a nerve cell damage caused by the ischemic stroke for enhancing a therapeutic effect on the ischemic stroke is in need.

SUMMARY

According to one aspect of the present disclosure, a bicyclic compound is provided. The bicyclic compound is represented by Formula I or Formula II:

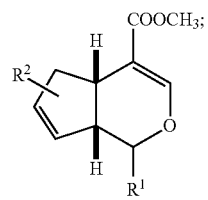

Formula I

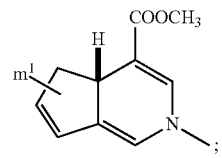

Formula II wherein in Formula I, $R^1$ is —OH, —OCH$_2$CH$_3$, =O, a substituent represented by Formula (i), a substituent represented by Formula (ii), a substituent represented by Formula (iii) or a substituent represented by Formula (iv), and $R^2$ is a monovalent group;

wherein in Formula II, $m^1$ is a substituent represented by Formula (v):

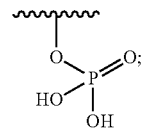

Formula (i)

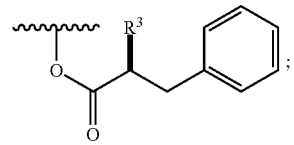

Formula (ii)

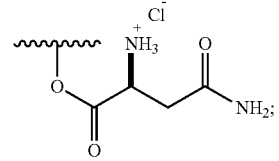

Formula (iii)

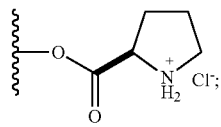

Formula (iv)

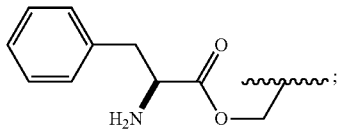

Formula (v)

wherein in Formula (ii), $R^3$ is —NH$_2$, —NH$_3^+$Cl$^-$ or substituent represented by Formula (vi):

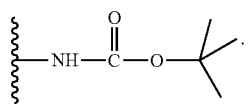

Formula (vi)

According to another aspect of the present disclosure, a pharmaceutical composition for treating a stroke is provided. The pharmaceutical composition includes an effective amount of the aforementioned bicyclic compound and a pharmaceutically acceptable carrier.

According to yet another aspect of the present disclosure, a method for treating the stroke is provided. The method includes administering the effective amount of the aforementioned bicyclic compound to a subject in need for a treatment of the stroke.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiments, with reference made to the accompanying drawings as follows:

FIG. 9B shows micrographs of neurosphere formations of the NSCs treated with the hypoxic treatment;

DETAILED DESCRIPTION

Figure 1A:
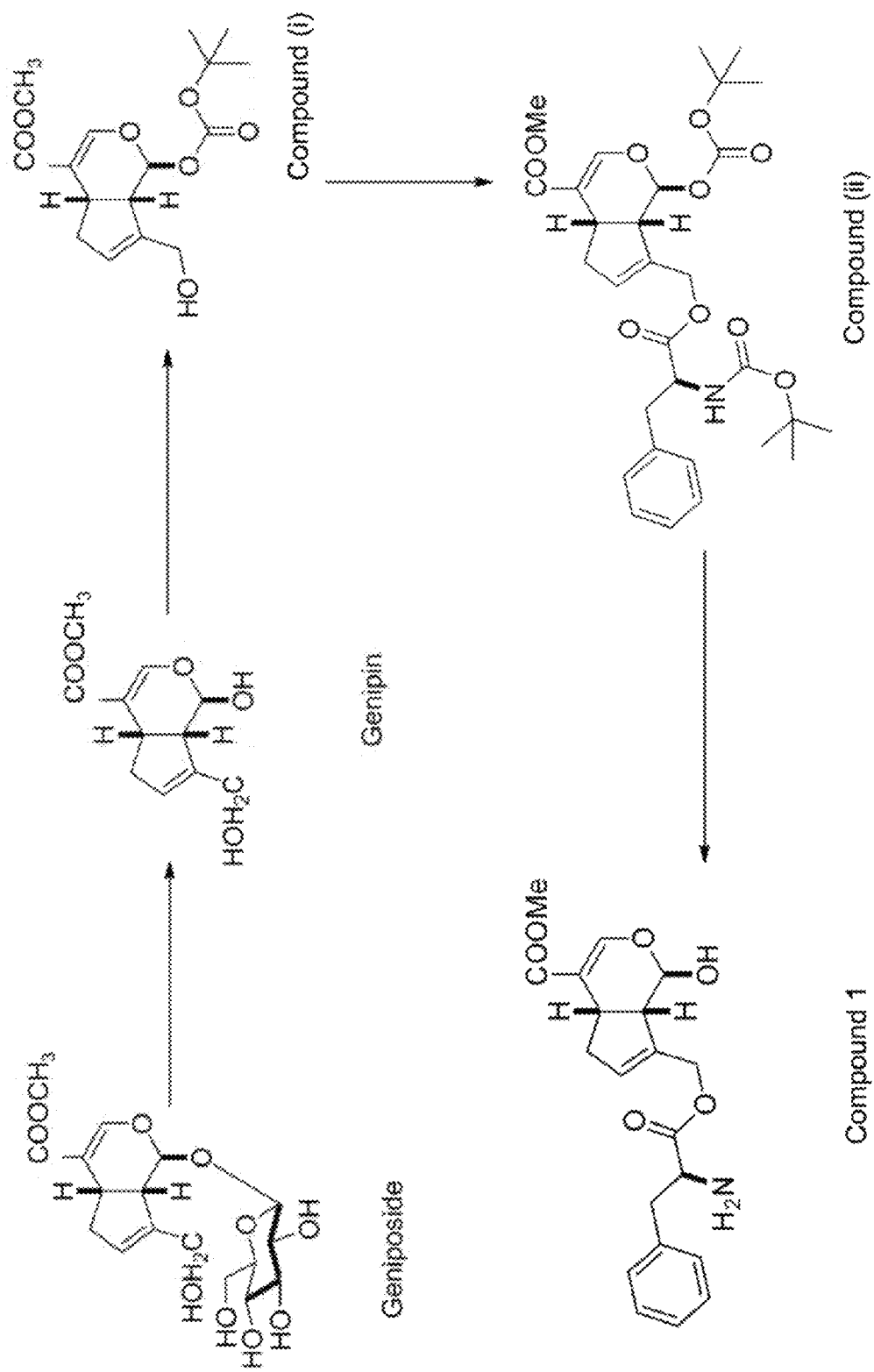
FIGS. 1A to 1E are flow charts showing a method for synthesizing bicyclic compounds according to one embodiment of the present disclosure.

A bicyclic compound, a pharmaceutical composition thereof and a novel use thereof are provided. First, the bicyclic compound of the present disclosure is identified by structural analysis. Then a nerve cell protecting effect of the bicyclic compound of the present disclosure is confirmed by in vitro cell assay. Next, a stroke treatment effect of the bicyclic compound of the present disclosure is verified by an ischemic stroke animal model. Further, the bicyclic compound of the present disclosure has the stroke treatment effect through HIF-1α-Bmi-1 pathway to stimulate a proliferation and a self-renew ability of neural stem cells (NSCs). In a brain of the ischemic stroke animal, an administration of the bicyclic compound of the present disclosure can promote a neural stem cell division and then move to a damaged area of the brain, thereby can reduce the damaged area of the brain and avoid a damage to brain tissue function. Therefore, the bicyclic compound of the present disclosure is a potentially therapeutic agent for treating a stroke.

The bicyclic compound is represented by Formula I or Formula II:

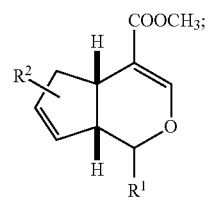

Formula I

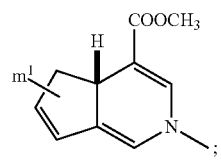

Formula II wherein in Formula I, R$^1$ is —OH, —OCH$_2$CH$_3$, =O, a substituent represented by Formula (i), a substituent represented by Formula (ii), a substituent represented by Formula (iii) or a substituent represented by Formula (iv), and R$^2$ is a monovalent group;

wherein in Formula II, $m^1$ is a substituent represented by Formula (v):

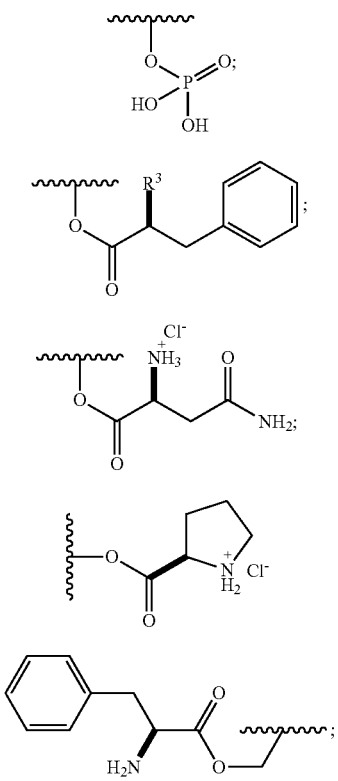

Formula (i)

Formula (ii)

Formula (iii)

Formula (iv)

Formula (v)

wherein in Formula (ii), $R^3$ is —$NH_2$, —$NH_3^+Cl^-$ or a substituent represented by Formula (vi):

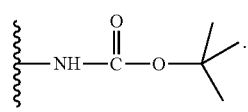

Formula (vi)

Further, the $R^2$ can be a substituent represented by Formula (vii):

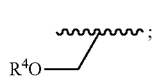

Formula (vii)

wherein the $R^4$ is —H, a substituent represented by Formula (viii), a substituent represented by Formula (ix) or a substituent represented by Formula (x):

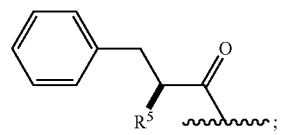

Formula (viii)

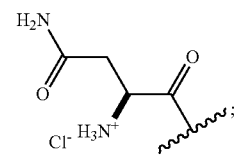

Formula (ix)

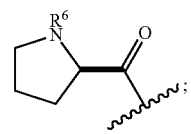

Formula (x)

wherein in Formula (viii), $R^5$ is —$NH_2$, —$NH_3^+Cl^-$ or the substituent represented by Formula (vi); and in Formula (x), $R^6$ is —$H_2^+Cl^-$ or the substituent represented by Formula (vi).

The following are descriptions of the specific terms used in the specification:

The term "Bmi-1 (B cell-specific MLV integration site-1)" is a protein encoded by the BMI1 gene. The BMI1 gene is a regulating gene of polycomb group (PcG) gene family. The Bmi-1 plays an important role in proliferation of stem cell, cellular self-renew and ageing.

The term "HIF-1α (hypoxia-inducible factor 1α)" is a member of hypoxia-inducible factors (HIFs), which is a transcription factor that respond to changes in available oxygen in the cellular environment, to be specific, to decreases in oxygen, or hypoxia.

Reference will now be made in detail to the present embodiments of the present disclosure, examples of which are illustrated in the accompanying drawings.

EXAMPLES

I. Synthesis and Identification of the Bicyclic Compound of the Present Disclosure The structural formula, molecular weight and chemical formula of a Compound 1 to a Compound 17 according to one embodiment of the present disclosure are shown in Table 1 as follows, wherein "Boc" is an abbreviation of "t-Butyloxy carbonyl" whose structural formula is represented by Formula (vi).

TABLE 1

| Compound | Structural formula | Molecular weight | Chemical formula |
|---|---|---|---|
| 1 | 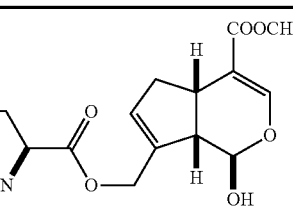 | 373 | $C_{20}H_{23}NO_6$ |

TABLE 1-continued

| Compound | Structural formula | Molecular weight | Chemical formula |
|---|---|---|---|
| 2 | | 720 | $C_{39}H_{48}N_2O_{11}$ |
| 3 | | 473 | $C_{25}H_{31}NO_8$ |
| 4 | | 560 | $C_{24}H_{31}Cl_2N_3O_8$ |
| 5 | | 560 | $C_{24}H_{31}Cl_2N_3O_8$ |
| 6 | | 453 | $C_{20}H_{24}NO_9P$ |
| 7 | | 670 | $C_{35}H_{46}N_2O_{11}$ |

TABLE 1-continued

| Compound | Structural formula | Molecular weight | Chemical formula |
|---|---|---|---|
| 8 | | 543 | $C_{25}H_{32}Cl_2N_2O_7$ |
| 9 | | 543 | $C_{25}H_{32}Cl_2N_2O_7$ |
| 10 | | 407 | $C_{20}H_{22}ClNO_6$ |
| 11 | | 401 | $C_{22}H_{27}NO_6$ |
| 12 | | 473 | $C_{25}H_{31}NO_8$ |
| 13 | | 368 | $C_{21}H_{24}N_2O_4$ |

TABLE 1-continued

| Compound | Structural formula | Molecular weight | Chemical formula |
|---|---|---|---|
| 14 | | 593 | $C_{29}H_{34}Cl_2N_2O_7$ |
| 15 | | 520 | $C_{29}H_{32}N_2O_7$ |
| 16 | | 409 | $C_{20}H_{24}ClNO_6$ |
| 17 | | 471 | $C_{25}H_{29}NO_8$ |

FIG. 1A is a flow chart showing a method for synthesizing the Compound 1 according to one embodiment of the present disclosure.

First, 1 g of a geniposide is dissolved in 30 mL of dichloromethane/H$_2$O (1:1) and treated with 100 mg of β-glucosidase. The reaction mixture is stirred violently at 37° C. for 24 hours. The mixture is extracted with dichloromethane 3 times. The organic layer is dried over Na$_2$SO$_4$ and removed in vacuo to yield 487 mg of genipin at 84% yield as white powder. Then 50 mg of genipin (0.22 mmol) is dissolved in dichloromethane, and 53 mg of di-tert-butyl dicarbonate (BOC$_2$O, 0.24 mmol) and 0.15 mL of triethylamine (Et$_3$N, 1.11 mmol) are added. The reaction is stirred for 3 hours. 1N of HCl is added, and the organic layer is separated, washed with brine, dried over Na$_2$SO$_4$ and concentrated. The residue is purified by column chromatography (10% EtOAc in Hexane) to produce 51 mg of a Compound (i) at 71% yield as colorless oil. To a solution of the Compound (i) (1 equiv) in dry dichloromethane is added 1.1 equiv of N-Boc-amino acid, 1.1 equiv of 1-Ethyl-3-(3-dimethylaminopropyl) (EDCl) and 0.1 equiv of 4-Dimethylaminopyridine (DMAP). The reaction is stirred at room temperature until the starting material is consumed. The solution is diluted with dichloromethane and washed 3 times with brine. The organic layer is dried over Na$_2$SO$_4$ and concentrated. The residue is chromatographed using gel column to yield a Compound (ii) at 99% yield. 1 equiv of the Compound (ii) is dissolved in 25 equiv of trifluoroacetic acid (TFA) and dichloromethane (CH$_2$Cl$_2$/TFA 10:1) respectively. The reaction is stirred for 2 hours. Then the mixture is concentrated to remove TFA. The residue is purified by column chromatography (5% of MeOH in CH$_2$Cl$_2$) to produce the Compound 1 at 87% yield.

The nuclear magnetic resonance (NMR) spectroscopy data of the Compound 1 analyzed by NMR spectrometers shown in the following: $^1$H NMR (400 MHz, CDCl$_3$): δ 7.39 (s, 1H), 7.31-7.20 (overlap, 5H), 5.90 (s, 1H), 4.85 (d, J=9.6 Hz, 1H), 4.78 (d, J=9.3 Hz, 1H), 4.25 (t, J=4.8 Hz, 1H), 3.72 (3H, s), 3.26 (m, 2H), 3.11 (dd, J=12.9, 6.6 Hz, 1H), 2.87 (m, 1H), 2.38 (t, J=6.0 Hz, 1H), 2.01 (m, 1H); ESI (m/z) 374.14 [M+H]$^+$.

Figure 1B:
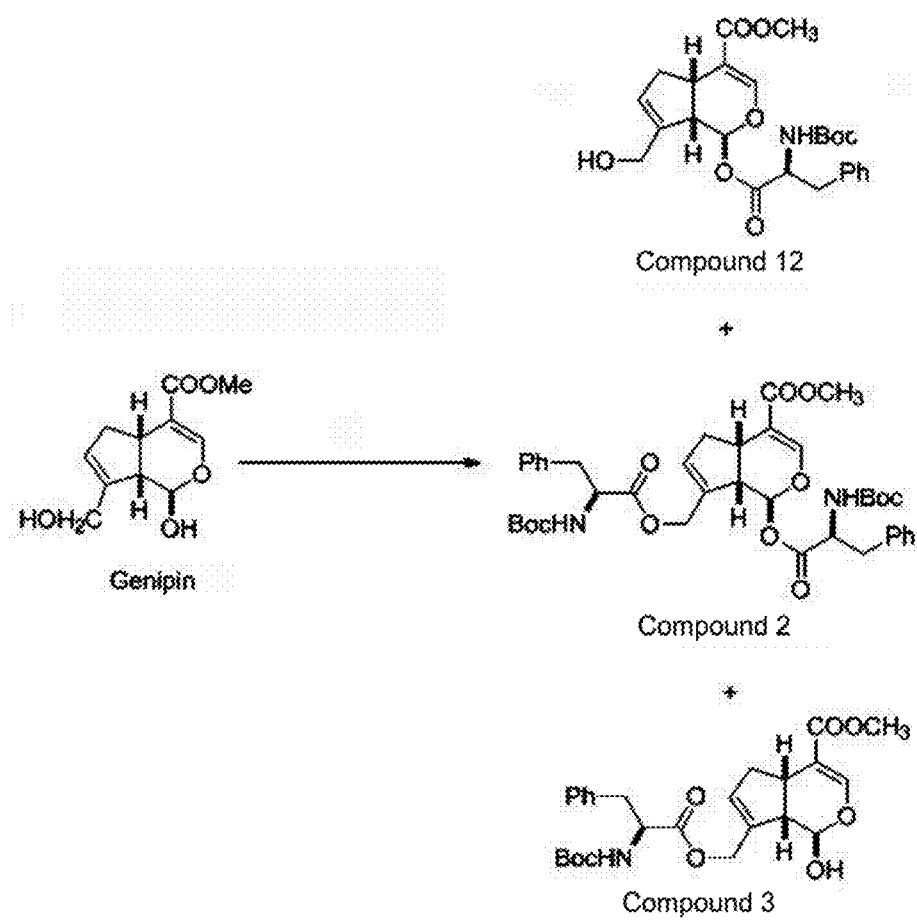

FIG. 1B is the flow chart showing the method for synthesizing a Compound 2, a Compound 3 and a Compound 12 according to one embodiment of the present disclosure.

To a solution of genipin (500 mg, 2.21 mmol) in dry dichloromethane are added 704 mg of Boc-L-phenylalanine (2.65 mmol), 636 mg of EDCl (3.32 mmol) and 26.9 mg of DMAP (0.22 mmol). The reaction is stirred at room temperature for 1 hour. The solution is then diluted with dichloromethane and washed 3 times with brine. The organic layer is dried over $Na_2SO_4$ and concentrated. The residue is chromatographed using gel column (20% EtOAc in Hexane) to yield 310.9 mg of the Compound 2 at 20% yield, 390.1 mg of the Compound 3 at 37% yield, and 223.8 mg of the Compound 12 at 21.4% yield.

The NMR spectroscopy data of the Compound 2 analyzed by NMR spectrometer is shown in the following: $^1$H NMR (400 MHz, $CDCl_3$): δ 7.42 (s, 1H), 7.31-7.14 (overlap, 10H), 5.96 (d, J=5.6 Hz, 1H), 5.84 (s, 1H), 4.75-4.57 (overlap, 4H), 3.74 (3H, s), 3.21-3.05 (overlap, 6H), 2.85 (dd, J=17, 8 Hz, 1H), 2.72 (m, 1H), 2.20 (m, 1H), 1.41 (s, 18H). ESI (m/z) 743.20 $[M+Na]^+$.

The NMR spectroscopy data of the Compound 3 analyzed by NMR spectrometer is shown in the following: $^1$H NMR (400 MHz, $CDCl_3$): δ 7.50 (s, 1H), 7.31-7.15 (overlap, 5H), 5.90 (s, 1H), 5.00 (d, J=7.6 Hz, 1H), 4.75-4.70 (overlap, 2H), 4.55 (d, J=6.4 HZ, 1H), 3.72 (3H, s), 3.16-3.11 (overlap, 3H), to 2.90 (m, 1H), 2.40 (m, 1H), 2.03 (m, 1H), 1.41 (s, 9H). ESI (m/z) 496.05 $[M+Na]^+$.

The NMR spectroscopy data of the Compound 12 analyzed by NMR spectrometer is shown in the following: $^1$H NMR (400 MHz, CDCl3): δ 7.45 (s, 1H), 7.33-7.18 (overlap, 5H), 6.08 (d, J=6.8 Hz, 1H), 5.85 (s, 1H), 4.59 (dd, J=14.2, 7.2 Hz, 1H), 4.20 (overlap, 2H), 3.75 (3H, s), 3.26 (dd, J=14.6, 7.2 Hz, 1H), 3.17-3.05 (overlap, 2H), 2.92-2.86 (overlap, 2H), 2.23 (m, 1H), 1.41 (s, 9H). ESI (m/z) 496.05 $[M+Na]^+$.

Figure 1C:
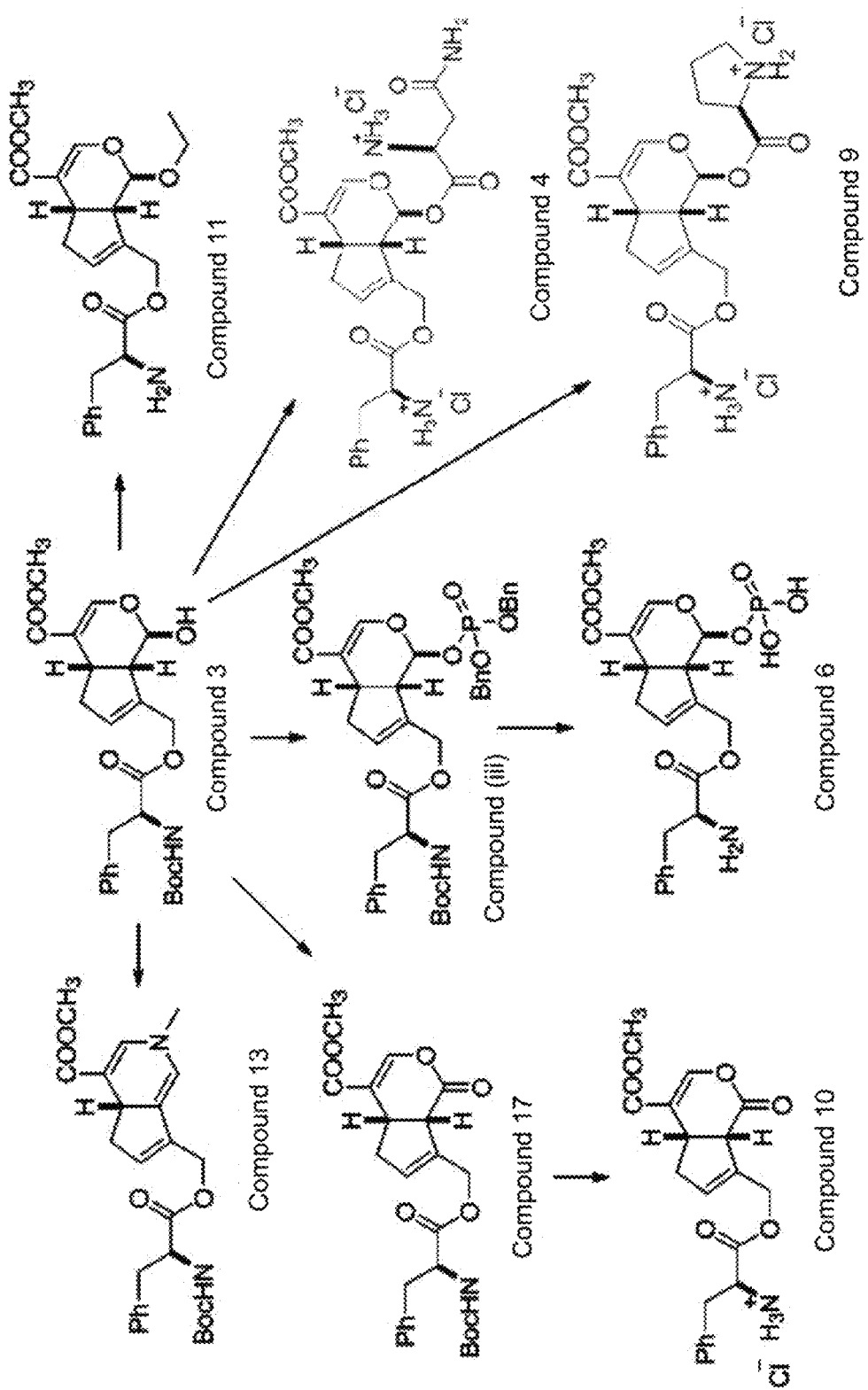

FIG. 1C is the flow chart showing the method for synthesizing a Compound 4, a Compound 6, a Compound 9, a Compound 10, a Compound 11, a Compound 13 and the Compound 17 according to one embodiment of the present disclosure.

456 mg of the Compound 3 (0.96 mmol) is dissolved in dry dichloromethane, and 268 mg of Boc-L-asparagine, 277 mg of EDCl (1.44 mmol) and 11.8 mg of DMAP (0.096 mmol) are added. The reaction is stirred at room temperature for 1 hour. The solution is diluted with dichloromethane and washed 3 times with brine. The organic layer is dried over $Na_2SO_4$ and concentrated. The residue is chromatographed using gel column (20% EtOAc its Hexane) to yield a Compound (iv) at 43% yield. The structural formula of Compound (iv) is shown in the following:

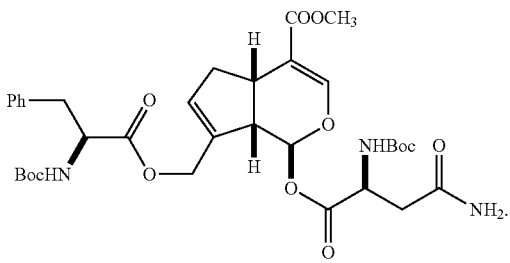

Compound (iv)

The NMR spectroscopy data of the Compound (iv) analyzed by NMR spectrometer is shown in the following: $^1$H NMR (400 MHz, $CDCl_3$): $^1$H NMR (400 MHz, CDCl3): δ 7.42 (s, 1H), 7.29-7.18 (overlap, 5H), 6.02-5.88 (overlap, 2H), 5.11 (d, J=7.6 Hz, 1H), 4.92 (d, J=12.4 Hz, 1H), 4.62-4.59 (overlap, 2H), 3.73 (3H, s), 3.22 (dd, J=13.8, 7.6 Hz, 1H), 3.12-2.97 (overlap, 4H), 2.88 (dd, J =16.6, 7.6 Hz, 1H), 2.76-2.72 (overlap, 2H), 1.45 (s, 9H), 1.39 (s, 9H). ESI (m/z) 710.10 $[M+Na]^+$.

0.12 mmol of the Compound (iv) is dissolved in 10 mL of HCl (2M in ether). The mixture is stirred at room temperature overnight. Then the solution is concentrated in vacuo and the resulted residue is triturated with 10 mL of ether and the crude product crashed out to yield the Compound 4 at 51% yield.

The NMR spectroscopy data of the Compound 4 analyzed by NMR spectrometer is shown in the following: $^1$H NMR (400 MHz, $CDCl_3$): δ 7.38-7.31 (overlap, 6H), 6.30 (s, 1H), 5.94 (s, 1H), 4.96 (d, J=9.6 Hz, 1H), 4.84 (m, 1H), 4.40 (br s, 2H), 3.73 (3H, s), 3.32-2.98 (overlap, 6H), 2.84 (d, J=14 Hz, 1H), 2.29 (d, J=16.4 Hz, 1H). ESI (m/z) 488.15 $[M+Na]^+$.

177 mg of the Compound 3 (0.37 mmol) is dissolved in 4 mL of dichloromethane. Then 0.34 mL of 85% N,N-diethyl dibenzylphosphoramidite (0.97 mmol) is dissolved in 1.1 mL of dichloromethane followed by addition of 1H-tetrazole (0.45 M in acetonitrile, 2.16 mL, 0.97 mmol). The mixture is stirred at room temperature for 1 hour. There it is cooled down to 0°, and 1.7 mL of 30% $H_2O_2$ is added. The mixture is stirred at 0° for 15 min. 4.5 mL of saturated $Na_2S_2O_3$ is added into the mixture, and it is then stirred at 0° C. for 2 hours. The mixture is extracted with 30 mL of EtOAc 3 times. The organic layer is washed with saturated $NaHCO_3$, brine NaCl, dried over $Na_2SO_4$, and concentrated under reduced pressure to give a residue which is subjected to chromatography on silica gel column (30% EtOAc in Hexane) to afford 218 mg of a Compound (iii) at 80% yield as colorless oil. A solution of the Compound (iii) (149 mg, 0.20 mmol) in 2.5 mL of dichloromethane is treated with a solution of trimethylsilyl bromide (TMSBr, 0.12 mL, 0.92 mmol) and 0.19 mL of pyridine (2.31 mmol) in 1.6 mL of dichloromethane at 0° C. for 4 to 6 hours. After the addition of 4.5 mL of $H_2O$, the aqueous layer is separated and lyophilized to give 58.3 mg of the Compound 6 at 63% yield as white powder.

The NMR spectroscopy data of the Compound 6 analyzed by NMR spectrometer is shown in the following: $^1$H NMR (400 MHz, $CDCl_3$): δ 7.50 (s, 1H), 7.40-7.29 (overlap, 5H), 5.97 (s, 1H), 5.43 (t, J=7.2 Hz, 1H), 4.82 (m, 2H), 4.38 (m, 1H), 3.73 (3H, s), 3.28-3.03 (overlap, 4H), 2.83 (m, 1H), 2.17 (m, 1H). ESI (m/z) 452.05 $[M-H]^-$.

To a solution of the Compound 3 (1 equiv) in dry dichloromethane is added 1.1 equiv of N-Boc-amino acid, 1.1 equiv of EDCl and 0.1 equiv of DMAP. The reaction is stirred at room temperature until the starting material is consumed. The solution is diluted with dichloromethane and washed 3 times with brine. The organic layer is dried over $Na_2SO_4$ and concentrated. The residue is chromatographed using gel column to yield pure compounds. The compounds are dissolved in 10 mL of HCl (2 M in ether). The mixture is stirred at room temperature overnight. Then the solution is concentrated in vacuo and the resulted residue is triturated with 10 mL of ether and the crude product crashed out. The resulting solid is washed with ether to afford the Compound 9 at 54% yield over two steps.

The NMR spectroscopy data of the Compound 9 analyzed by NMR spectrometer is shown in the following: $^1$H NMR (400 MHz, $CDCl_3$): δ 7.44 (s, 1H), 7.36-7.31 (overlap, 5H), 6.23 (d, J=3.6 Hz, 1H), 5.95 (s, 1H), 4.91-4.80 (overlap, 2H), 4.56 (d, J=6.8 Hz, 1H), 4.42 (d, J=5.2 Hz 1H), 3.73 (3H, s), 3.41 (br s, 2H), 3.31-3.27 (overlap, 3H), 3.05 (brs, 1H), 2.86 (m, 1H), 2.49 (m, 1H), 2.29-2.11 (overlap, 4H). ESI (m/z) 471.05 [M+H]⁺.

50 mg of the Compound 3 (0.097 mmol) is dissolved in 0.60 mL of TFA (7.76 mmol) and 25 mL of dichloromethane. The reaction is stirred for 2 hours. Then 12 mL of HCl (1.25 M in EtOH) is added. The mixture is stirred at room temperature overnight. Then the solution is concentrated, and the residue is reconstituted with dichloromethane and washed 3 times with brine. The organic layer is dried over Na$_2$SO$_4$ and concentrated. The crude product is chromatographed using gel column (20% EtOAc in Hexane) to yield 12.1 mg of the Compounds 11 at 29% yield as colorless oil.

The NMR spectroscopy data of the Compound 11 analyzed by NMR spectrometer is shown in the following: $^1$H NMR (400 MHz, CDCl$_3$): δ 7.52 (s, 1H), 7.30-7.19 (overlap, 5H), 5.82-5.75 (overlap, 2H), 4.74 (brs, 2H), 4.63 (q, J =7.6 HZ, 2H), 4.65 (d, J=5.6 Hz, 1H), 3.71 (3H, s), 3.12 (m, 1H), 3.05-2.92 (overlap, 5H), 2.81 (m, 1H), 2.58 (m, 1H), 2.15 (m, 1H). ESI (m/z) 402.15 [M+H]⁺.

A solution of Compound 3 (150 mg, 0.32 mmol) and 45 mg of p-toluenesulfonic acid in 10 mL of 40% aqueous methyl amine are stirred at room temperature for 48 hours. The solution is then extracted with 15 mL of to dichloromethane 3 times, and the organic layer is washed with brine, dried over Na$_2$SO$_4$ and concentrated. The residue is purified by preparative thin layer chromatography to yield 22.3 mg of the Compound 13 at 19% yield as colorless oil.

The NMR spectroscopy data of the Compound 13 analyzed by NMR spectrometer is shown in the following: $^1$H NMR (400 MHz, CDCl$_3$): δ 7.31-7.20 (overlap, 5H), 7.12 (s, 1H), 6.01 (s, 1H), 5.76 (brs, 1H), 4.37 (m, 2H), 4.21 (d, J =5.2 HZ, 1H), 3.67 (s, 3H), 3.41 (s, 3H), 3.25 (m, 1H), 3.17 (m, 1H), 3.13 (m, 1H), 2.81 (m, 1H), 2.28 (m, 1H), ESI (m/z) 391.10 [M+Na]⁺.

To a solution of the Compound 3 (301.2 mg, 0.92 mmol) in dichloromethane is added, 783.8 mg of Dess-Martin periodinane (1.845 mmol) and 155.3 mg of NaHCO$_3$ (1.85 mmol). The mixture is stirred until all starting material is consumed. The reaction mixture is treated with aqueous saturated NaS$_2$O$_3$ for 10 minutes, and extracted with dichloromethane 3 times. The organic layer is dried over anhydrous Na$_2$SO$_4$ and concentrated. The residue is purified by column chromatography (15% EtOAc in Hexane) to produce 244.2 mg of the Compound 17 at 82% yield as white powder.

The NMR spectroscopy data of the Compound 17 analyzed by NMR spectrometer is shown in the following: $^1$H NMR (400 MHz, CDCl$_3$): δ 7.49 (s, 1H), 7.29-7.15 (overlap, 5H), 5.88 (s, 1H), 4.97 (d, J=13.6 Hz, 1H), 4.89 (d, J=13.6 Hz, 1H), 4.59 (d, J=7.2 Hz, 1H), 3.79 (3H, s) 3.44 (m, 2H), 3.09-3.07 (overlap, 2H), 2.92 (m, 1H), 2.19 (m, 1H), 1.41 (s, 9H). ESI (m/z) 494.15 [M+Na]⁺.

0.12 mmol of the Compound 17 is dissolved in 10 mL of HCl (2 M in ether). The mixture is stirred at room temperature overnight. Then the solution is concentrated in vacuo and the resulted residue is triturated with 10 mL of ether and the crude product crashed out. The resulting solid is washed with ether to afford the Compound 10 at 84% yield.

The NMR spectroscopy data of the Compound 10 analyzed by NMR spectrometer is shown in the following: $^1$H NMR (400 MHz, CDCl$_3$): δ 7.56 (s, 1H), 7.37-7.25 (overlap, 5H), 5.95 (s, 1H), 5.04 (d, J=13.2 Hz, 1H), 4.96 (d, J=13.2 Hz, 1H), 4.39 (t, J=7.2 Hz, 1H), 3.78 (3H, s), 3.52 (m, 1H), 3.41 (m, 1H), 3.25-3.23 (overlap, 2H), 2.88 (dd, J=16.6, 8 Hz, 1H), 2.19 (dd, J=16.8, 8.4 Hz, 1H). ESI (m/z) 371.95 [M+H]⁺.

Figure 1D:
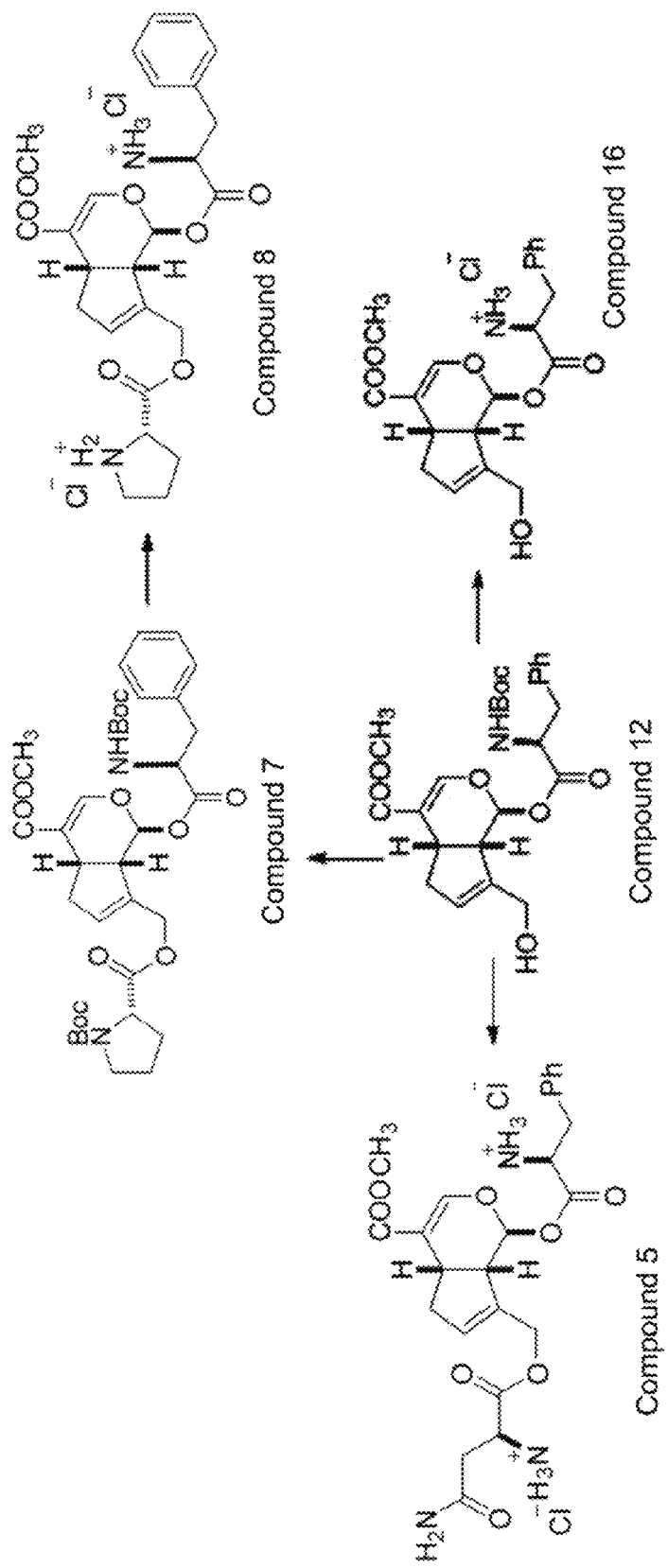

FIG. 1D is the flow chart showing the method for synthesizing a Compound 5, a Compound 7, a Compound 8 and a Compound 16 according to one embodiment of the present disclosure.

To a solution of Compound 12 (323.6 mg, 0.68 mmol) in dry dichloromethane are added 190 mg of Boc-L-phenylalanine (0.82 mmol), 197 mg of EDCl (1.03 mmol) and 8.4 mg of DMAP (0.068 mmol). The reaction is stirred at room temperature for 1 hour. The solution is then diluted with dichloromethane and washed 3 times with brine. The organic layer is dried over Na$_2$SO$_4$ and concentrated. The residue is chromatographed using gel column (20% EtOAc in Hexane) to yield 206.8 mg of the Compound (v) at 40% yield. The structural formula of Compound (v) is shown in the following:

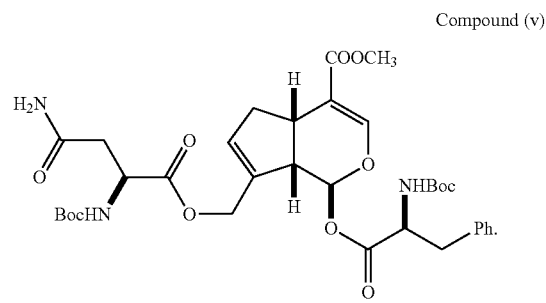 [SMILES: COC(=O)C1=CO[C@@H](OC(=O)[C@H](Cc2ccccc2)NC(=O)OC(C)(C)C)[C@@H]2C(COC(=O)[C@H](CC(N)=O)NC(=O)OC(C)(C)C)=CC[C@H]12]

Compound (v)

The NMR spectroscopy data of the Compound (v) analyzed by NMR spectrometer is shown in the following: $^1$H NMR (400 MHz, CDCl$_3$): δ 7.45-7.19 (overlap, 6H) 6.04 (s, 1H), 5.93 (s, 1H), 4.77-4.53 (overlap, 3H), 4.35 (m, 1H), 3.74 (3H, s), 3.28 (t, J=6.8 Hz, 1H), 3.10-2.73 (overlap, 6H), 2.21 (m, 1H), 1.44 (s, 9H), 1.40 (s, 9H). ESI (m/z) 701.4 [M+Na]⁺.

0.12 mmol of the Compound (v) is dissolved in 10 mL of HCl (2 M in ether). The mixture is stirred at room temperature overnight. Then the solution is concentrated in vacuo and the resulted residue is triturated with 10 mL of ether and the crude product crashed out. The resulting solid is washed with ether to afford the Compound 5 at 89% yield.

The NMR spectroscopy data of the Compound 5 analyzed by NMR spectrometer is shown in the following: $^1$H NMR (400 MHz, CDCl$_3$): δ 7.40-7.32 (overlap, 6H), 6.19 (s, 1H), 6.03 (s, 1H), 5.04 (m, 1H), 4.78 (m, 1H), 4.54 (m, 1H), 4.37 (m, 1H), 3.74 (3H, s), 3.28-3.79 (overlap 7H), 2.28 (m, 1H). ESI (m/z) 488.10 [M+H]⁺.

To a solution of the Compound 12 (1 equiv) in dry dichloromethane is added 1.1 equiv of N-Boc-amino acid, 1.1 equiv of EDCl and 0.1 equiv of DMAP. The reaction is stirred at room temperature until the starting material is consumed. The solution is diluted with dichloromethane and washed 3 times with brine. The organic layer is dried over Na$_2$SO$_4$ and concentrated. The residue is chromatographed using gel column to yield the Compound 7 at 77% yield as white powder.

The NMR spectroscopy data of the Compound 7 analyzed by NMR spectrometer is shown in the following: $^1$H NMR (400 MHz, CDCl$_3$): δ 7.42 (s, 1H), 7.31-7.16 (overlap, 5H), 6.05 (d, J=6 Hz, 1H), 5.92 (s, 1H), 4.70-4.62 (overlap, 2H), 4.34 (d, J=7.6 Hz, 1H) 4.25 (dd, J=4, 8.6 Hz, 1H), 3.74 (3H, s), 3,52-3.35 (overlap, 2H), 3.26 (dd, 14.4, 8 Hz, 1H), 3.17-3.04 (overlap, 2H), 2.92-2.84 (overlap, 2H), 2.27-2.17 (overlap, 2H), 1.99-1.85 (overlap, 3H), 1.41 (s, 9H), 1.39 (s, 9H). ESI (m/z) 693.20 [M+Na]⁺.

0.12 mmol of the Compound 7 is dissolved in 10 mL of HCl (2 M in ether). The mixture is stirred at room temperature overnight. Then the solution is concentrated in vacuo and the resulted residue is triturated with 10 mL of ether and the crude product crashed out. The resulting solid is washed with ether to afford the Compound 8 at 70% yield.

The NMR spectroscopy data of the Compound 8 analyzed by NMR spectrometer is shown in the following: $^1$H NMR (400 MHz, CDCl$_3$): δ 7.37-7.30 (overlap, 6H), 6.31 (s, 1H), 6.01 (s, 1H), 5.92 (s, 1H), 4.90-4.83 (overlap, 2H), 4.48 (br s, 2H), 3.75 (3H, s), 3.42 (br s, 2H), 3.31-3.20 (overlap, 3H), 2.83 (d, J =14 Hz, 1H), 2.48 (br s, 1H), 2.30 (d, J=15.6 Hz, 1H), 2.21-2.11 (overlap, 4H). ESI (m/z) 471.05 [M+H]$^+$.

0.12 mmol of the Compound 12 dissolved in 10 mL of HCl (2 M in ether). The mixture is stirred at room temperature overnight. Then the solution is concentrated in vacuo and the resulted residue is triturated with 10 mL of ether and the crude product crashed out. The resulting solid is washed with ether to afford the Compound 16 at 63% yield.

The NMR spectroscopy data of the Compound 16 analyzed by NMR spectrometer is shown in the following: $^1$H NMR (400 MHz, CDCl$_3$): δ 7.37-7.28 (overlap, 6H), 6.31 (d, J=5.2 Hz, 1H), 5.79 (s, 1H), 4.46 (t, J=6.8 Hz, 1H), 4.17 (d, J=14 Hz, 1H), 4.13 (d, J=13.6 Hz, 1H), 3.75 (3H, s), 3.21-3.13 (overlap, 3H), 3.06 (t, J=5.6 Hz, 1H), 2.81 (dd, 16.8, 7.6 Hz, 1H), 2.25 (t, J=16.8 Hz, 1H). ESI (m/z) 373.95 [M+H]$^+$.

Figure 1E:
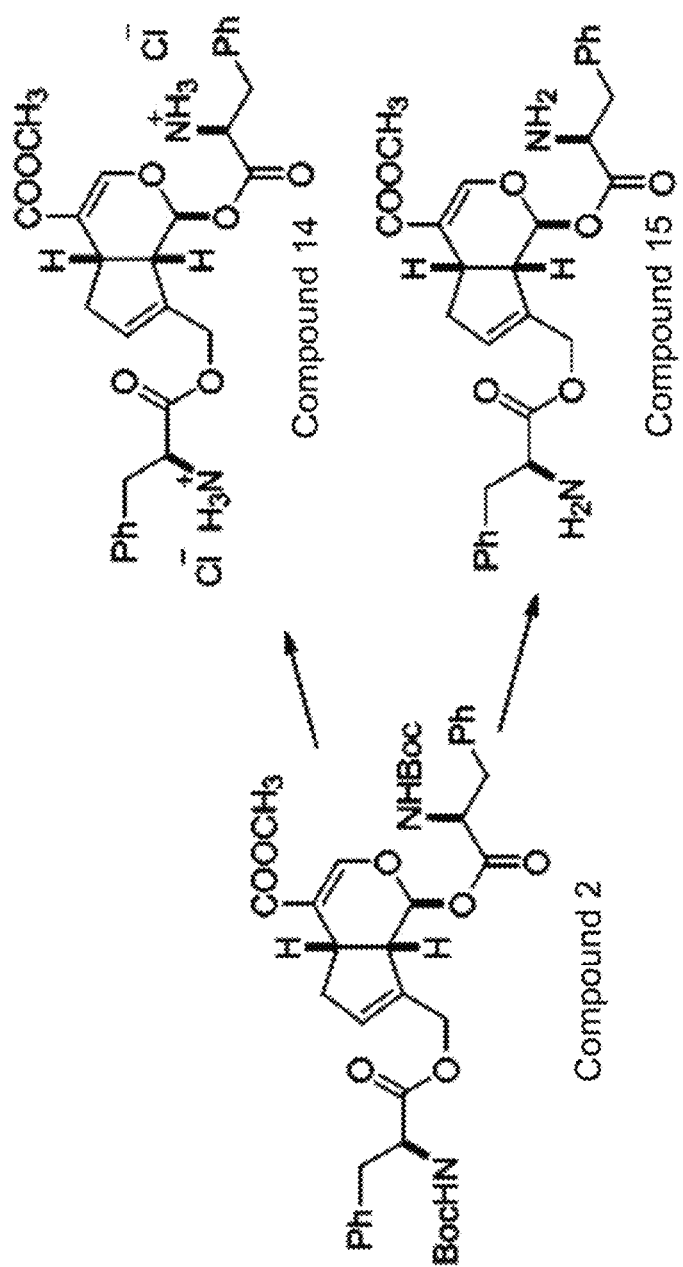

FIG. 1E is the flow chart showing the method for synthesizing a Compound 14 and a Compound 15 according to one embodiment of the present disclosure.

83.1 mg of the Compound 2 (0.12 mmol) is dissolved in 10 mL of HCl (2 M in ether). The mixture is stirred at room temperature overnight. Then the solution is concentrated in vacuo and the resulted residue is triturated with 10 mL of ether and the crude product crashed out. The resulting solid is washed with ether to afford 64.2 mg of the Compound 14 at 94% yield.

The NMR spectroscopy data of the Compound 14 analyzed by NMR spectrometer is shown in the following: $^1$H NMR (400 MHz, CDCl$_3$): δ 7.38-7.26 (overlap, 11H), 6.26 (d, J=4.8 Hz, 1H), 5.92 (s, 1H), 4.94 (d, J=13.2 Hz, 1H), 4.76 (d, J=13.2 Hz, 1H), 4.46 (t, J=6.8 Hz, 1H), 4.38 (t, J=6.4 Hz, 1H), 3.74 (3H, s), 3.28-3.12 (overlap, 5H), 2.95 (t, J=5.0 Hz, 1H), 2.80 (dd, J=17, 8 Hz, 1H), 2.27 (d, J=17.6 Hz, 1H). ESI (m/z) 521.10 [M+H]$^+$.

1 equiv of the Compound 2 is dissolved in 25 equiv of TFA and dichloromethane (CH$_2$Cl$_2$/TFA 10:1) respectively. The reaction is stirred for 2 hours. Then the mixture is concentrated to remove TFA. The residue is purified by column chromatography (5% of MeOH in CH$_2$Cl$_2$) to produce the Compound 15 at 92% yield as colorless oil.

The NMR spectroscopy data of the Compound 15 analyzed by NMR spectrometer is shown in the following: $^1$H NMR (400 MHz, CDCl$_3$): δ 7.27-7.14 (overlap, 11H), 5.90 (d, J=6.0 Hz, 1H), 5.77 (s, 1H), 4.60 (d, J=13.2 Hz, 1H), 4.52 (d, J=13.2 Hz, 1H), 4.34 (brs, 1H), 4.22 (brs, 1H), 3.74 (3H, s), 3.29-3.20 (overlap, 4H), 3.05 (dd, J=14, 7.2 Hz, 1H), 2.79 (dd, J=14, 7.2 Hz, 1H), 2.51 (m, 1H), 2.08 (m, 1H). ESI (m/z) 521.20 [M+H]$^+$.

II. The Nerve Cell Protecting Effect of the Bicyclic Compound of the Present Disclosure

2.1 A Lactate Dehydrogenase (LDH) Release Rate Analysis

H$_2$O$_2$ can cause an oxidative damage to cells and a destruction of the cell membrane, and consequently the LDH is released into medium. For that reason, the lower rate of the LDH released into the culture medium is represented the fewer damaged cells and better cell protection effect of sample.

Test cells are primary cortical cultures (PCCs) in this example. The PCCs are prepared from cerebral cortexes of gestation day 17 embryos from C57BL/6 mice as described previously (Cell Death Differ 2008; 15: 143-151). The PCCs are maintained under serum-free conditions in neurobasal medium (Invitrogen), supplemented with B-27 supplement (2%; invitrogen), glutamine (0.5 mM; Sigma Aldrich), glutamate (25 mM; Sigma Aldrich), penicillin (100 U/ml) and streptomycin (100 mg/ml; Invitrogen). At 4 days in vitro, half of the medium is removed and replaced with fresh medium without glutamate. The cultures are maintained in a humidified incubator at 37° C. with 5% CO$_2$. At 7 days in vitro, the PCCs are used for experimentation.

The PCCs are seeded in a 24-well plate and are allowed to stand for 20 minutes. Then 10$^{-4}$ mol/L of H$_2$O$_2$ (an inducer) or samples are added into the culture medium, wherein control group only is treated with H$_2$O$_2$ and test groups are simultaneously treated H$_2$O$_2$ and the sample, the Compound 1 to the Compound 17 at a concentration of 100 µM. The PCCs are maintained at 37° C. in a humidified atmosphere of 5% CO$_2$ for 24 hours. After incubation, the culture medium is collected and washed twice with phosphate buffered saline (PBS), and then are analyzed the LDH activity in the culture medium by using LDH Cytotoxicity Detection Kit (TaKaRa Bio Laboratories, Japan) to calculate the percentage cytotoxicity, which is represented the situation of cells damage, of the PCCs. The lower percentage cytotoxicity presents the lower LDH activity detected and less severe of cells damages, which indicates the better cell protection effect of the sample. The LDH activity is measured by a colorimetry. After a reaction between enzyme and particular substrate, an absorbance of the reaction solution and the LDH activity is linearly correlated. The LDH activity (U/10$^{-3}$ L) is calculated by a reduced optical density slope at a wavelength of 340 nm within three minutes. A lactate dehydrogenase activity unit is defined as a catalytic consumption of 1×10$^{-3}$ mol NADH per minute.

Figure 1F:
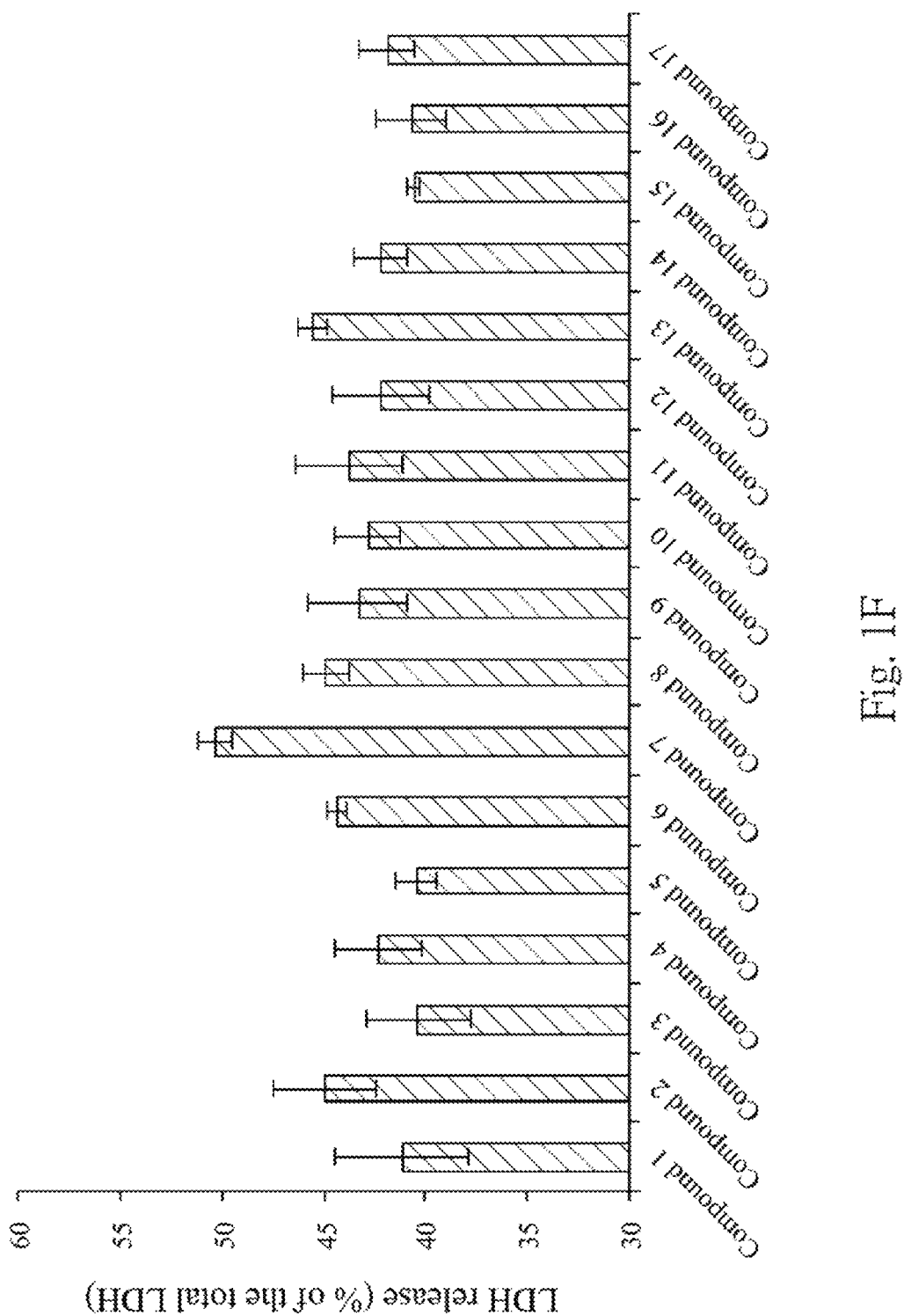
FIG. 1F shows analytical results of a lactate dehydrogenase (LDH) release rate analysis of the bicyclic compounds according to one embodiment of the present disclosure.

FIG. 1F shows the analytical results of the LDH release rate analysis of the bicyclic compounds according to one embodiment of the present disclosure. The bicyclic compounds analyzed in this example are the Compound 1 to the Compound 17. In FIG. 1F, all of the compounds can reduce the LDH release rate of the PCCs treated with H$_2$O$_2$ to below 55%. In addition, the compounds except the Compound 7 and the Compound 13 can decrease the LDH release rate of the PCCs treated with H$_2$O$_2$ to below 45%. The results show that the bicyclic compounds of the present disclosure have the effects on protecting the PCCs from the H$_2$O$_2$ induced oxidative damage.

Figure 1G:
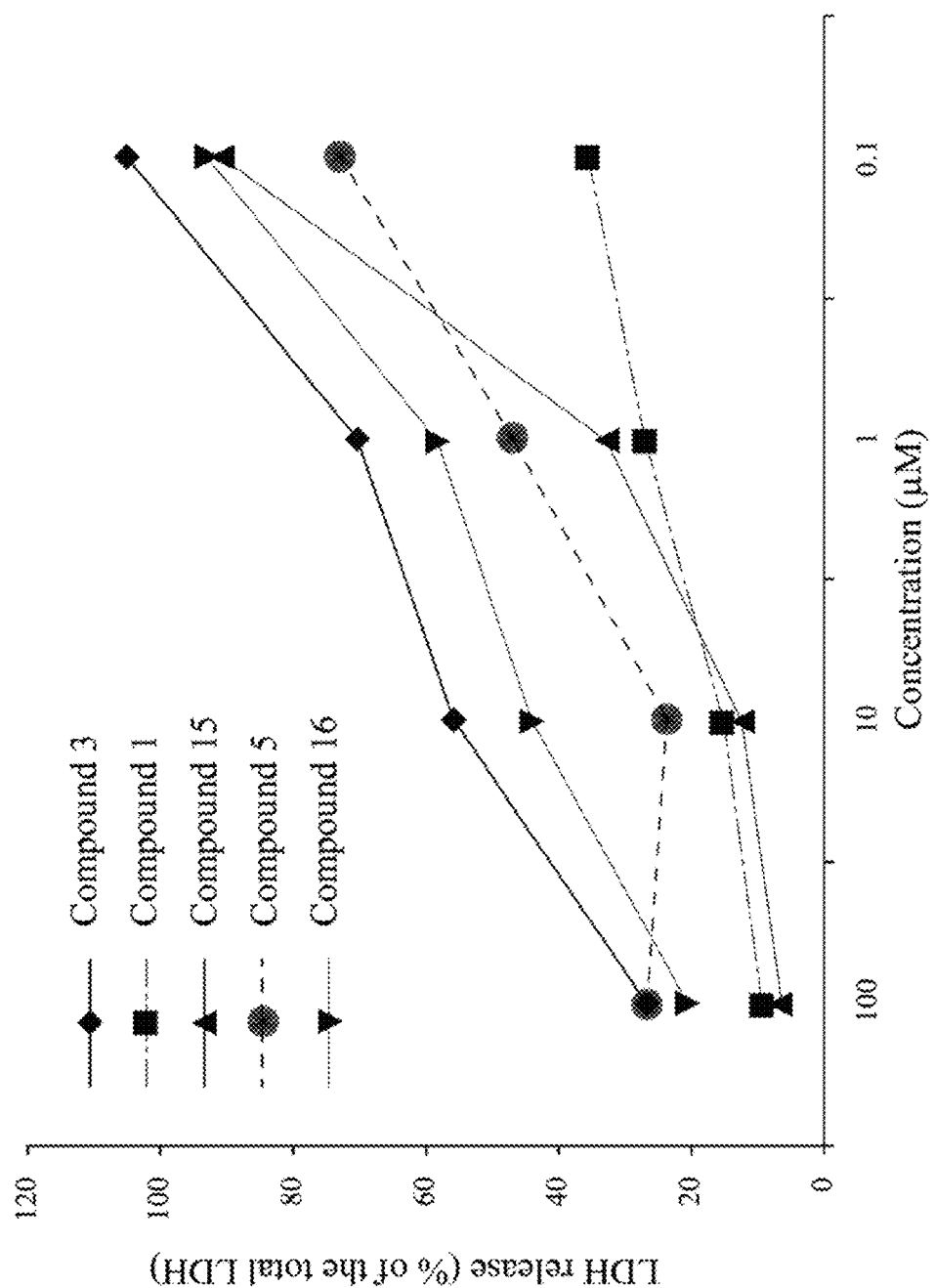
FIG. 1G shows the analytical results of the LDH release rate analysis of the bicyclic compounds at different concentrations according to one embodiment of the present disclosure.

FIG. 1G shows the analytical results of the LDH release rate analysis of the bicyclic compounds at different concentrations according to one embodiment of the present disclosure. The bicyclic compounds further analyzed an optimal concentration for protecting the PCCs in this example are the Compound 1, the Compound 3, the Compound 5, the Compound 15 and the Compound 16, which cause the lower LDH release rate in aforementioned example. The test concentrations of the bicyclic compounds are 0.1 µM, 1 µM, 10 µM and 100 µM, respectively. In FIG. 1G, the compound 1, the Compound 3 the Compound 15 and the Compound 16 reduce the LDH release rate of the PCCs most at the concentration of 100 µM. Substantially, the LDH release rate effect of the aforementioned bicyclic compound is reduced with decreasing concentration, thus the bicyclic compounds of the present disclosure protect the PCCs from the $H_2O_2$ induced oxidative damage in the dose-dependent manner. In addition, 0.1 μM of the Compound 1 can reduce the LDH release rate to of the PCCs treated with $H_2O_2$ to 30%. Therefore, the Compound 1 is used to estimate the effect of the bicyclic compounds of the present disclosure on the stroke treatment in subsequent ischemic stroke animal model.

III. A Regulation Mechanism of the Self-renewal and a Molecular Interaction of Neural Stem Cells After Ischemic Stroke The regulation mechanism of the self-renewal and the molecular interaction of the neural stem cells (NSCs) after the ischemic stroke are still not clarified. In previous study, the Bmi-1 is a key factor to promote the self-renewal and the proliferation of stem cells. Thus the examples in this part first discuss how the NSCs self-renew and proliferate through an activation of the Bmi-1.

3.1 A Cerebral Ischemia Increased Bmi-1 Expressions in a Rat Brain

In order to determine whether the cerebral ischemia increases the level of the Bmi-1, the Bmi-1 expressions are measured by analysis of a Bmi-1-immunoreactivity (Bmi-1-IR) and a Western blot analysis in the brains of ischemic rats.

The ischemic rats are induced by an ischemia-reperfusion model to simulate transient focal cerebral ischemia in rats. Test animals are male Sprague-Dawley (SD) rats weighing 250-300 g. The rats are anesthetized with chloral hydrate (0.4 g/kg IP) and subjected to cerebral ischemia. The ischemia-reperfusion model is induced by ligations of bilateral common carotid arteries (CCAs) and a right middle cerebral artery (MCA). The bilateral CCAs are clamped with non-traumatic arterial clips, and the right MCA is ligated with an 10-0 nylon suture. After 90 minutes ischemia, the suture on the MCA and the arterial clips on CCAs are removed to allow reperfusion. Core body temperature is monitored with a thermistor probe (Hewlett-Packard Model 21090A probe, Hewlett-Packard Company, Andover, Mass.), and maintained at 37° C. with a heating pad during anesthesia. After recovery from anesthesia, rat body temperature is maintained at 37° C. with a heat lamp.

Figure 2A:
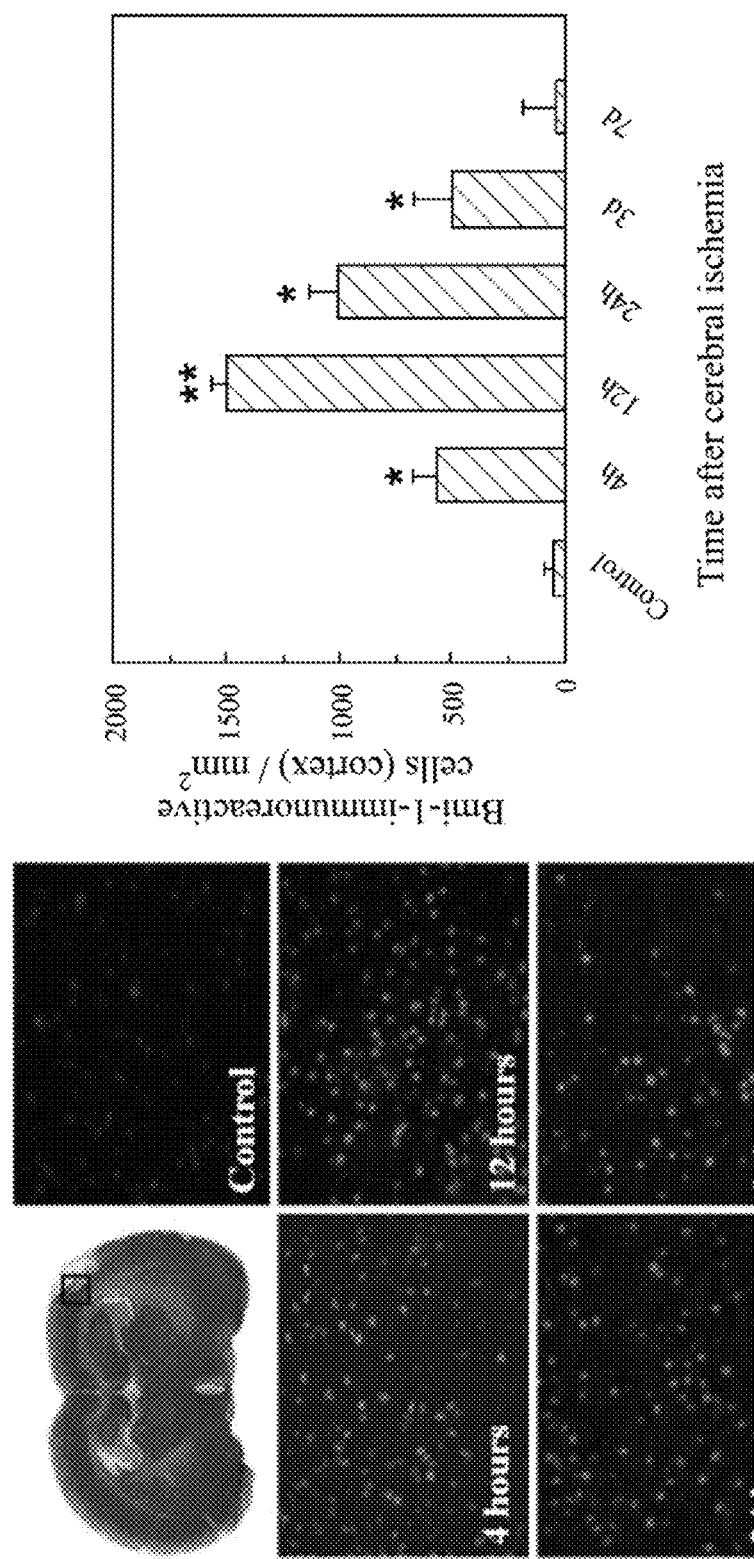
FIG. 2A shows the analytical results of Bmi-1 expressions in cortexes of brains of ischemic rats.
Figure 2B:
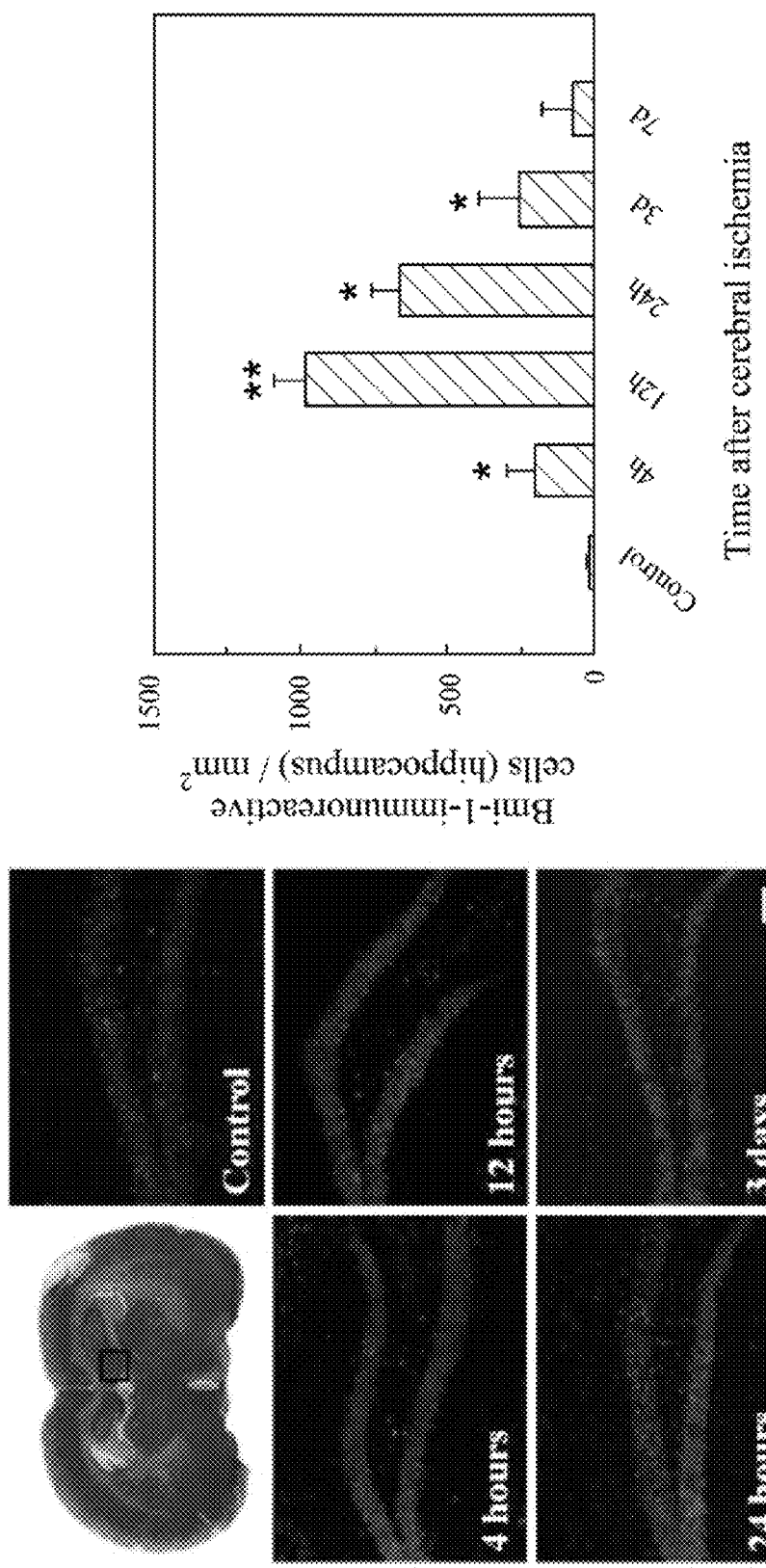
FIG. 2B shows the analytical results of Bmi-1 expressions in hippocampi of the brains of the ischemic rats.

The ischemic rats are re-anesthetized with chloral hydrate (0.4 g/kg IP), and are decapitated at 4 hours, 12 hours, 3 days, and 7 days after the cerebral ischemia. Three rats without MCA ligation are used as normal controls. The rat brains are performed a double immunofluorescence to label the Bmi-1. FIG. 2A shows the analytical results of the Bmi-1 expressions in cortexes of the brains of the ischemic rats. FIG. 2B shows the analytical results of the Bmi-1 expressions in hippocampi of the brains of the ischemic rats. Left figure of FIG. 2A shows micrographs of the cortexes of the brains of the ischemic rats, wherein square-mark represents an observed and photographed area. Right figure of FIG. 2A shows statistical results of a number of Bmi-1$^+$ cells in the cortexes of the brains of the ischemic rats. Left figure of FIG. 2B shows the micrographs of the hippocampi of the brains of the ischemic rats, wherein square-mark represents the observed and photographed area. Right figure of FIG. 2B shows the statistical results of the number of Bmi-1$^+$ cells in the hippocampi of the brains of the ischemic rats. In FIGS. 2A and 2B, greater numbers of Bmi-1$^+$ cells are detected in the ischemic rats, mainly in an ipsilateral cortex near an infarct boundary and a dentate gyrus (DG) of the hippocampus of rat brains after ischemia than in non-ischemic rat brains. The increase in the Bmi-1 immunoreactivity is time-dependent and reached its peak level 12 hours after the cerebral ischemia in the brains of the ischemic rats in comparison with the non-ischemic rats.

Figure 2C:
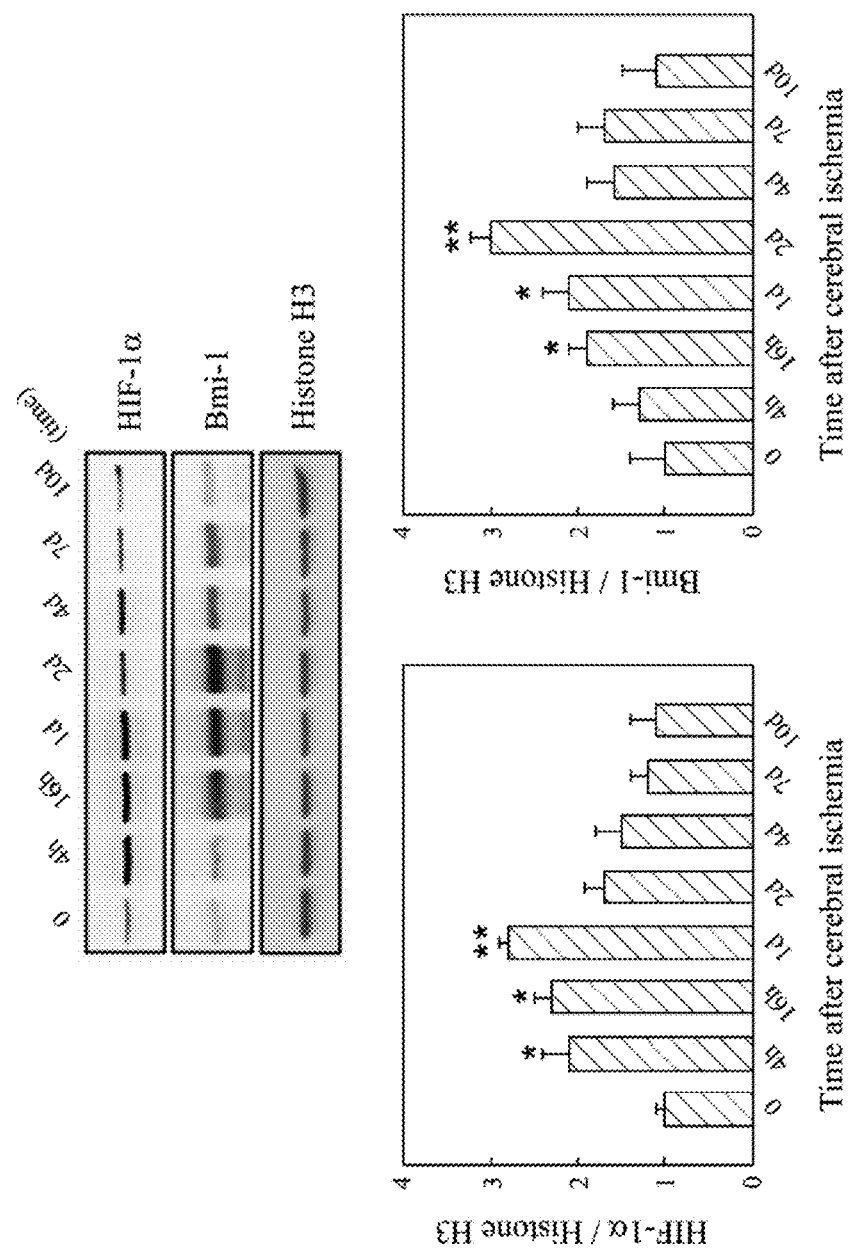
FIG. 2C shows the analytical results of the Bmi-1 expressions and HIF-1α expressions in the brains of the ischemic rats.

The Bmi-1 expressions and the HIF-1α expressions are further detected by the Western blot analysis in this example. The ischemic rats are decapitated at 4 hours, 12 hours, 3 days, and 7 days after reperfusion with 90 minutes MCA ligation. Total proteins of brain samples of the ischemic rats are extracted, and the protein expressions are detected by the Western blot analysis. The brain samples (cortical region and striatum) from homologous areas of rats without MCA ligation are used as normal controls. FIG. 2C shows the analytical results of the Bmi-1 expressions and the HIF-1α expressions in the brains of the ischemic rats. In FIG. 2C, the cerebral ischemia in the rat brains caused an increase in the Bmi-1 expressions and the HIF-1α expressions in the time-dependent manner, which is in agreement with the results of FIGS. 2A and 2B. It indicates that the cerebral ischemia increases the Bmi-1 expressions in the brain of the ischemic rats.

3.2 Immunoreactivity of the Bmi-1 Co-localized to Neuro-glial Cells After the Cerebral Ischemia In order to identify which cerebral cells expressed the Bmi-1 after the cerebral ischemia, double immunofluorescence is performed on brain specimens of the ischemic rats with a laser scanning confocal microscopy to confirm the immunoreactivity of the Bmi-1 co-localized to neuro-glial cells. DAPI (4',6-diamidino-2-phenylindole) is used to label nuclei. The specific nerve cell markers used are GFAP (glial fibrillary acidic protein), MAP-2 (microtubule-associated protein 2), NeuN (neuronal nuclear antigen) and Nestin (neuroectodermal stem cell marker), wherein GFAP is an astrocyte marker, MAP-2 is a neuron-specific cytoskeletal protein, NeuN is a nerve nucleus marker, and Nestin is a neural stem cell marker.

Figure 3:
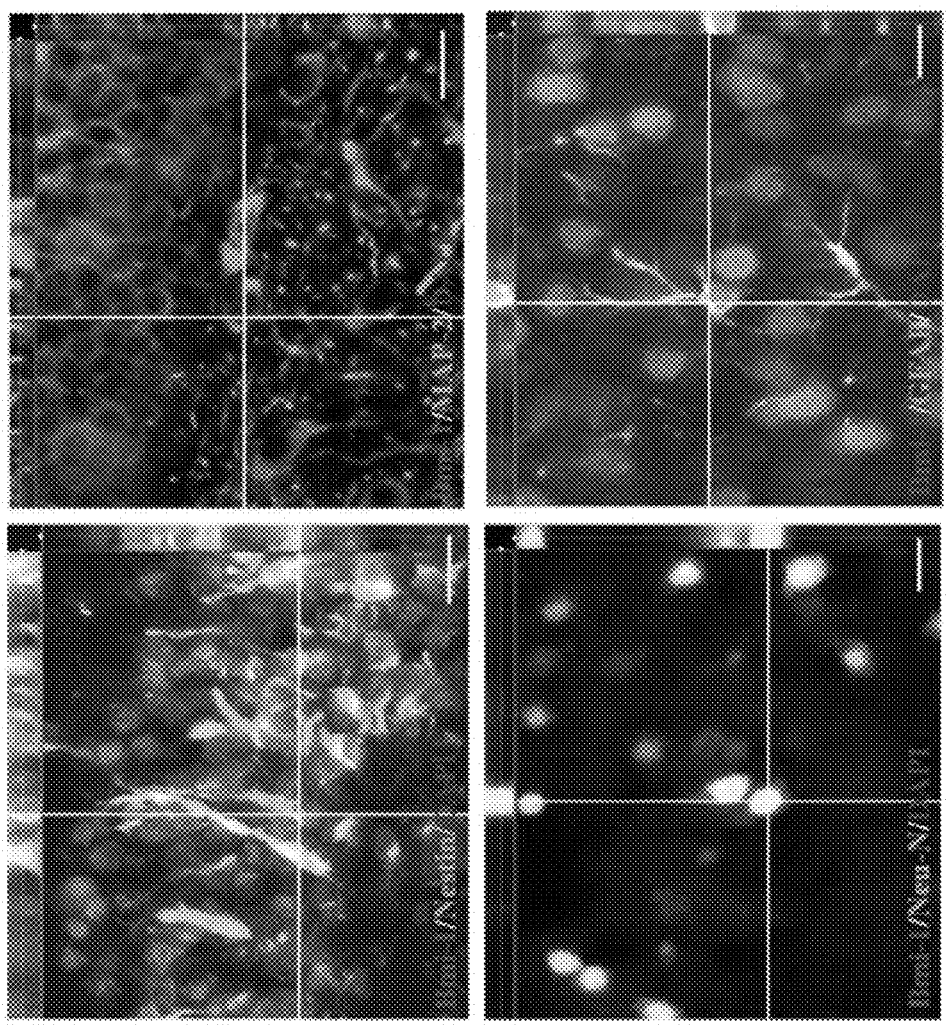
FIG. 3 are micrographs showing a co-localization of the Bmi-1 and nerve cell markers in brain tissues of the ischemic rats.

FIG. 3 are micrographs showing d co-localization of the Bmi-1 and the nerve cell markers in brain tissues of the ischemic rats, wherein a scales bar represents 50 μm. In FIG. 3, ischemic cortical areas or the DG of the ischemic rats reveal many Bmi-1$^+$ cells co-expressing markers for the NSCs (nestin$^+$), mature neurons (MAP-2$^+$ and Neu-N$^+$), and glia cells (GFAP$^+$).

3.3 Hypoxia Enhanced the Bmi-1 Expressions in the PCCs

In order to examine the effect of the hypoxia on the Bmi-1 expressions in the PCCs, the PCCs undergo a hypoxic treatment for various lengths of time (1 hour, 4 hours, 8 hours, 16 hours and 24 hours) and different $O_2$ levels (21%, 1%, 3% and 5%), wherein the PCCs treated with 21% $O_2$ is the normal control. After the hypoxic treatment, the PCCs are examined for the Bmi-1 expressions by the Bmi-1-IR and the Western blot analysis.

Figure 4A:
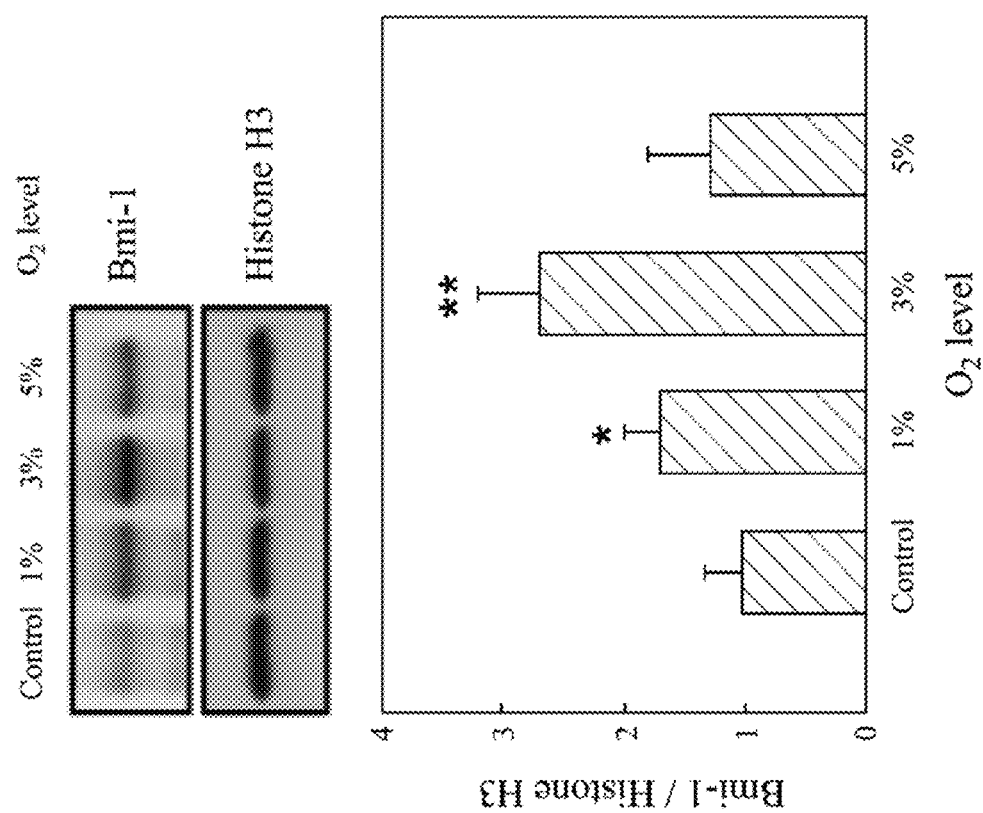
FIG. 4A shows the analytical results of the Bmi-1 expression in primary cortical cultures (PCCs) which are treated with a hypoxic treatment using different $O_2$ levels.
Figure 4B:
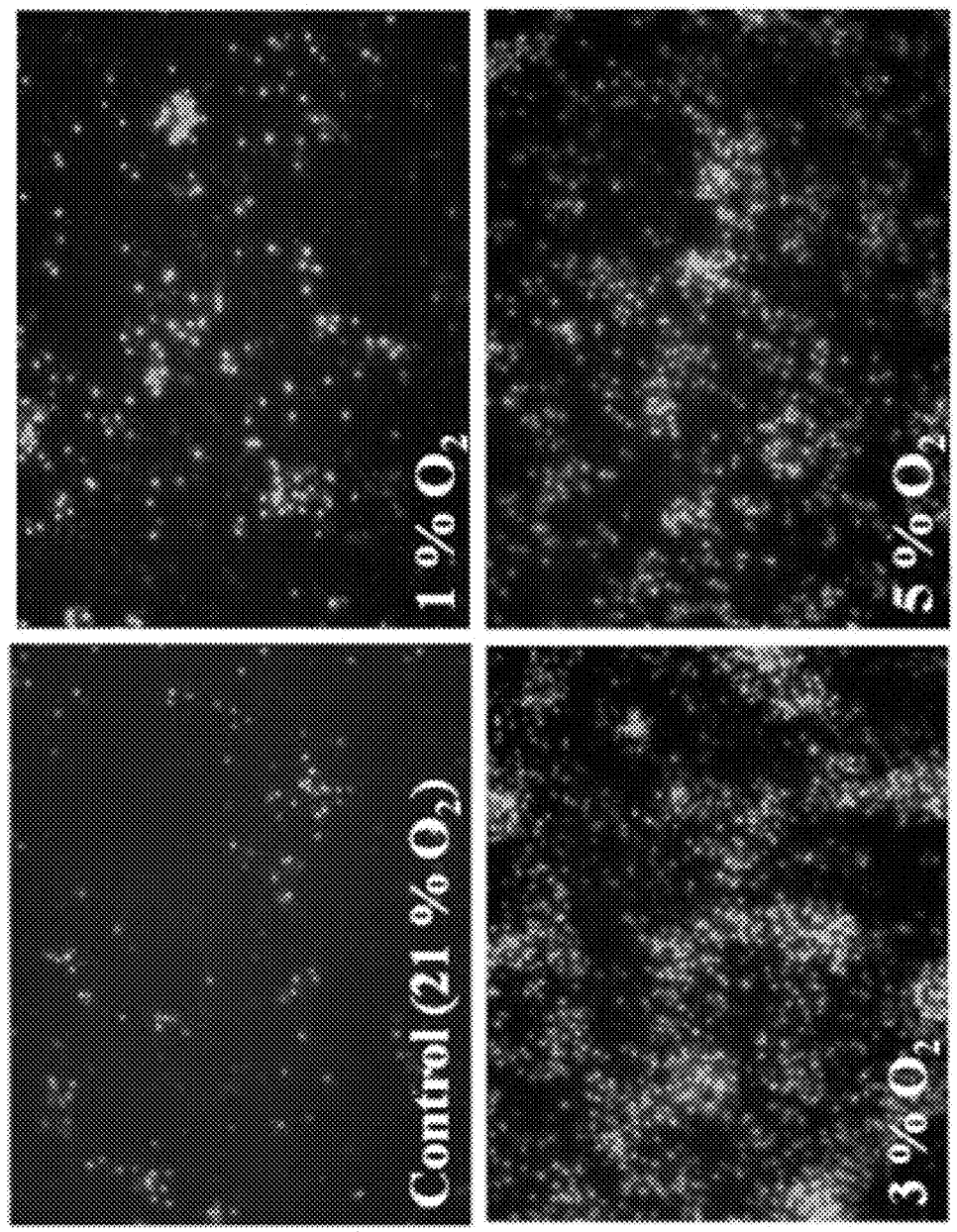
FIG. 4B are micrographs showing the Bmi-1 expressions in the PCCs which are treated with the hypoxic treatment using different $O_2$ levels.
Figure 4C:
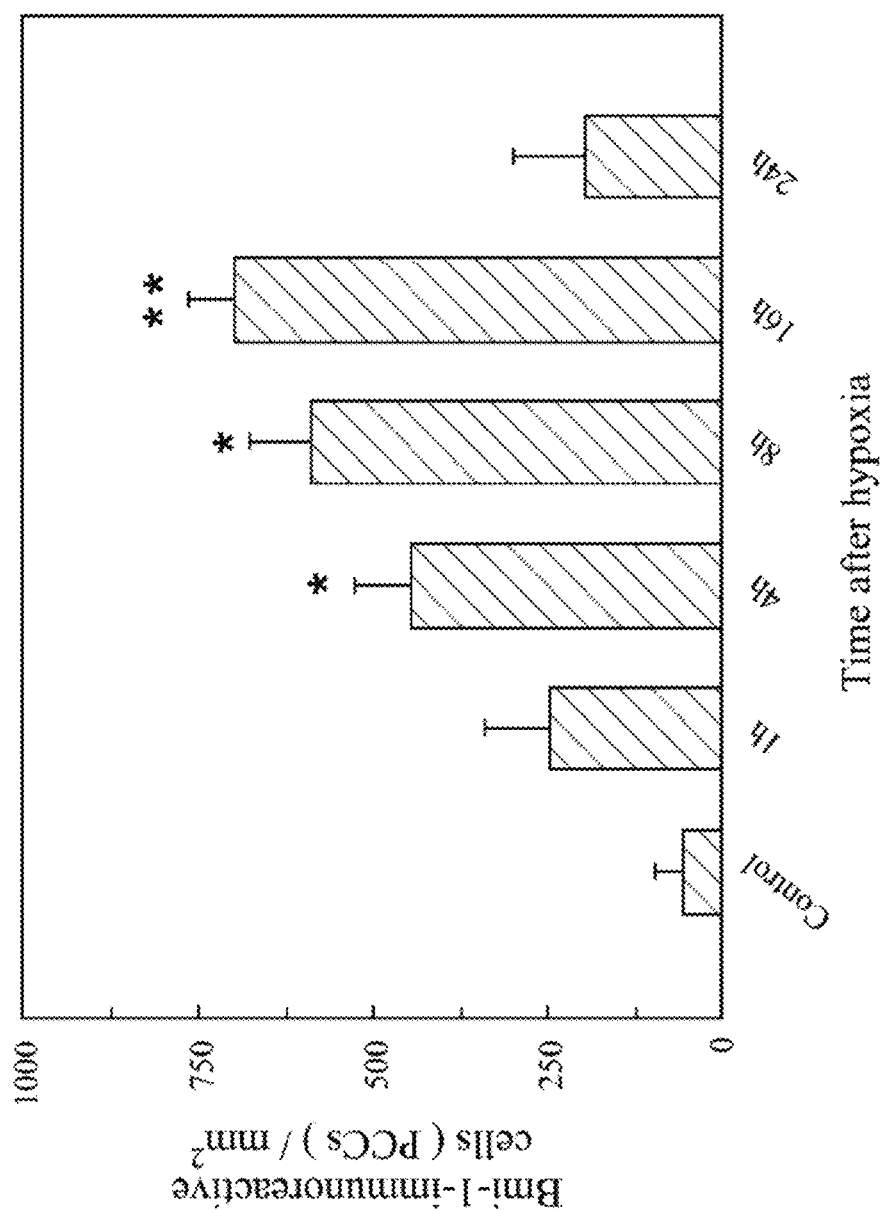
FIG. 4C is a quantitative diagram of a number of the PCCs expressing the Bmi-1 which are treated with the hypoxic treatment with different lengths of time.
Figure 4D:
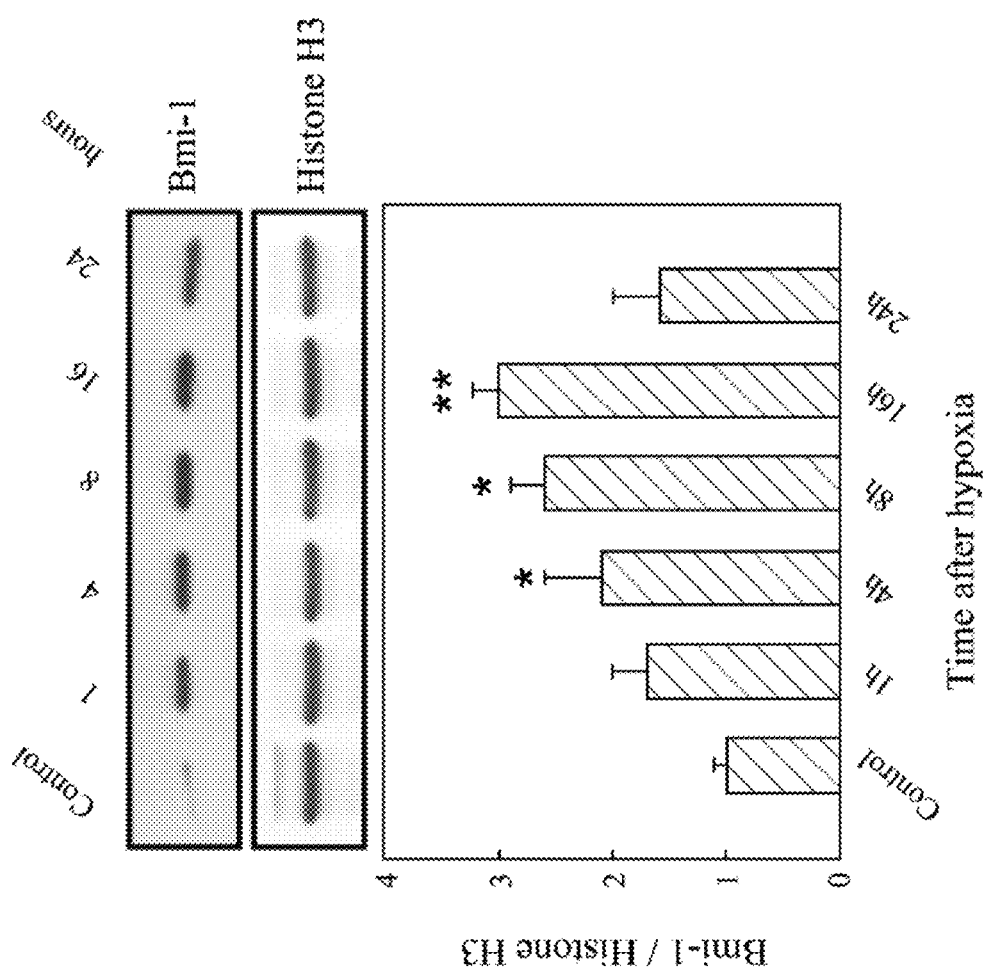
FIG. 4D shows the analytical results of the Bmi-1 expressions in the PCCs which are treated with the hypoxic treatment with different lengths of time.

FIG. 4A shows the analytical results of the Bmi-1 expressions in the PCCs which are treated with the hypoxic treatment using different $O_2$ levels. FIG. 4B are the micrograph showing the Bmi-1 expressions in the PCCs which are treated with the hypoxic treatment using different $O_2$ levels. FIG. 4C is the quantitative diagram of number of the PCCs expressing the Bmi-1 which are treated with the hypoxic treatment with different lengths of time. FIG. 4D shows the analytical results of the Bmi-1 expressions in the PCCs which are treated with the hypoxic treatment with different lengths of time. The results are represented by mean±SD values; n=8 per group, wherein * represents p<0.05 compared to the normal control, and ** represents p<0.01 compared to the normal control. In FIGS. 4A and 4B, the length of time of the hypoxic treatment of the PCCs is 8 hours. In FIGS. 4C and 4D, the $O_2$ level of the hypoxic treatment of the PCCs is 1%. The results of Bmi-1-IR and the Western blot analysis show that the Bmi-1 expressions increase after the hypoxic treatment both in a time-dependent (higher at 16 hours) and the dose-dependent (higher at 3% $O_2$ level) manner compared with the normal control without the hypoxic treatment.

3.4 Inhibition of the HIF-1α Activity Down-regulated the Bmi-1 Expressions in the Ischemic Rats To demonstrate whether the upregulation of the Bmi-1 after cerebral ischemia is mediated through an induction of the HIF-1α, an immunohistochemical analysis and the Western blot analysis are performed in the brains of the ischemic rats treated with pharmacological HIF-1α inhibitor (2-Methoxyestradiol, 2-ME2) or in HIF-1α knockout mice.

2-ME2 (Sigma Aldrich, USA) is dissolved in DMSO to obtain a 10 mmol/L solution. For in vivo experiments, the whole procedure is performed as previously described (Clin Cancer Res 2004, 10: 8665-8673). The ischemic rats are treated with an intraperitoneal injection of a liposomal preparation (di-oleoyl-phosphotidylcholine; Avanti Polar Lipids, USA) of 2-ME2 (20 mg/mL) in different concentrations (50 mg/kg, 100 mg/kg or 150 mg/kg) for 5-10 consecutive days pre- and after the onset of cerebral ischemia.

Conditional HIF-1α knockout mice (HIF-1α KO mice), HIF-1α knockout mice carrying a loxP-flanked allele of the HIF-1α, are a kind gift from Dr. Johnson (Cancer Res, 2000, 60: 4010-4015). HIF-1α disruption in the HIF-1α knockout mice is induced by feeding doxycycline at a dose of 2 mg/ml in 5% (wt /vol) sucrose solution from embryonic day 15 to postnatal day 1. They are also anesthetized with chloral hydrate (0.3 g/kg, ip) and subjected to right middle cerebral artery (MCA) ligation and right common carotid artery (CCAs) clamping for 120 minutes, as described above with modification.

Figure 5A:
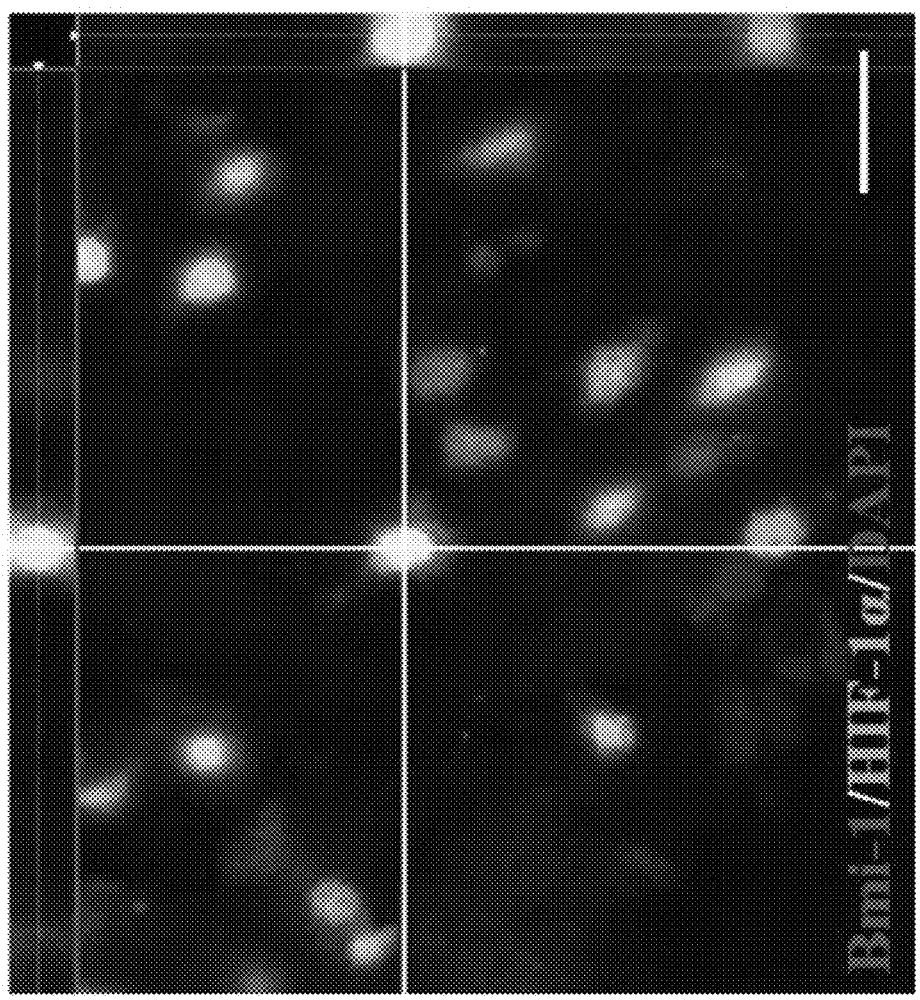
FIG. 5A is a micrograph showing the co-localization of the Bmi-1 and the HIF-1α in the brains of the ischemic rats.
Figure 5B:
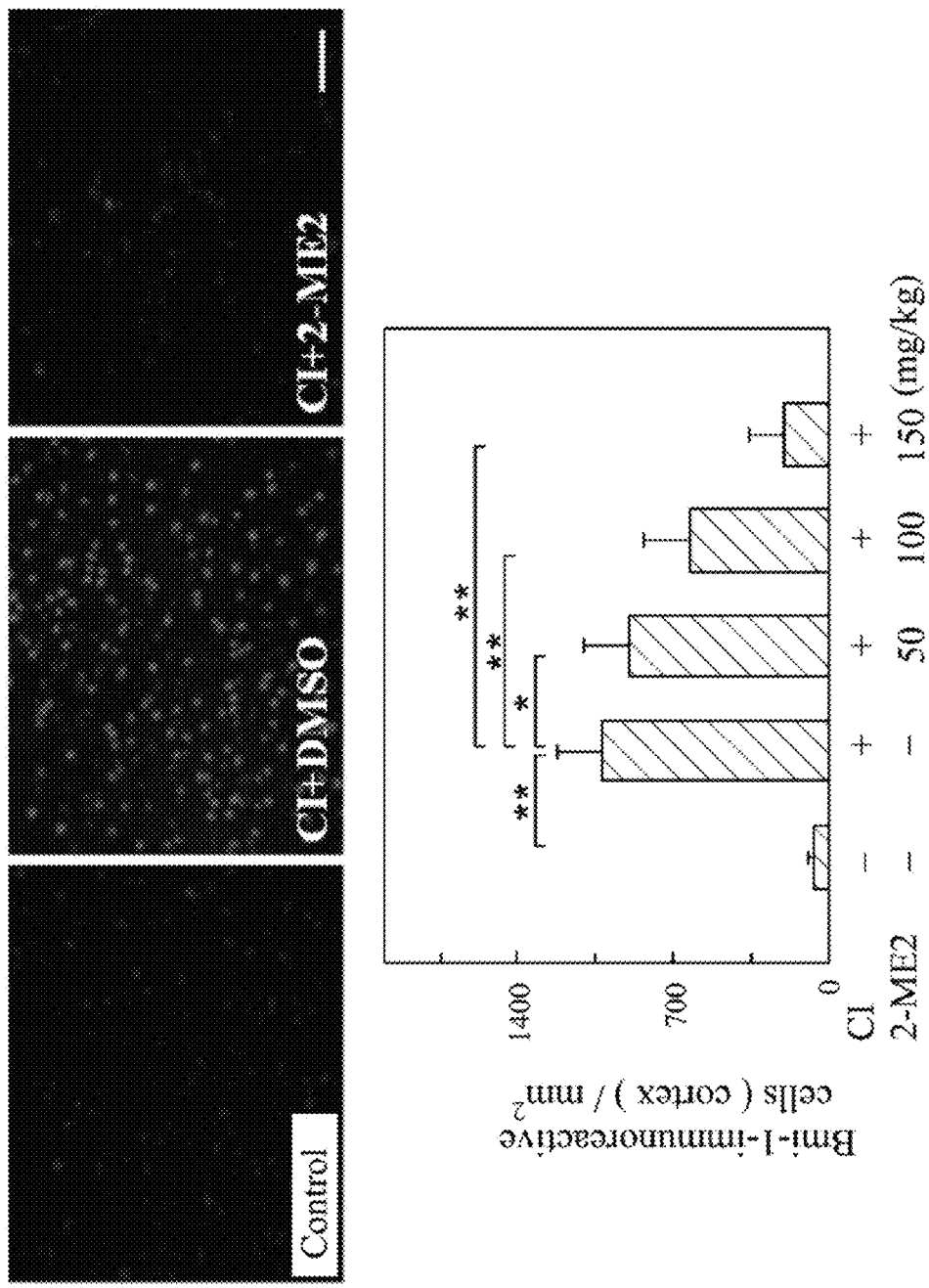
FIG. 5B are micrographs and the quantitative diagram thereof showing the Bmi-1 expressions of the brains of 2-ME2 treated ischemic rats.
Figure 5C:
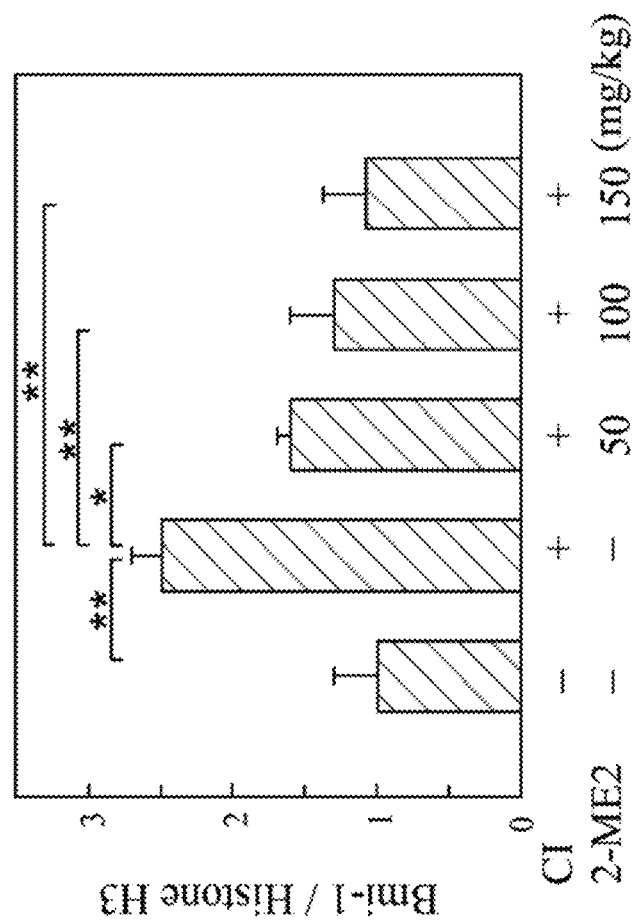
FIG. 5C shows Western blotting analysis results of the Bmi-1 expressions of the brain of the 2-ME2 treated ischemic rats.
Figure 5D:
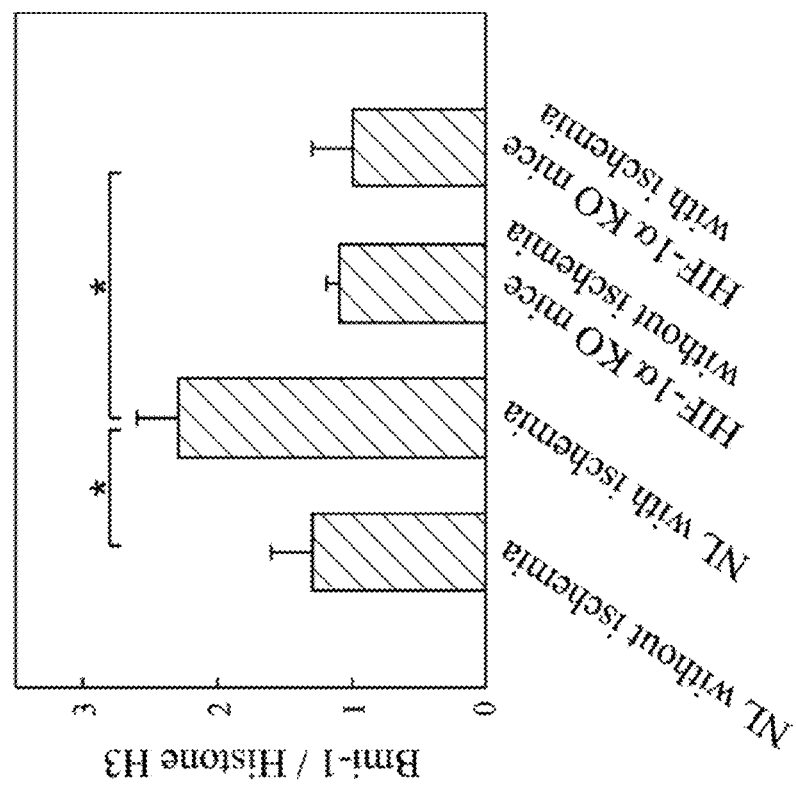
FIG. 5D shows the Western blotting analysis results of the HIF-1α expressions of the brain of HIF-1α knockout mice.
Figure 5D:
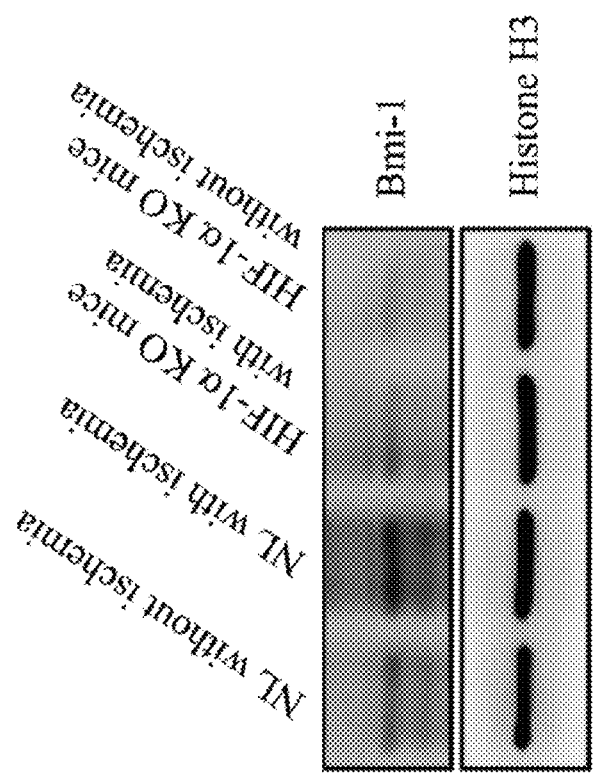

FIG. 5A is the micrograph showing the co-localization of the Bmi-1 and the HIF-1α in the brains of the ischemic rats. FIG. 5B are the micrographs and the quantitative diagram thereof showing the Bmi-1 expressions of the brains of the 2-ME2 treated ischemic rats. FIG. 5C shows the Western blotting analysis results of the Bmi-1 expressions of the brain of the 2-ME2 treated ischemic rats. FIG. 5D shows the Western blotting analysis results of the HIF-1α expressions of the brains of the HIF-1α knockout mice. The NL (normal littermate) represents littermates of the HIF-1α knockout mice without knockout HIF-1α. In FIG. 5A, the ischemic cortical areas of the rats reveal increase in the Bmi-1+ cells co-expressing the HIF-1α+ cells. In FIGS. 5B and 5C, the upregulated Bmi-1 immunoreactivity and the protein expressions after the cerebral ischemia are suppressed by 2-ME2 injection in the dose-dependent manner. In FIG. 5D, the Bmi-1 expressions of the brains in the ischemic normal mice (with ischemia-reperfusion model) compared to the normal mice without ischemia-reperfusion model are increased, but ischemia-induced Bmi-1 upregulation is not present in brain samples of the HIF-1α knockout mice.

These results indicate that the inhibition of HIF-1α activity in the ischemic rats (or the mice) negatively regulates the expressions of the Bmi-1.

3.5 Hypoxia Induced Nuclear Translocation of the HIF-1α in the PCCs

The subcellular locations of the HIF-1α and the Bmi-1 in the PCCs under hypoxia are examined by double immunofluorescence study. The PCCs are divided into three groups. One group is cultured with 21% of $O_2$ as a control group. Another group is cultured with 1% of $O_2$ for 8 hours as a hypoxic group. The other group is treated with 1 μM of 2-ME2 for 16 hours and then cultured with 1% of $O_2$ for 8 hours as a 2-ME2 treated hypoxic group.

Figure 6A:
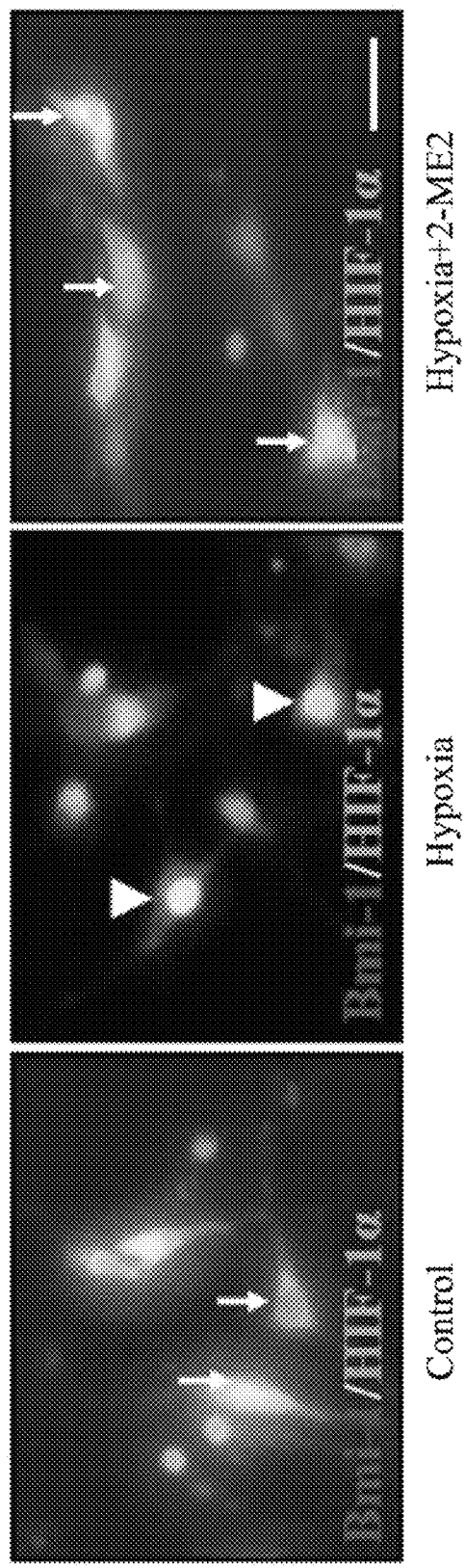
FIG. 6A are micrographs showing locations of the HIF-1α and the Bmi-1 in the PCCs under different conditions.

FIG. 6A are the micrographs showing locations of the HIF-1α and the Bmi-1 in the PCCs under different conditions. In FIG. 6A, the HIF-1α is both localized in the cytosol (including neurite) and nucleus under normal condition (the control group), whereas the HIF-1α translocates into the nuclei or to perinuclear areas under hypoxic condition, which co-expresses with Bmi-1. However, pretreatment of the PCCs with 2-ME2 for 16 hours abolishes the translocation of the HIF-1α to the nucleus.

Figure 6B:
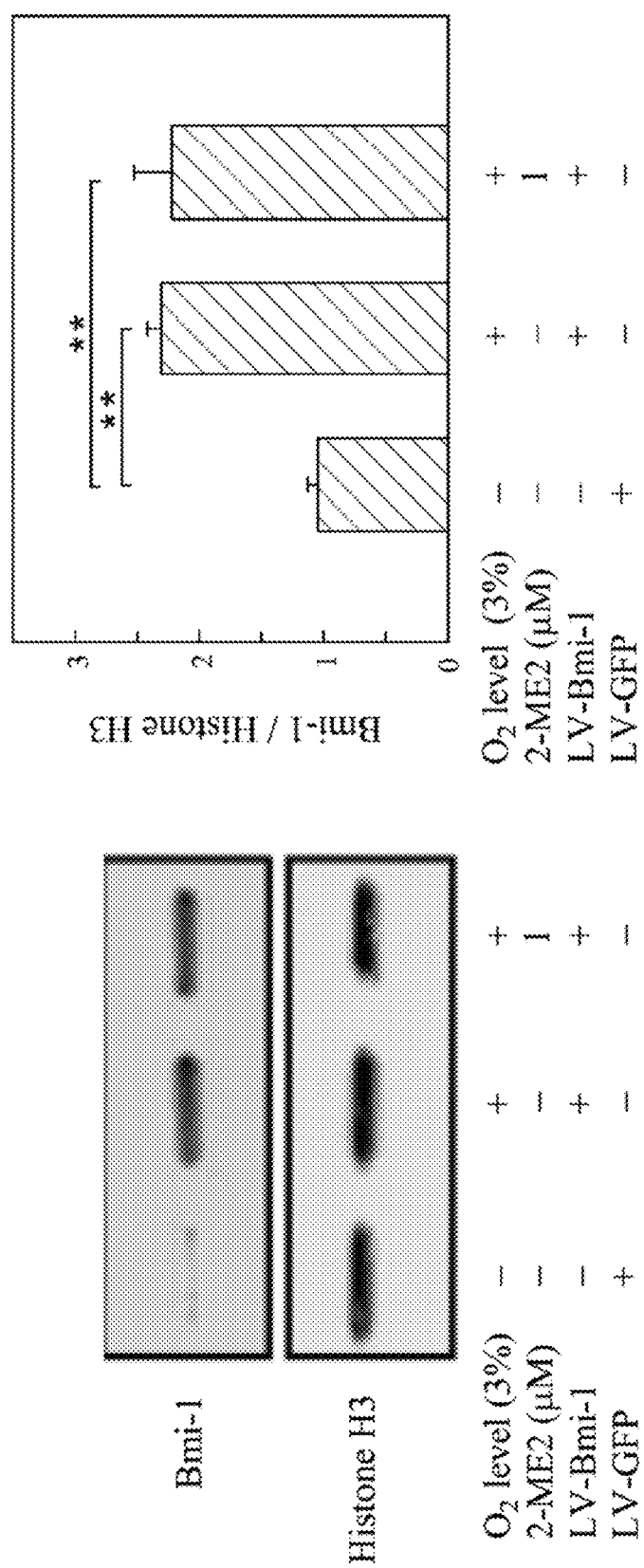
FIG. 6B shows analytical results of the Bmi-1 expressions in the PCCs which are treated with the hypoxic treatment after a Bmi-1 transient expression.

The relationship between the HIF-1α activation and the Bmi-1 expressions is further analyzed by the Western blot analysis in this example. FIG. 6B shows the analytical results of the Bmi-1 expressions in the PCCs which are treated with the hypoxic treatment after a Bmi-1 transient expression. One group of the PCCs is transfected with LV-Bmi-1 to transient express the Bmi-1. Another group of the PCCs is treated with 1 μM of 2-ME2 for 16 hours and then transfected with the LV-Bmi-1. The other group of the PCCs is transfected with LV-GFP as the control group. In FIG. 6B, the PCCs transfected with the LV-Bmi-1 overexpress the Bmi-1. However, the overexpressions of the Bmi-1 are not affected by the pretreatment of the PCCs with 2-ME2.

Figure 6C:
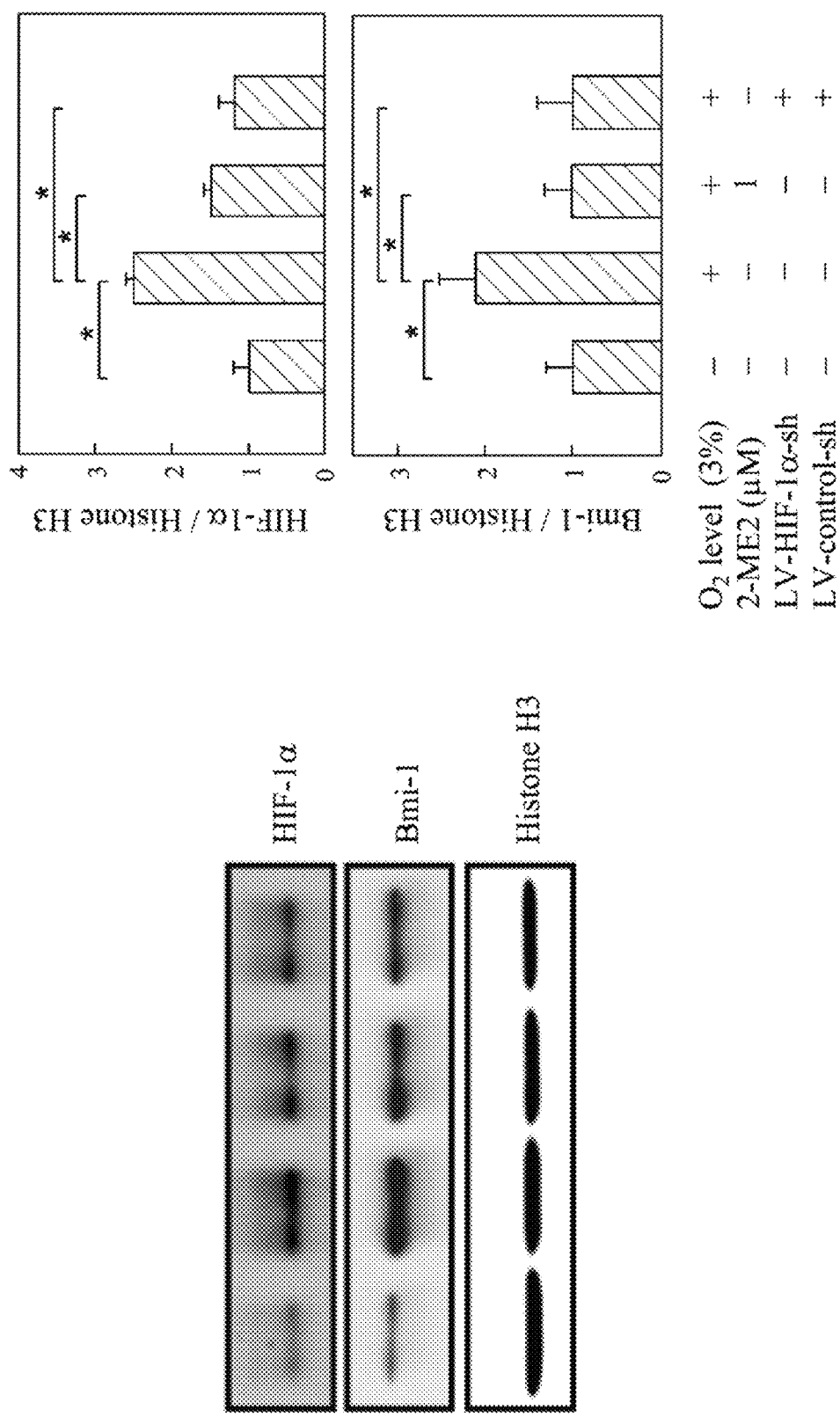
FIG. 6C shows analytical results of the Bmi-1 expressions in the PCCs which are treated with the hypoxic treatment after inhibiting the HIF-1α expressions.

FIG. 6C shows the analytical results of the Bmi-1 expressions in the PCCs which are treated with the hypoxic treatment after inhibiting the HIF-1α expressions. One group of the PCCs is transduced with LV-HIF-1α-sh (sc-35562-V, Santa Cruz Biotechnology) and LV-control-sh (sc-108080, Santa Cruz Biotechnology) by a lenti-viral infection to reduce the HIF-1α expressions. Another group of the PCCs is treated with 1 μM of 2-ME2 for 16 hours to reduce the HIF-1α expressions in the PCCs. In FIG. 6C, the HIF-1α expressions in the PCCs are decreased both in the LV-HIF-1α-sh transduced group and the 2-ME2 treated group. The Bmi-1 expressions of the PCCs are also reduced.

These results indicate that both the HIF-1α translocation and the Bmi-1 expressions required the HIF-1α activity. The effect of 2-ME2 is specific to HIF-1α-induced Bmi-1 expressions, as it has no effect on lenti-viral (LV-Bmi-1) infection-induced Bmi-1 expressions.

3.6 The HIF-1α is Recruited to the BMI-1 Gene Promoter in Response to the Hypoxia To prove the hypoxia-induced Bmi-1 upregulation only through the HIF-1α, the HIF-1α expressions or HIF-2α expressions of the PCCs are inhibited, and then treated with the hypoxic treatment to observe the relationship between the HIF-1α and the Bmi-1 or between the HIF-2α and the Bmi-1. The PCCs are transduced with the LV-HIF-1α-sh or LV-HIF-2α-sh (sc-35316-V, Santa Cruz Biotechnology) by the lenti-viral infection to reduce the HIF-1α expressions or the HIF-2α (another member of the hypoxia-inducible factor-α) expressions. The PCCs transduced with the LV-control-sh are used as normal control.

Figure 7A:
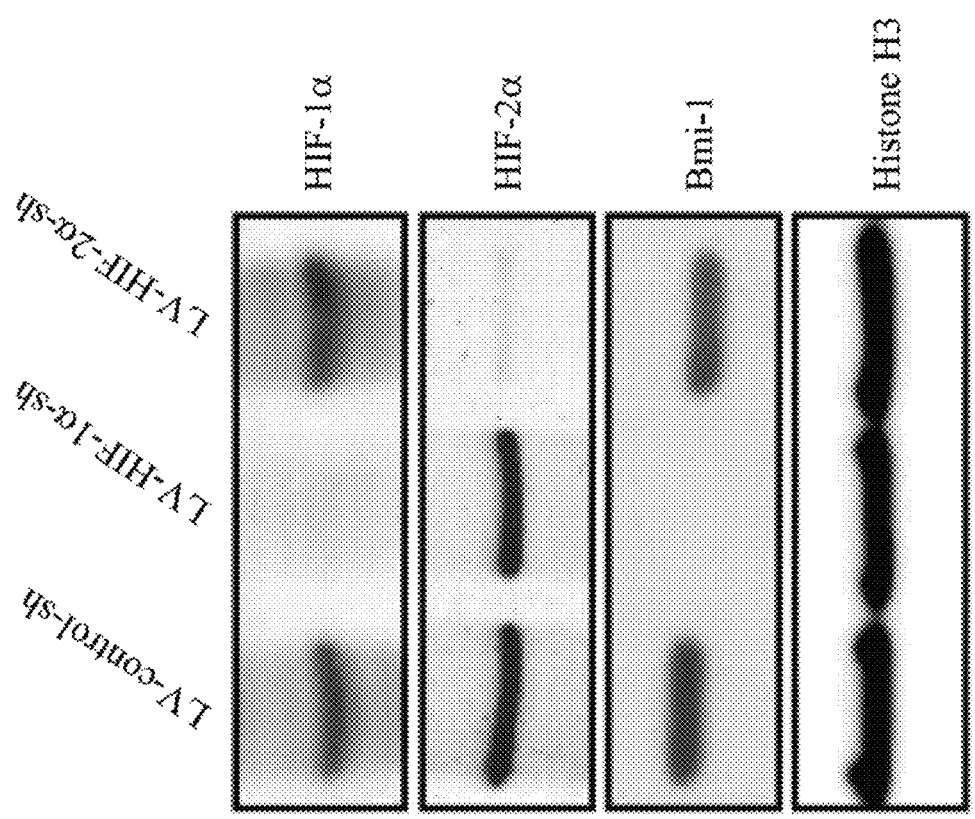
FIG. 7A shows analytical results of the Bmi-1 expressions in the PCCs which are treated with the hypoxic treatment after inhibiting the HIF-1α expressions or the HIF-2α expressions.

FIG. 7A shows the analytical results of the Bmi-1 expressions in the PCCs which are treated with the hypoxic treatment after inhibiting the HIF-1α expressions or the HIF-2α expressions. The Bmi-1 expressions are detected by the Western blot analysis. In FIG. 7A, the Bmi-1 expressions are not detected in the PCCs inhibited the HIF-1α expression. However, the Bmi-1 expressions are not affected in the PCCs inhibited the HIF-2α expression. The result indicates that the Bmi-1 expressions are regulated by the HIF-1α but not the HIF-2α under the hypoxia.

In order to obtain direct evidence for the interaction between the HIF-1α and a Bmi-1 promoter, chromatin immunoprecipitation (ChIP) assay is used in this example. The PCCs are cultured with 3% of $O_2$ for 4 hours, and then are fixed with 1% of formaldehyde (added directly to the culture medium) for 20 minutes at 37° C. to allow for reversible cross-linkage. The binding of the HIF-1α to the Bmi-1 promoter (NCBI Accession number: NC_000010.10) is examined using a commercial kit for the ChIP assay (Upstate Biotechnology). DNA-protein complexes are immunoprecipitated with primary antibody against the HIF-1α linked to protein A agarose beads, and eluted with 1% of sodium dodecylsulfate (SDS), and 0.1 M of $NaHCO_3$. The cross-links of the DNA-protein complexes are reversed by incubation at 65° C. for 5 hours, and the proteins are removed with proteinase K. Isolated DNA is extracted with phenol/chloroform, re-dissolved and PCR-amplified with Bmi-1 promoter primers (PCR product: 114 bp), wherein the sequence of sense primer is 5'-CCGCGGGTG-GAAGGGGAGCC-3', and the sequence, of antisense primer is 5'-GGGGCCGGCAGGCGCGGGGC-3'.

Figure 7B:
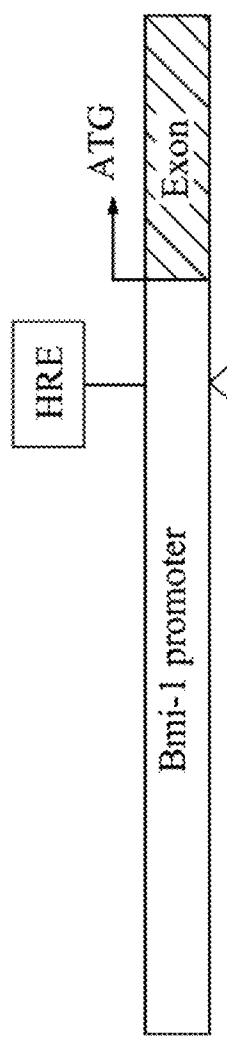
FIG. 7B is a schematic view of a 5'-flanking Bmi-1 genomic region.
Figure 7C:
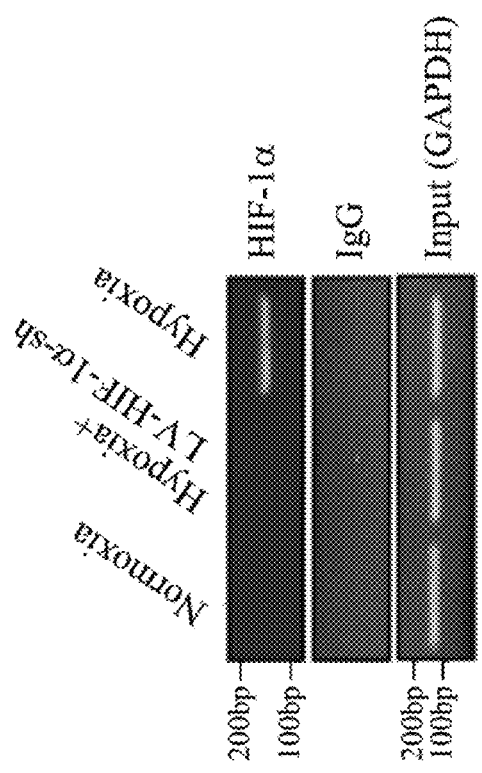
FIG. 7C shows chromatin immunoprecipitation assay results of the PCCs.

FIG. 7B is a schematic view of a 5'-flanking Bmi-1 genomic region. FIG. 7C shows the ChIP assay results of the PCCs. In FIG. 7B, the 5'-flanking Bmi-1 genomic region includes a promoter region of the Bmi-1, a first exon and a HRE (hormone response element) binding site corresponding to nucleotides −272 to −268 (relative to putative transcription start site+1). In FIG. 7C, 4 hours hypoxia of the PCCs recruits the HIF-1α to bind on the Bmi-1 promoter, which is abolished by the LV-HIF-1α-shRNA transduction in the PCCs. These results indicate that the HIF-1α is recruited binding on the Bmi-1 promoter to upregulate the Bmi-1 expressions.

3.7 Upregulation of the Bmi-1 Under the Hypoxia is Mediated by a HIF-1α-induced Transcriptional Activity To determine whether the enhancement of the Bmi-1 expressions is a result of activated HIF-1α binding to the HRE on the Bmi-1 promoter under hypoxia, different plasmids are constructed for a luciferase reporter assay to detect luciferase activities under hypoxia in this example. The plasmids include a luciferase reporter gene construct (pBmi-1-luc-1), a control construct (pBmi-1-luc-2) and a HRE-mutant construct (pBmi-1mutHER).

Figure 8A:
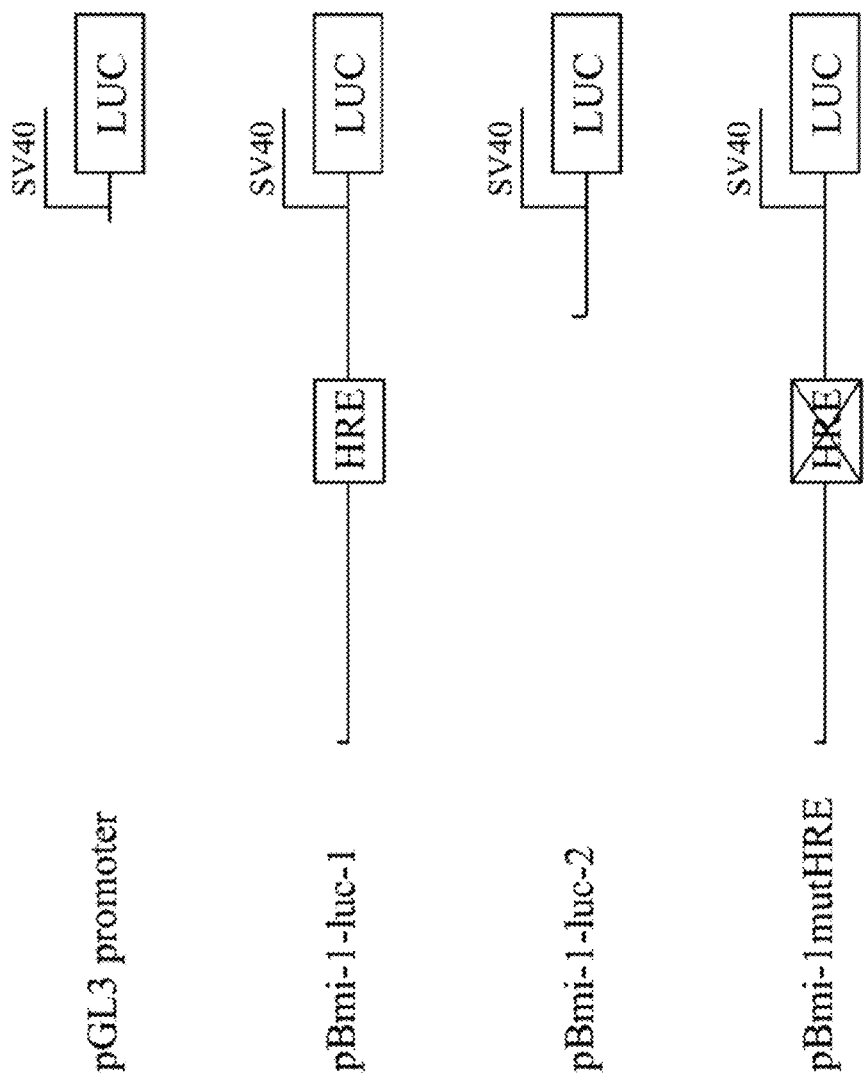
FIG. 8A is a schematic view of 5'-flanking genomic regions of plasmid constructs.

FIG. 8A is a schematic view of 5'-flanking genomic regions of the pBmi-1-luc-1, the pBmi-1-luc-2 and the pBmi-1mutHER. A fragment containing the 5'-flanking region (~900 bp) of the human Bmi-1 gene promoter is cloned into the XhoI and HindIII sites of a pGL3-basic vector (Promega) to generate the pBmi-1-luc-1, wherein the pGL3-basic vector contains one real HRE binding site and a luciferase reporter. One additional Bmi-1 promoter constructs (pBmi-1-luc2) without the HRE binding site is generated using the same downstream primer as for pBmi-1-luc1. In the pBmi-1-mutHRE construct, the putative HRE of the pBmi-1-luc1 is replaced from 5'-GCGTG-3' to 5'-AAAAG-3'. 3T3 cells at about 90% confluence in 24-well plates are transiently transfected with different plasmids respectively by using Lipofectamine 2000 (Invitrogen). To correct for variable transfection efficiency, the 3T3 cells are cotransfected with the pRL-SV40 vector encoding the Renilla luciferase gene. After transduction, the 3T3 cells are cultured under hypoxia. The 3T3 cells are lysed and the luciferase activities are determined with a multiwell luminescence reader (Molecular Devices) by using the Dual-Luciferase Reporter Assay System (Promega).

Figure 8B:
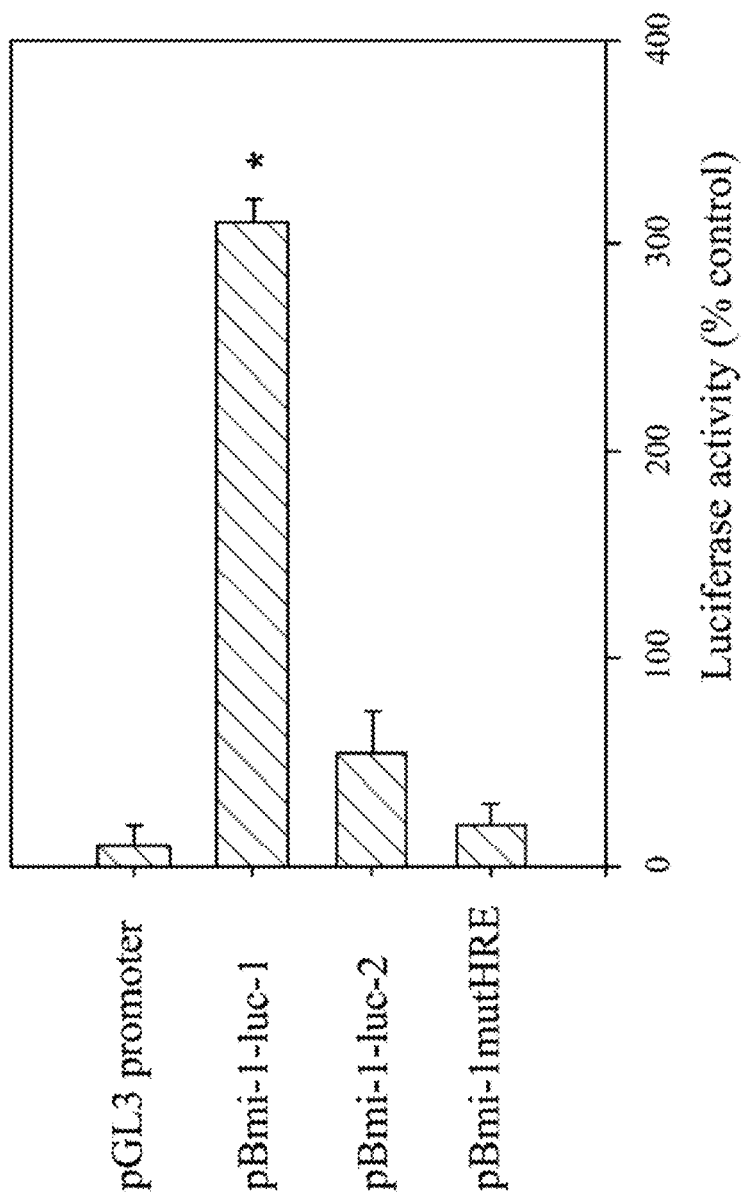
FIG. 8B shows luciferase reporter assay results.

FIG. 8B shows luciferase reporter assay results, wherein the results are represented by mean±SD values; * represents p<0.05 compared to the control. In FIG. 8B, the luciferase activity of the pBmi-1-luc1 is much higher than other groups. The pBmi-1-luc1 contains complete HRE binding site compared to the pBmi-1-luc2 and the pBmi-1-mutHRE. The result indicates that the HIF-1α activation needs binding to the HRE binding site of the Bmi-1 promoter to promote the enhancement of the Bmi-1 expressions.

3.8 The Hypoxia Stimulates the Proliferation and the Self-renewal of the NSC In Vitro Through the HIF-1α-Bmi-1 Pathway To determine whether the HIF-1α-Bmi-1 pathway regulates the proliferation of the NSCs a neurosphere self-renewal assay is performed in this example. In the neurosphere self-renewal assay, the NSCs are cultured in non-adherent cultures to form neurospheres for examining the effect of the HIF-1α-Bmi-1 pathway on the self-renewal of the neurosphere.

To prepare the NSCs, after removal of meninges, subventricular zones (SVZ) of lateral ventricles from adult mice brain (4 week-of-age) are aseptically isolated and dissociated as previously described (J Cell Sci 2006; 119, 4467-4474). All steps are operated under sterile conditions. Then, neurosphere culture are prepared in neurobasal (NB) medium (Gibco BRL) supplemented with 2% of B27 (Gibco BRL), 2 mM of L-glutamine (PAN Biotech), 100 U/ml of penicillin/0.1 mg/L of streptomycin (Gibco BRL). For maintenance and expansion of the cultures, the NB/B27 is further supplemented with 2 μg/mL of heparin (Sigma), 20 ng/mL of FGF-2 (R&D Systems) and 20 ng/mL of EGF (R&D Systems). Neurosphere cultures are maintained at 37° C. in a humidified incubator with 5% $CO_2$. For clonal/low density cultures, primary neurospheres grown at high density are dissociated into a single cell suspension and reseeded into 96-well plates at 100 cells per ml of media and the number of newly formed neurospheres is counted after 7 days. In addition, the Bmi-1 expressions, SOX2 expressions, Nestin expressions, Musashi-1 expressions, BrdU expressions and ki-67 expressions of the newly formed neurospheres are determined by the immunofluorescence staining.

Figure 9A:
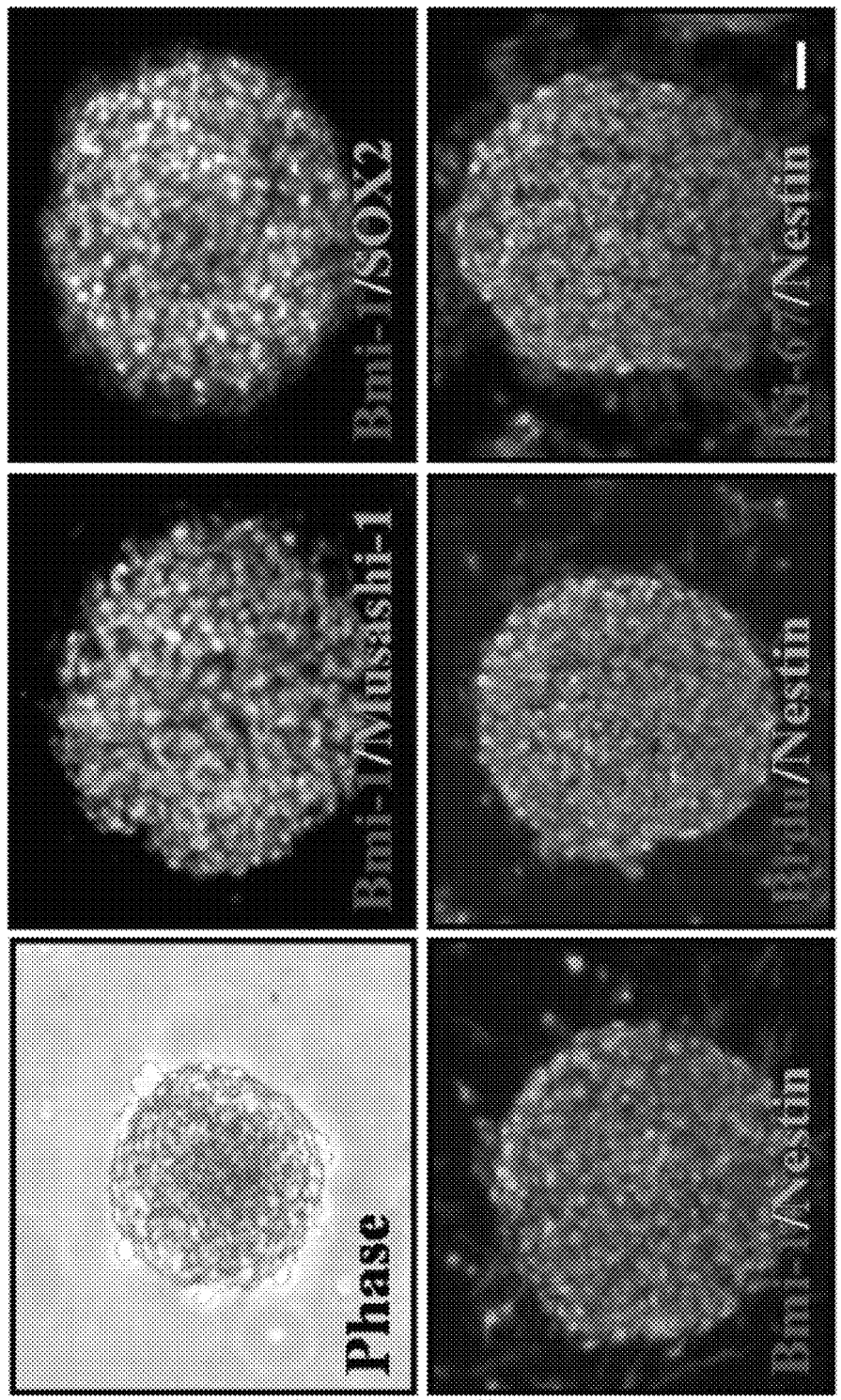
FIG. 9A are micrographs of neurosphere formations of neural stem cells (NSCs)

FIG. 9A are the micrographs of neurosphere formations of the NSCs, wherein the scales bar represents 50 μm. In FIG. 9A, the Bmi-1 co-expresses with stem cells marker of the Musashi-1, the SOX2 and the Nestin in the neurosphere. Nestin$^+$ neurosphere also is co-stained with the proliferation marker of the BrdU and the ki-67.

The NSCs are further cultured with different $O_2$ levels (21%, 1%, 3% and 5%) to observe the effect of the hypoxia and the normal condition on the number of the neurosphere formation. FIG. 9B shows the micrographs of the neurosphere formation of the NSCs treated with the hypoxic treatment. In FIG. 9B, the hypoxia with $O_2$ level at 3% stimulates a significantly higher frequency of the neurosphere formation.

The NSCs are transduced with the LV-Bmi-1-sh or, the LV-HIF-1α-sh by the lenti-viral infection and then cultured under different $O_2$ levels respectively to observe a frequency of the neurosphere formation, a self-renewal potential of the NSCs, a neurosphere size and proportions of BrdU$^+$ cells and ki-67$^+$ cells. The self-renewal potential of the NSCs is estimated by the Nestin expressions of the NSCs.

In this example, another group of the NSCs is prepared from the SVZ of the lateral ventricles of Bmi-1 knockout mice, and the other group of the NSCs is prepared from the SVZ of the lateral ventricles of normal littermate (NL) of the Bmi-1 knockout mice. The Bmi-1 knockout mice are null mutations (Bmi-1$^{-/-}$) obtained from mice heterozygous of Bmi-1$^{+/-}$ mating. The Bmi-1$^{+/-}$ mice are a kind gift from Dr. Van Lohuizen (J Clin Invest 2012; 122, 1920-1932). The aforementioned NSCs are cultured in the neurosphere culture, transduced with the LV-HIF-1α-sh by the lenti-viral infection, and then further cultured under different $O_2$ levels (3% or 21%) in the neurosphere culture respectively to observe the frequency of the neurosphere formation, the elf-renewal potential of the NSCs, the neurosphere size and the proportions of BrdU$^+$ cells and ki-67$^+$ cells under different conditions.

Figure 9C:
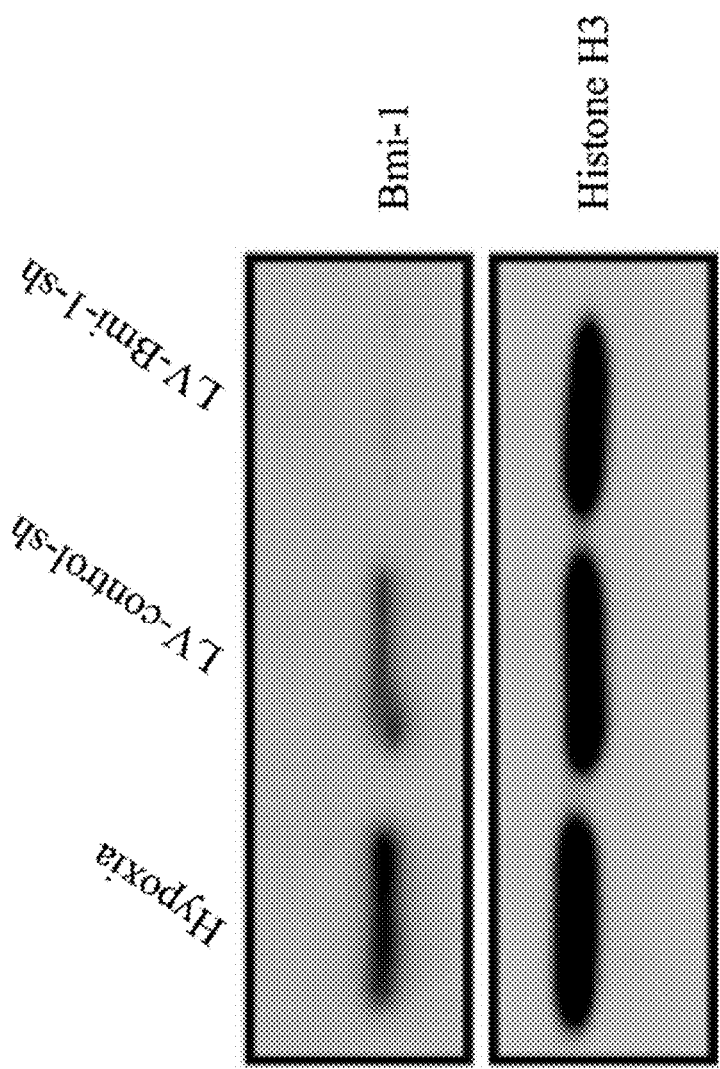
FIG. 9C shows the Bmi-1 expressions of the NSCs transduced with the LV-Bmi-1-sh.
Figure 9D:
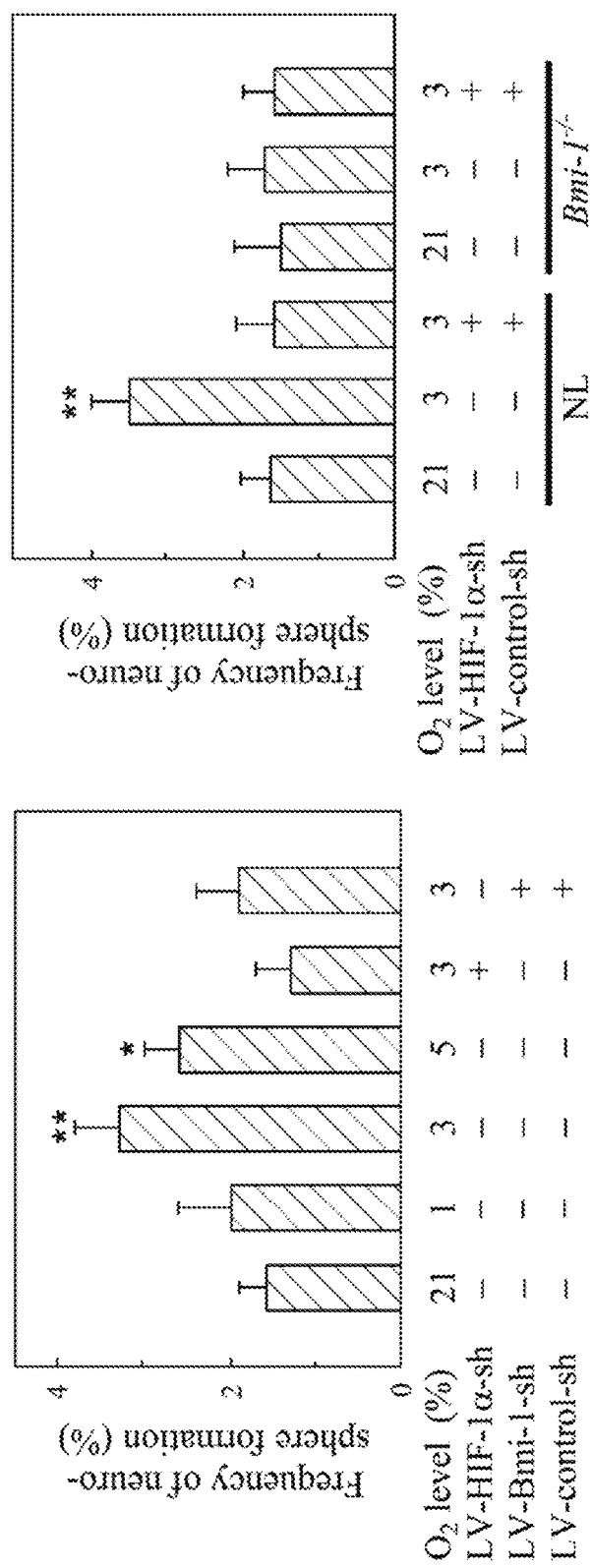
FIG. 9D is the quantitative diagram of a frequency of the neurosphere formation in the neurosphere culture under different $O_2$ levels.
Figure 9E:
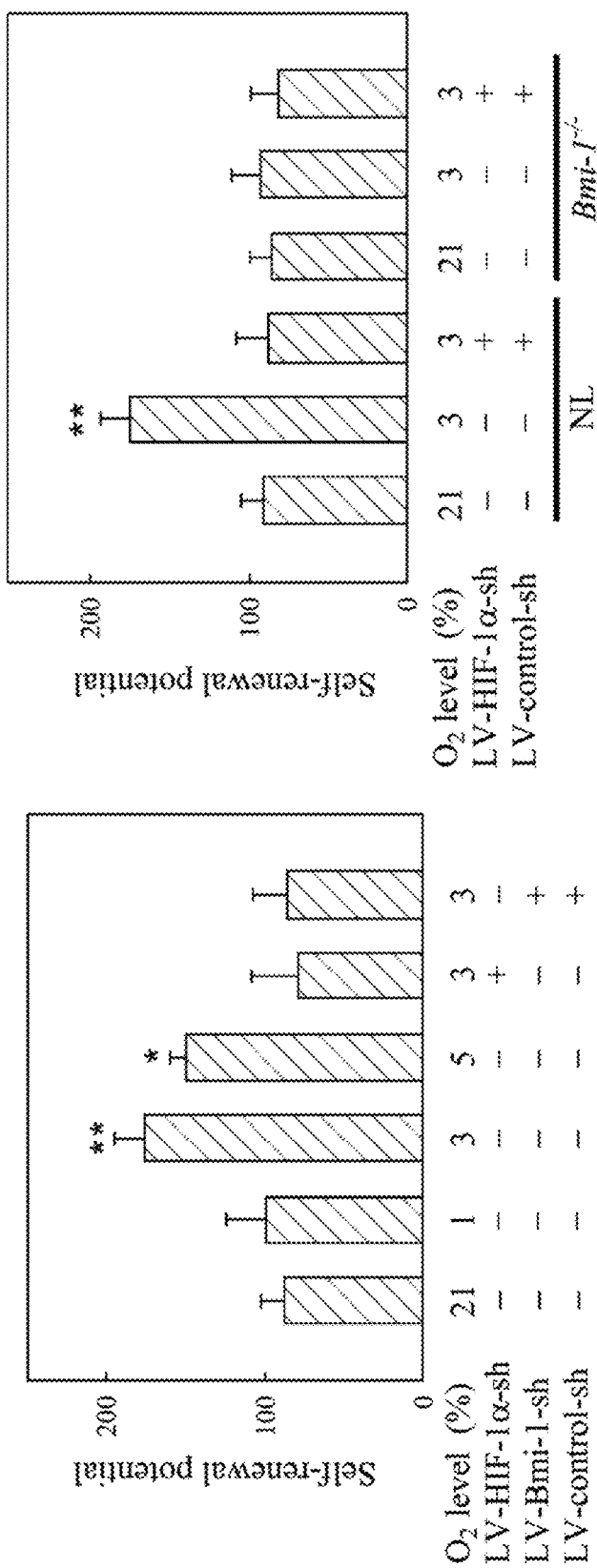
FIG. 9E is the quantitative diagram of a self-renewal potential of the NSCs in the neurosphere culture under different $O_2$ levels.
Figure 9F:
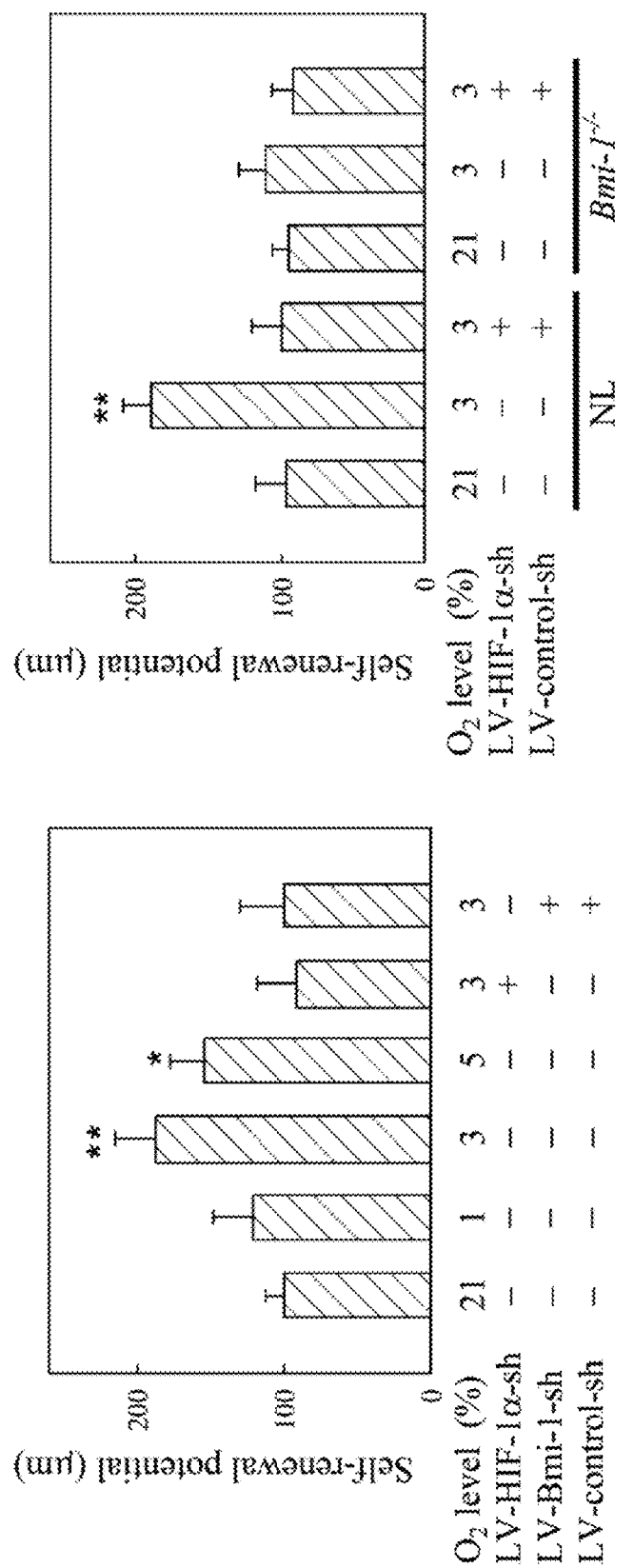
FIG. 9F is the quantitative diagram of a neurosphere size in the neurosphere culture under different $O_2$ levels.
Figure 9G:
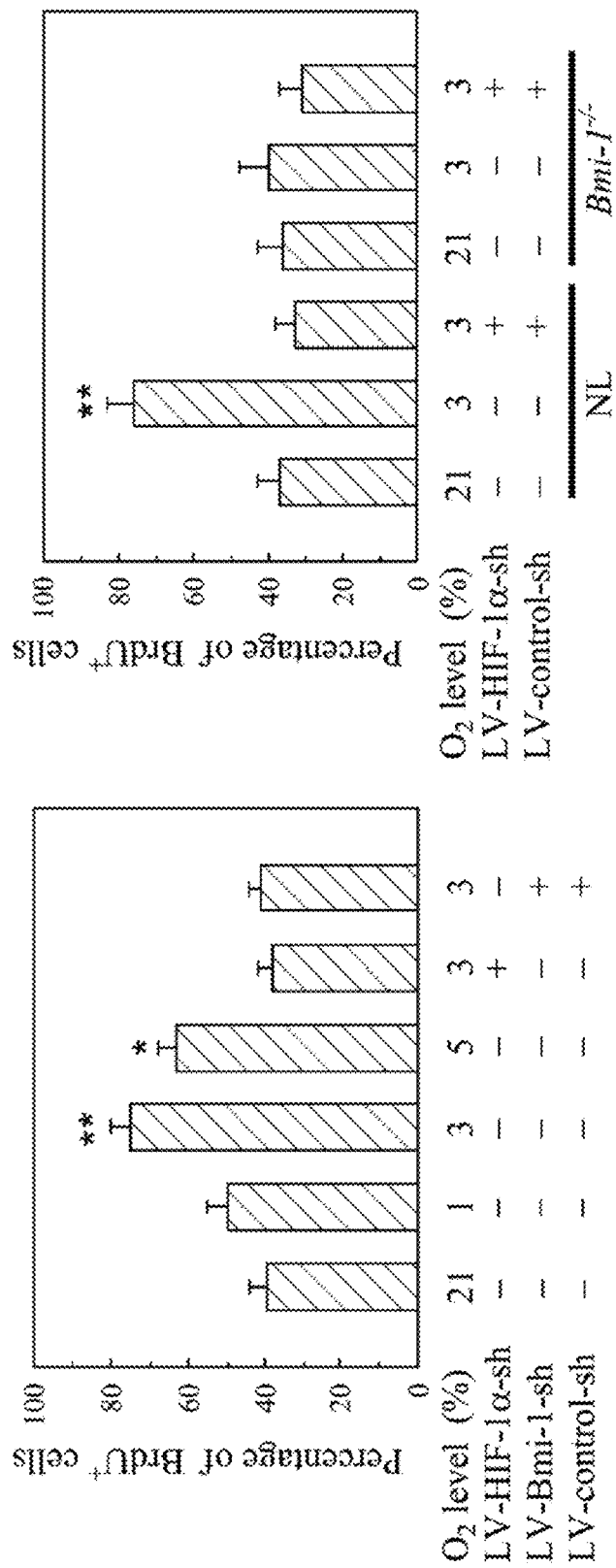
FIG. 9G is the quantitative diagram of a proportion of BrdU$^+$ cells in the neurosphere culture under different $O_2$ levels.
Figure 9H:
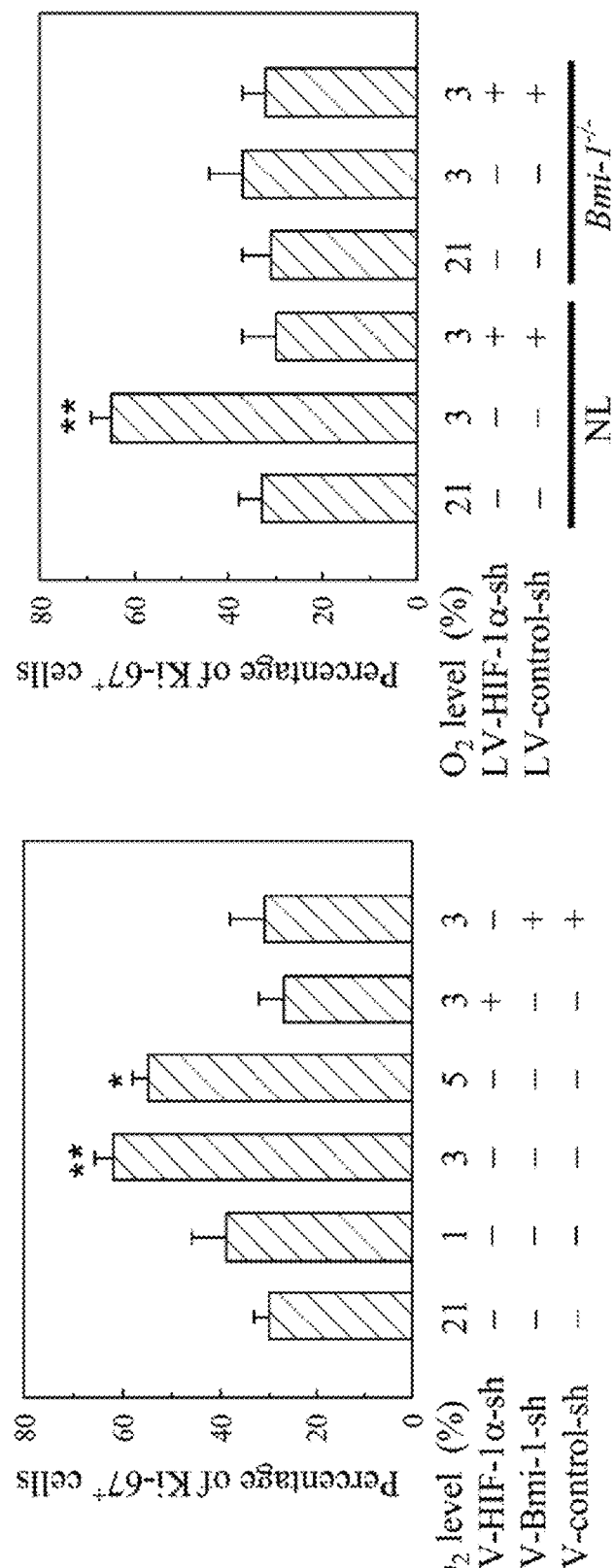
FIG. 9H is the quantitative diagram of the proportion of ki-67$^+$ cells in the neurosphere culture under different $O_2$ levels.

FIG. 9C shows the Bmi-1 expressions of the NSCs transduced with the LV-Bmi-1-sh. FIG. 9D is the quantitative diagram of the frequency of the neurosphere formation in the neurosphere culture under different $O_2$ levels. FIG. 9E is the quantitative diagram of the self-renewal potential of the NSCs in the neurosphere culture under different $O_2$ levels. FIG. 9F is the quantitative diagram of the neurosphere size in the neurosphere culture under different $O_2$ levels. FIG. 9G is the quantitative diagram of the proportion of the BrdU$^+$ cells in the neurosphere culture under different $O_2$ levels. FIG. 9H is the quantitative diagram of the proportion of the ki-67$^{30}$ cells in the neurosphere culture under different $O_2$ levels. The results are represented by mean±SD values; wherein * represents p<0.05 compared to control, and ** represents p<0.01 compared to the control.

In FIG. 9C, the transduction of the LV-Bmi-1-sh indeed reduces the Bmi-1 expressions of the NSCs. Moreover, the NSCs overexpress the Bmi-1 under the hypoxia (3% of $O_2$) compared to the NSCs transduced the LV-Bmi-1-sh with normoxia (21% of $O_2$). In FIGS. 9D to 9F, the NSCs prepared from the Bmi-1 knockout mice (Bmi-1$^{-/-}$) significantly increase the frequency of the neurosphere formation, the self-renewal potential of the NSCs and neurosphere size compared to that from their normal littermate (NL) under the hypoxia, in particular under 3% of $O_2$. However, the administrations of gene knockdown manipulation by the LV-HIF-1α-sh or the LV-Bmi-1-sh into the culture abolish all the proliferation effect on the NSCs. In FIGS. 9G and 9H, the hypoxia also significantly increases a BrdU incorporation and a ki-67 immunostaining in the NSCs compared to the normoxia, in particular under 3% of $O_2$. Conversely, the enhancements of the BrdU incorporation and the ki-67 immunostaining are inhibited by the administration of the lentiviral infection of the LV-HIF-1α-sh or the LV-Bmi-1-sh in the NSCs.

Taken together, these findings indicate that the hypoxia could promote the proliferation and self renewal potential of the NSCs via regulating the HIF-1α-Bmi-1 pathway in vitro.

IV. The Stroke Treatment Effect of the Bicyclic Compound of the Present Disclosure The data of the second part examples demonstrate that the bicyclic compound of the present disclosure has the ability to protect the NSCs. This part of the examples further discuss capacities of the bicyclic compound of the present disclosure to promote the proliferation and the self-renewal of the NSCs in vitro and in vivo, and the effect of bicyclic compound of the present disclosure on the treatment of a brain injury to a subject. The bicyclic compound used in this part of the examples is the Compound 1, which reduces most LDH release rate in the LDH release rate analysis. It should be understood that the effect of a mixture containing the Compound 1 as a main active ingredient can be inferred from the effect of the pure Compound 1.

4.1 The Compound 1 Promotes the Proliferation and the Self-renewal of the NSCs In Vitro Through the HIF-1α-Bmi-1 Pathway i. The Effect of the Compound 1 on the HIF-1α Expressions and the Bmi-1 Expressions of the NSCs In Vitro To investigate whether the Compound 1 modulates the self-renewal of NSCs, this example first examines the effect of the Compound 1 on the HIF-1α expressions and the Bmi-1 expressions under normoxia (21% of $O_2$) in the neurosphere.

Figure 10A:
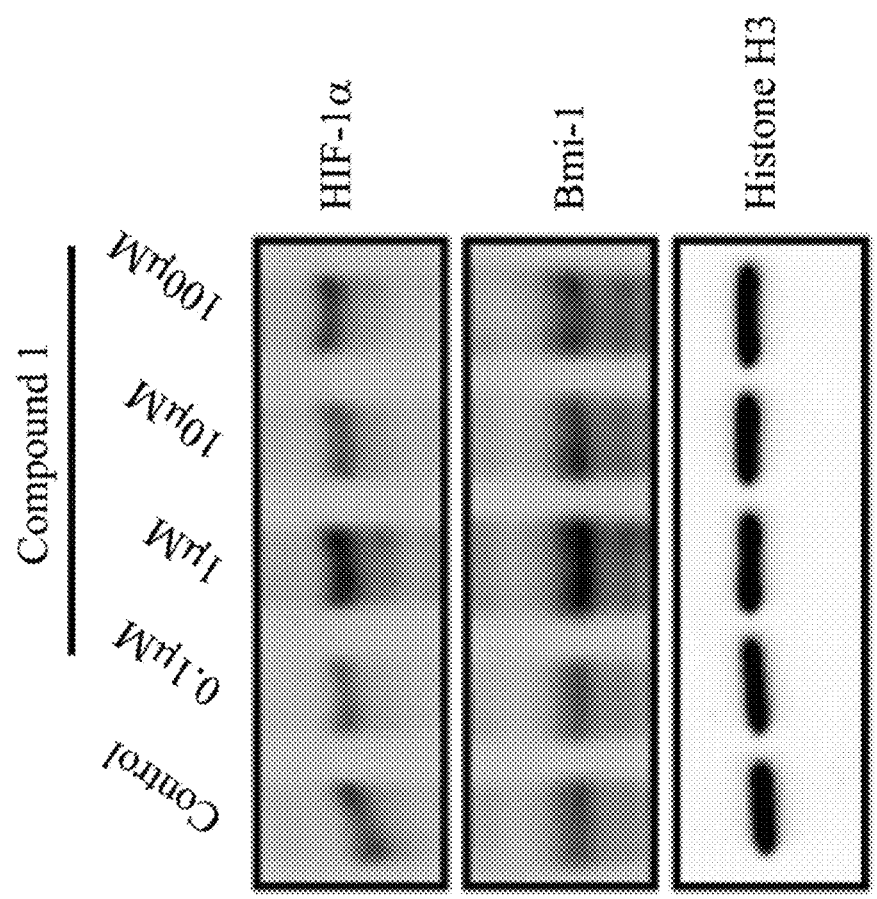
FIG. 10A shows the analytical results of the HIF-1α expressions and the Bmi-1 expressions of the NSCs affecting by a Compound 1.

The NSCs are exposed to the various dosages of the Compound 1 (0.1 μM, 1 μM, 10 μM and 100 μM) and cultured in the neurosphere culture. The HIF-1α expressions and the Bmi-1 expressions of the NSCs are detected by the Western blot analysis. The control group of the NSCs is cultured in the neurosphere culture without exposed to the Compound 1. FIG. 10A shows the analytical results of the HIF-1α expressions and the Bmi-1 expressions of the NSCs affecting by the Compound 1. In FIG. 10A, the HIF-1α expressions and the Bmi-1 expressions of the NSCs are increased after adding the Compound 1, in particular the 1 μM of the Compound 1.

Figure 10B:
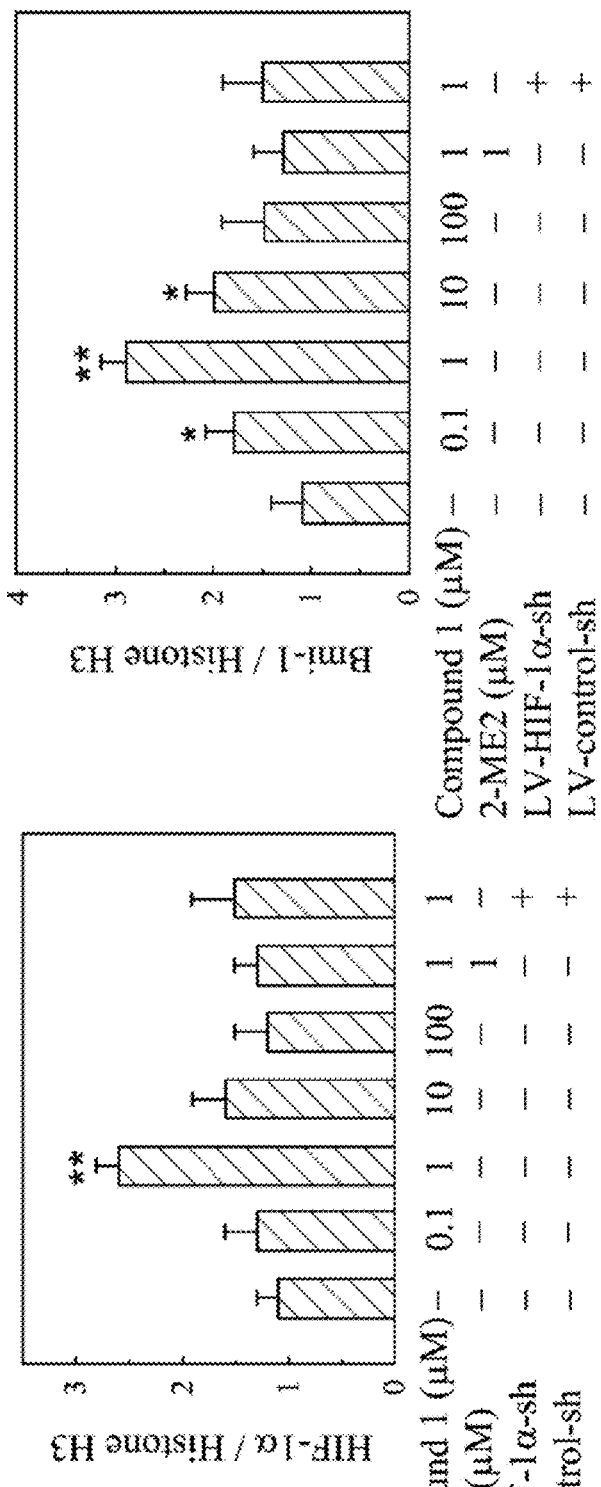
FIG. 10B shows the analytical results of the HIF-1α expressions and the Bmi-1 expressions of the NSCs exposed to the Compound 1 after inhibiting the HIF-1α expression.

In another example, the HIF-1α expressions of the NSCs are inhibited and then 1 μM of the Compound 1 is added into the medium of the NSCs. The HIF-1α expression and the Bmi-1 expressions of the NSCs are detected by the Western blot analysis. The HIF-1α expression of the NSCs is inhibited by treating the NSCs with 1 μM of the 2-ME2 for 16 hours or transducing the LV-HIF-1α-sh and the LV-control-sh into the NSCs by the lenti-viral infection. FIG. 10B shows the analytical results of the HIF-1α expressions and the Bmi-1 expressions of the NSCs exposed to the Compound 1 after inhibiting the HIF-1α expressions. The results are represented by mean±SD values; n=8 per group, wherein * represents p<0.05 compared to the control group, and ** represents p<0.01 compared to the control group. The results of FIG. 10B are consistent with the results of FIG. 10A, the HIF-1α expressions and the Bmi-1 expressions of the NSCs are increased after adding the Compound 1, in particular the 1 μM of the Compound 1. However, the enhancements of the HIF-1α expressions and the Bmi-1 expressions induced by the Compound 1 are abolished by the inhibition of the HIF-1α expressions (treated with the 2-ME2 or transduced with the LV-HIF-1α-sh).

Figure 10C:
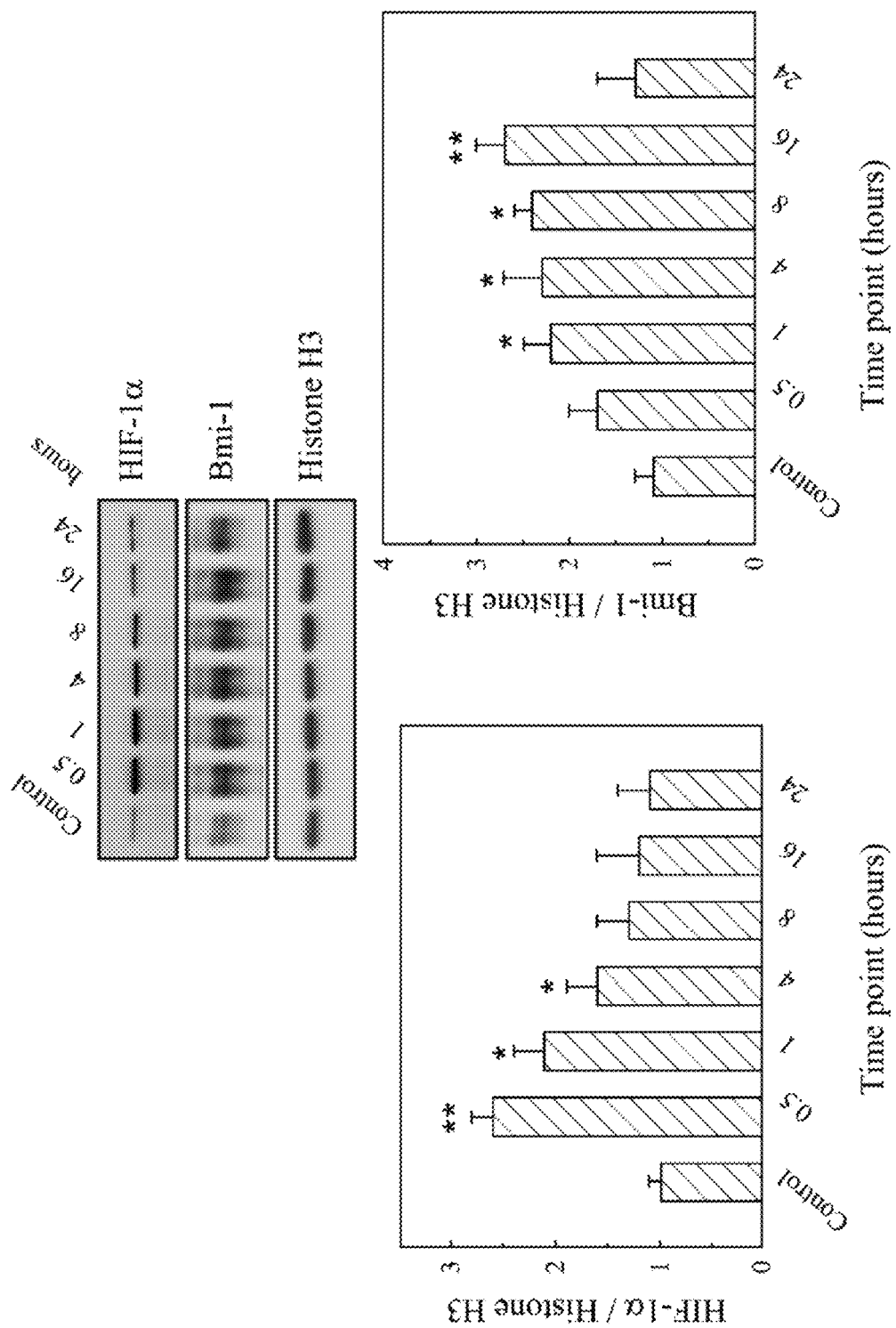
FIG. 10C shows the analytical results of the HIF-1α expressions and the Bmi-1 expressions of the NSCs exposed to the Compound 1 with different lengths of time.

In still another example, the NSCs are exposed to 1 μM of the Compound 1 and further cultured for various lengths of time (0.5 hour, 1 hour, 4 hours, 8 hours, 16 hours and 24 hours). The HIF-1α expressions and the Bmi-1 expressions of the NSCs are detected by the Western blot analysis. FIG. 10C shows the analytical results of the HIF-1α expressions and the Bmi-1 expressions of the NSCs exposed to the Compound 1 with different lengths of time. FIG. 10C shows the analytical results of the HIF-1α expressions and the Bmi-1 expressions of the NSCs exposed to the Compound 1 with different lengths of time. The results are represented by mean±SD values; n=8 per group, wherein * represents p<0.05 compared to the control group, and ** represents p<0.01 compared to the control group. In FIG. 10C, the NSCs exposed to the Compound 1 for 0.5 hour express the most HIF-1α, and the HIF-1α expressions are decreased with the longer Compound 1 treatment time. In contrast, the Bmi-1 expressions are increased with the longer Compound 1 treatment time, and the NSCs exposed to the Compound 1 for 16 hours express the most Bmi-1. These results indicate that the Compound 1 induces upregulations of the HIF-1α and the Bmi-1 in the time-dependent manner.

ii. The Effect of the Compound 1 on the Proliferation of the NSCs In Vitro

To analyze whether he Compound 1 modulates the NSCs proliferation, this example examines the effect of the HIF-1α-Bmi-1 pathway on the self-renewal of the neurosphere. To examine proliferation potentials of the NSCs, the NSCs are labelled by 25 μM of carboxyfluorescein succinimidyl ester (CFSE, Invitrogen). After 5 days of incubation, CFSE profiles are evaluated by flowcytometry (FACSCalibur, BD) and the proliferation index (PI) is calculated using MODFIT software (Verity Software House, ME) as previously described (Nature Protocols 2007; 2:2057-2067; STEM CELLS 2011; 29:2062-2076). The higher proliferation index represents the better proliferation potential. The NSCs are exposed to the various dosages of the Compound 1 (0.1 μM, 1 μM and 10 μM) for 16 hours to observe the effect of the Compound 1 on the proliferation of the NSCs. The NSCs without exposed to the Compound 1 are used as the control group.

Figure 11B:
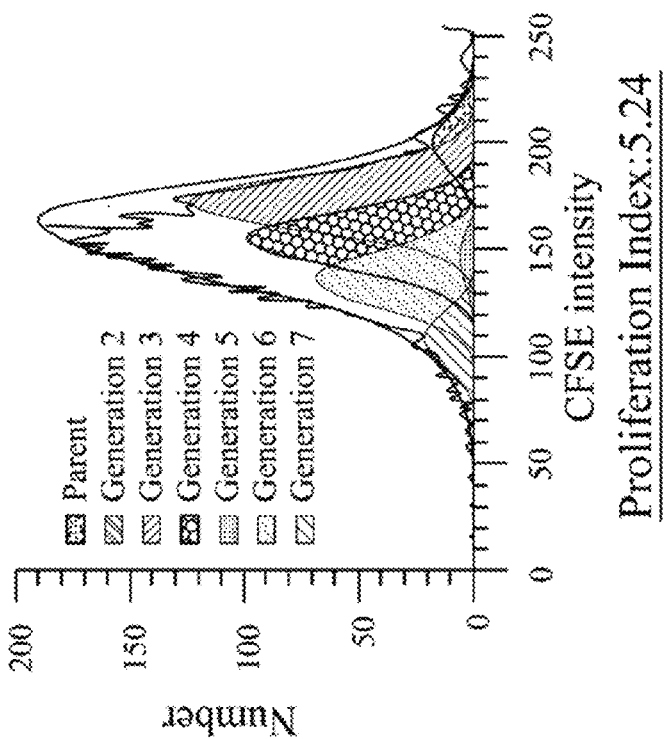
FIG. 11B shows the analytical result of the PI measurement of the NSCs exposed to 0.1 μM of the Compound 1.
Figure 11A:
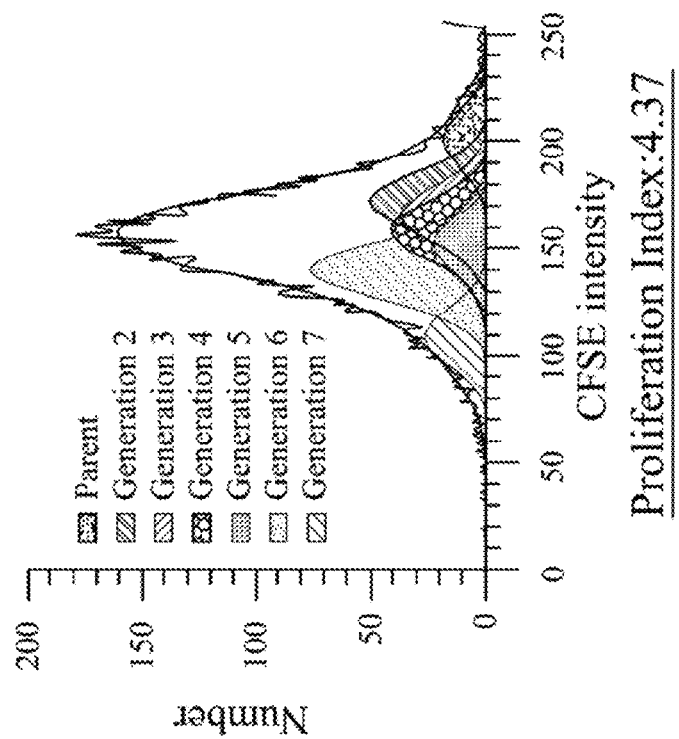
FIG. 11A shows an analytical result of a proliferation index (PI) measurement of the control group.
Figure 11D:
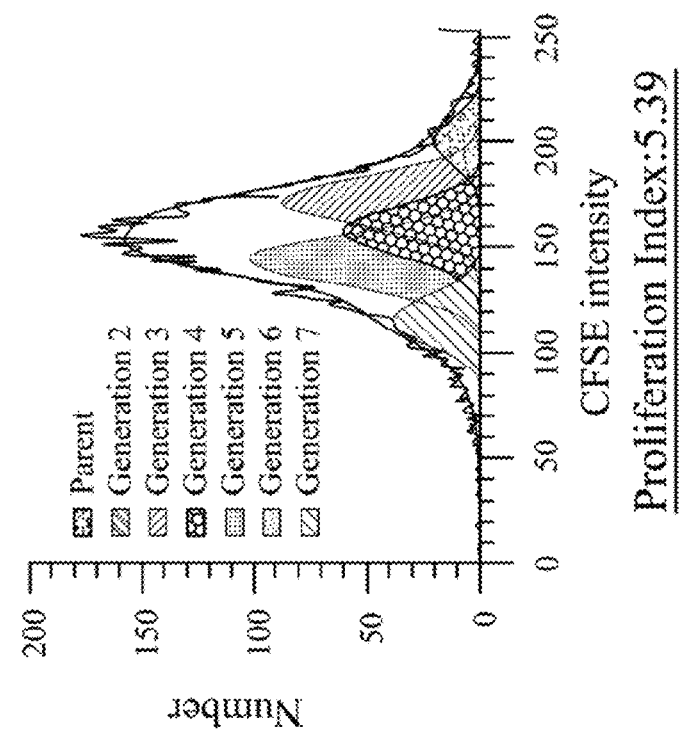
FIG. 11D shows the analytical result of the PI measurement of the NSCs exposed to 10 μM of the Compound 1.
Figure 11C:
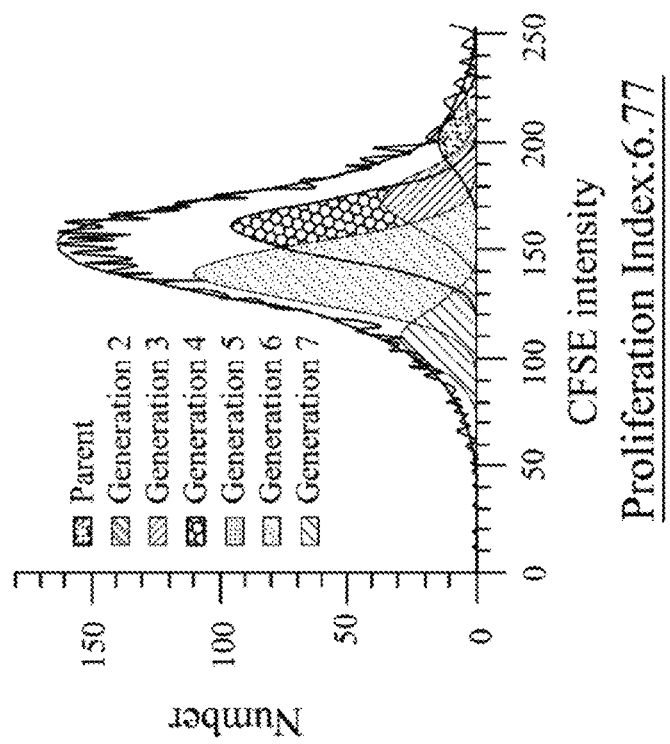
FIG. 11C shows the analytical result of the PI measurement of the NSCs exposed to 1 μM of the Compound 1.

FIG. 11A shows the analytical result of a PI measurement of the control group. FIG. 11B shows the analytical result of the PI measurement of the NSCs exposed to 0.1 μM of the Compound 1. FIG. 11C shows the analytical result of the PI measurement of the NSCs exposed to 1 μM of the Compound 1. FIG. 11D shows the analytical result of the PI measurement of the NSCs exposed to 10 μM of the Compound 1. In FIGS. 11A to 11D, the administration the Compound 1 can promote the proliferation of the NSCs. In particular, the PI of the NSCs exposed to 1 μM of the Compound 1 is increase from 4.37 to 6.77.

Figure 11E:
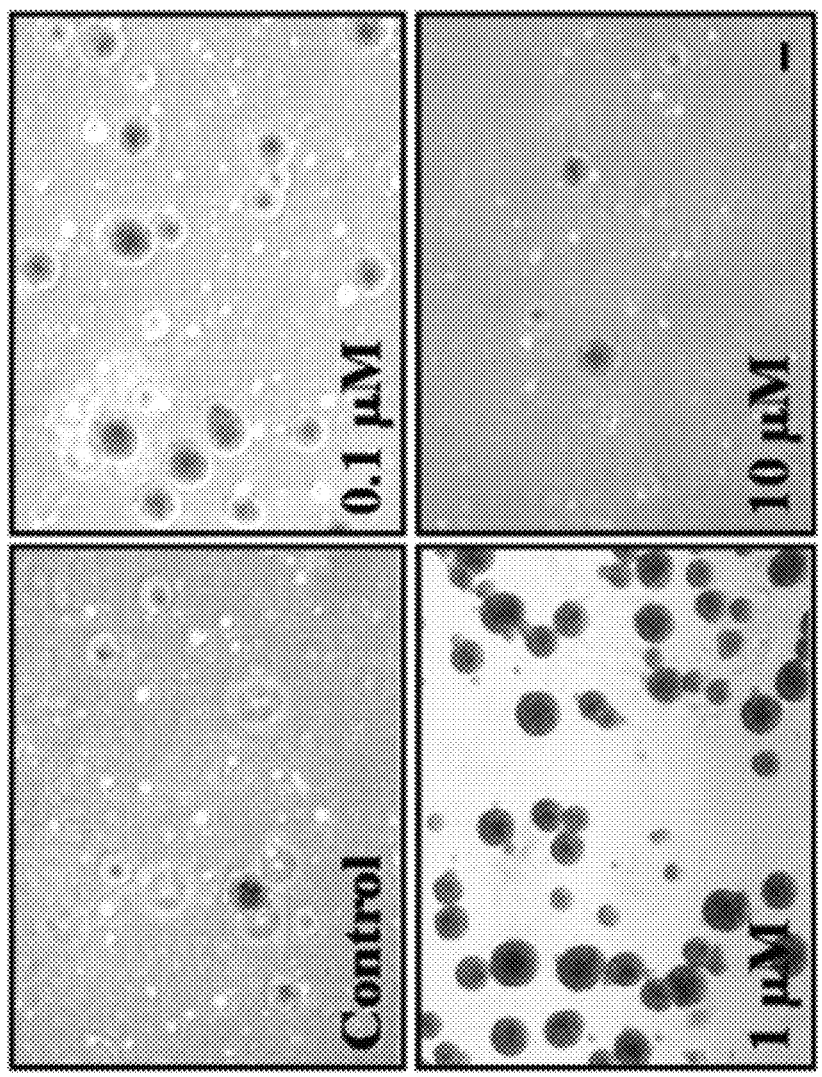
FIG. 11E shows micrographs of the neurosphere formation of the NSCs treated with different dosages of the Compound 1.

FIG. 11E shows the micrographs of the neurosphere formation of the NSCs treated with different dosages of the Compound 1 (0.1 μM, 1 μM and 10 μM), wherein the scales bar represents 50 μm. The results of FIG. 11E are consistent with the results of FIGS. 11A to 11D; the administration of the Compound 1 can promote the neurosphere formation of the NSCs, in particular the NSCs treated with 1 μM of the Compound 1.

In another example, the NSCs are treated with different dosages of the Compound 1 (0.1 μM, 1 μM and 10 μM) for 16 hours, wherein the NSCs treated with 1 μM of the Compound 1 are further transduced with the LV-Bmi-1-sh or LV-HIF-1α-sh respectively. Then the NSCs are cultured in the neurosphere culture to observe the frequency of the neurosphere formation, the self-renewal potential of the NSCs and the neurosphere size. The cells used in this example are the NSCs prepared form normal mice, the Bmi-1 knockout mice (Bmi-1$^{-/-}$) and the NL mice.

Figure 11F:
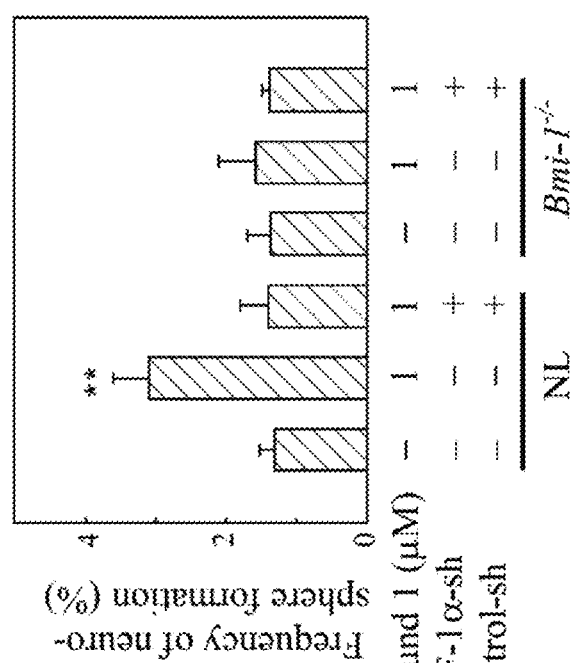
FIG. 11F is the quantitative diagram of the frequency of the neurosphere formation of the NSCs treated with different dosages of the Compound 1.
Figure 11F:
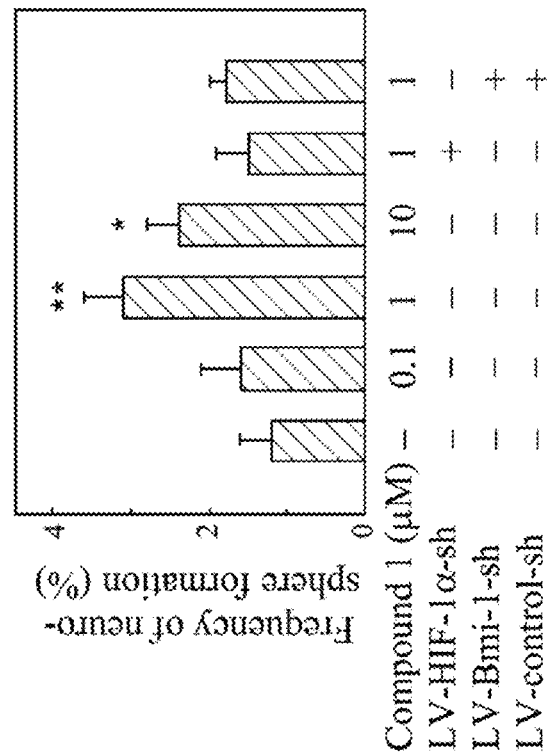
Figure 11G:
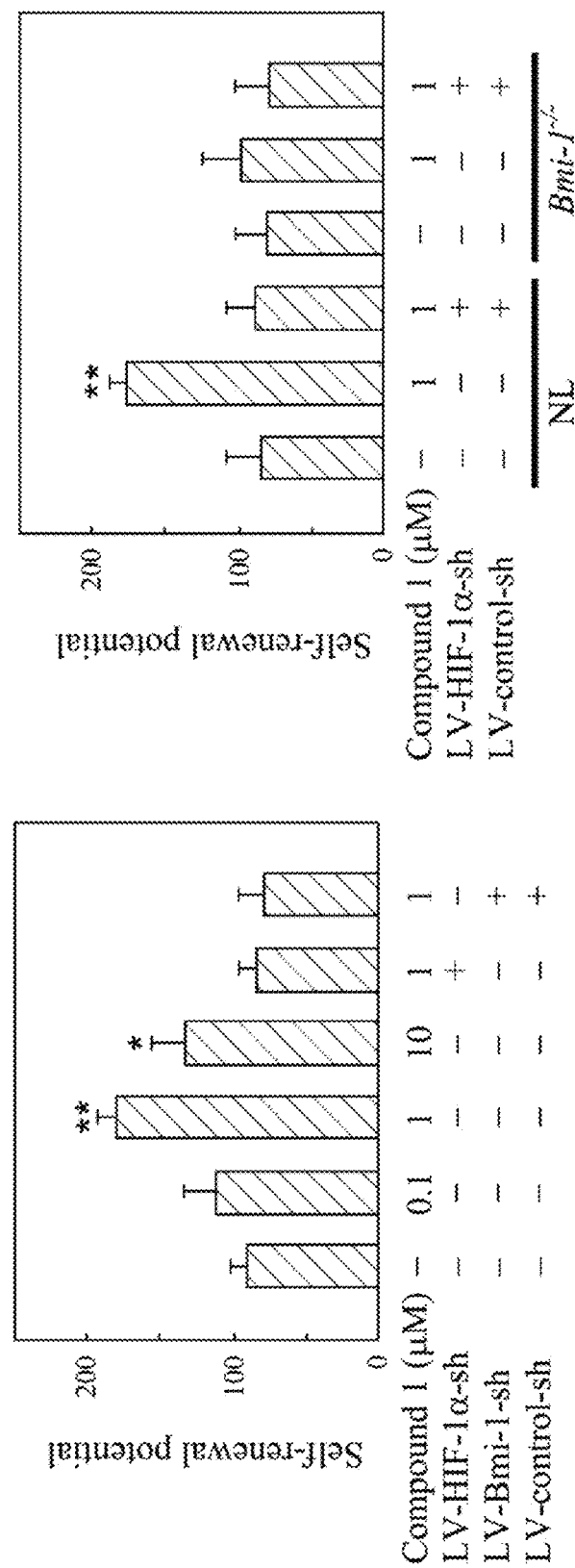
FIG. 11G is the quantitative diagram of self-renewal potential of the NSCs treated with different dosages of the Compound 1.
Figure 11H:
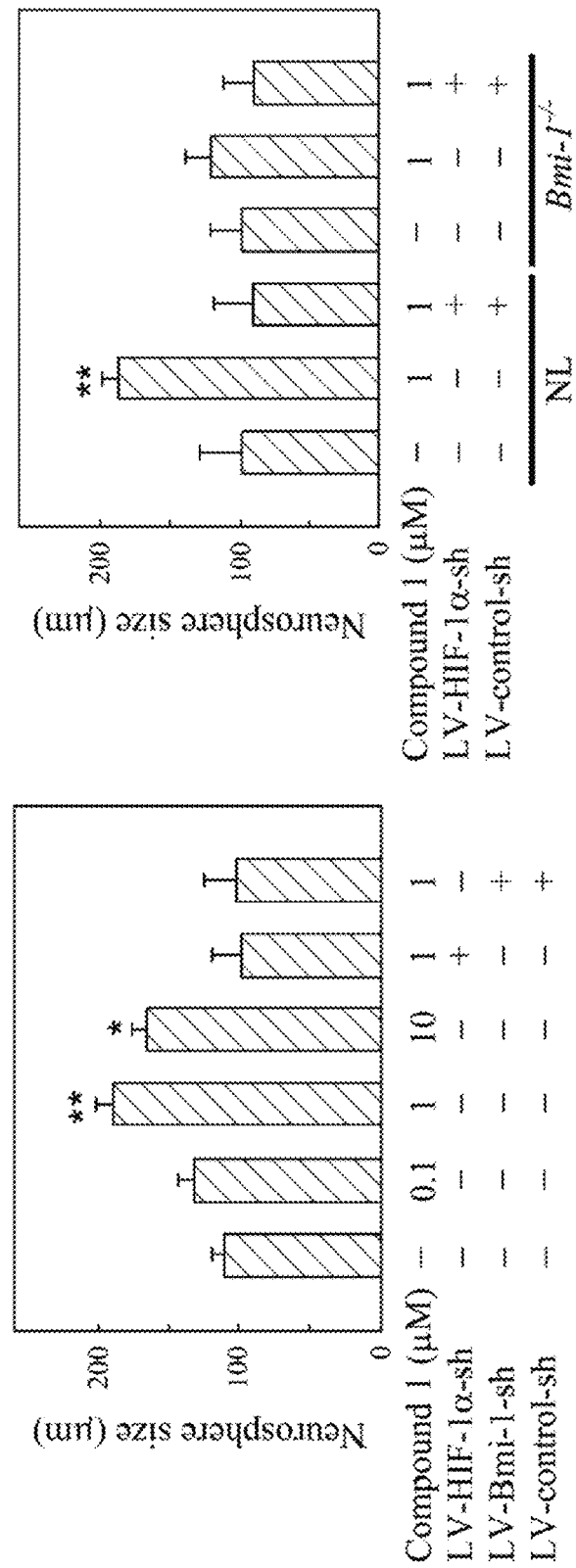
FIG. 11H is the quantitative diagram of the neurosphere size of the NSCs treated with different dosages of the Compound 1.

FIG. 11F is the quantitative diagram of the frequency of the neurosphere formation of the NSCs treated with different dosages of the Compound 1. FIG. 11G is the quantitative diagram of the self-renewal potential of the NSCs treated with different dosages of the Compound 1. FIG. 11H is the quantitative diagram of the neurosphere size of the NSCs treated with different dosages of the Compound 1. The results are represented by mean±SD values; n=8 per group, wherein * represents p<0.05 compared to the normal control, and ** represents p<0.01 compared to the normal control. In FIGS. 11F to 11G, the administration of the Compound 1 stimulates a significantly higher frequency of the neurosphere formation, more self-renewal potential and larger neurosphere size than the control group, especially the NSCs treated with 1 μM of the Compound 1. This result indicates that the Compound 1 promotes the proliferation of the NSCs in the dose-dependent manner. Conversely, gene knockout and gene knockdown by the LV-HIF-1α-sh or the LV-Bmi-1-sh into the culture inhibit all the proliferation effect on the NSCs.

To measure the effect of the administration of the Compound 1 on proliferation marker expressions of the NSCs, the NSCs treated with the Compound 1 are detected by the immunofluorescence staining. The NSCs are treated with different dosages of the Compound 1 (0.1 μM, 1 μM and 10 μM) for 16 hours, wherein the NSCs treated with 1 μM of the Compound 1 are further transduced with the LV-Bmi-1-sh or LV-HIF-1α-sh respectively to reduce the Bmi-1 expressions or the HIF-1α expressions. Then the NSCs are performed the immunofluorescence staining to confirm the Nestin expressions, the BrdU expressions and the ki-67 expressions for observing the proportion of the BrdU$^+$ cells and the ki-67$^+$ cells under different conditions. The cells used in this example are the NSCs prepared form normal mice, the Bmi-1 knockout mice (Bmi-1$^{-/-}$) and the NL mice.

Figure 12A:
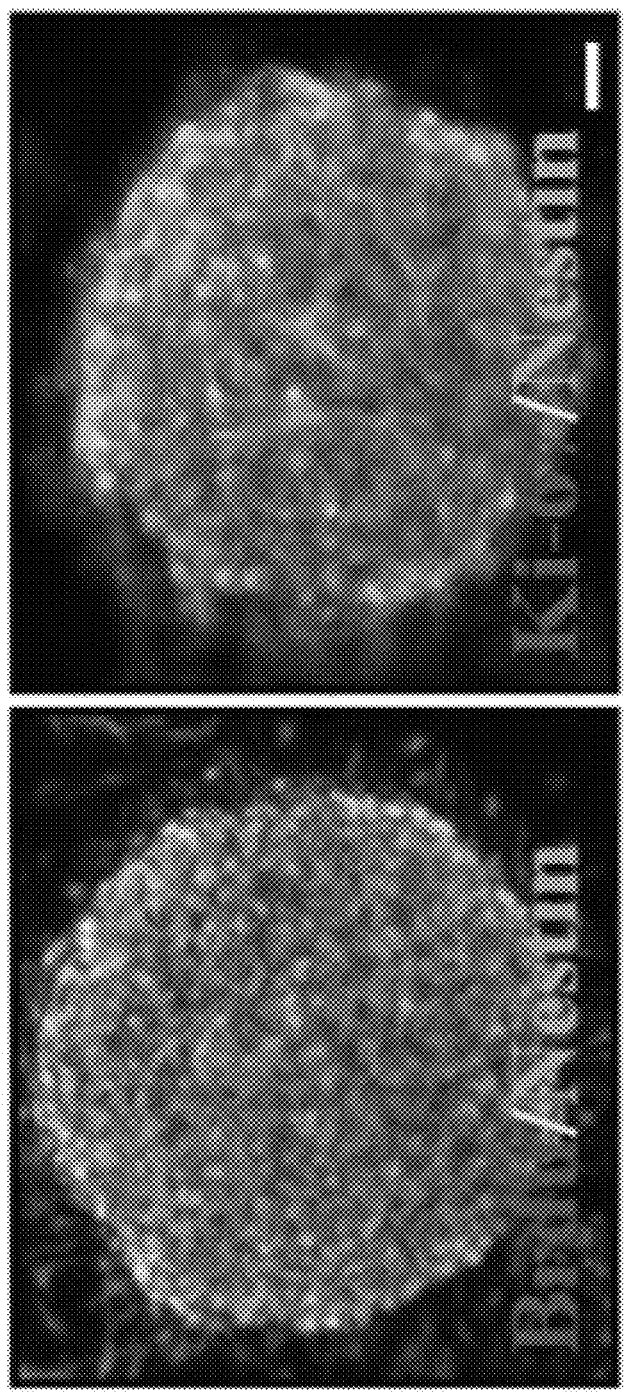
FIG. 12A shows micrographs of proliferation marker expressions of the NSCs detected by the immunofluorescence staining.
Figure 12B:
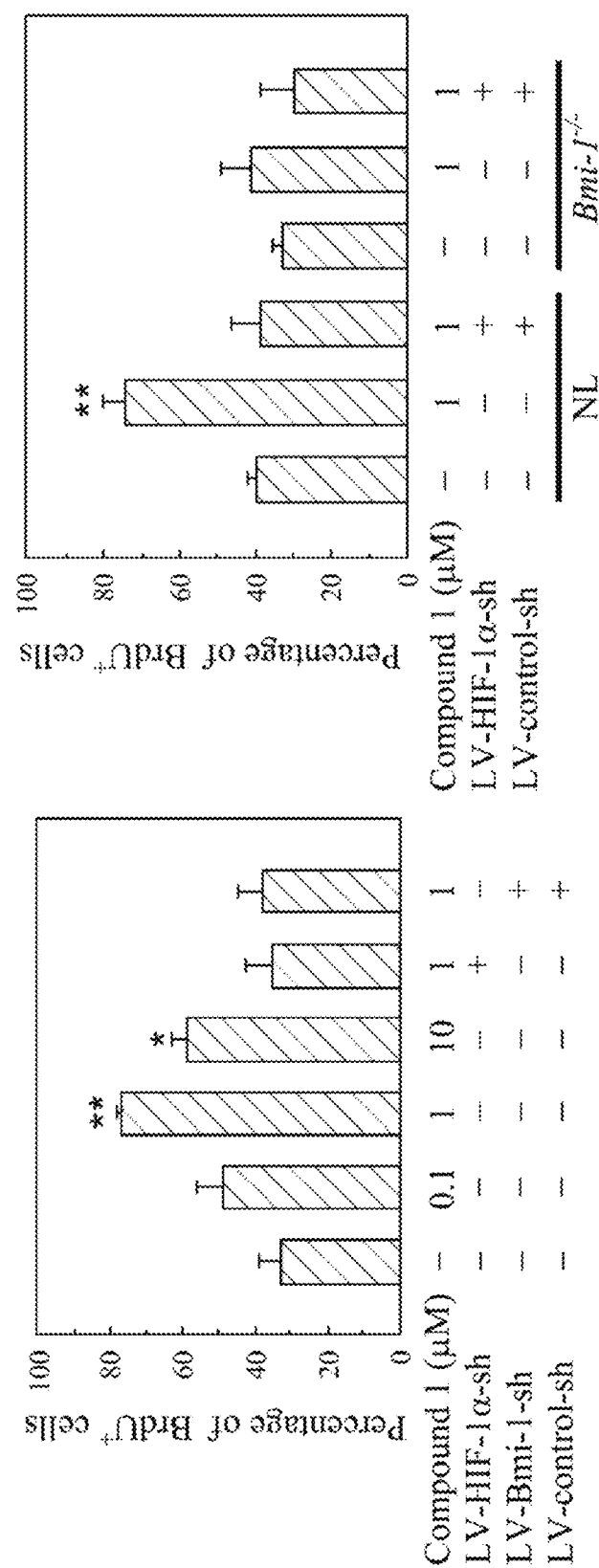
FIG. 12B is the quantitative diagram of the proportion of BrdU$^+$ cells in the neurosphere culture treated with different dosages of the Compound 1.
Figure 12C:
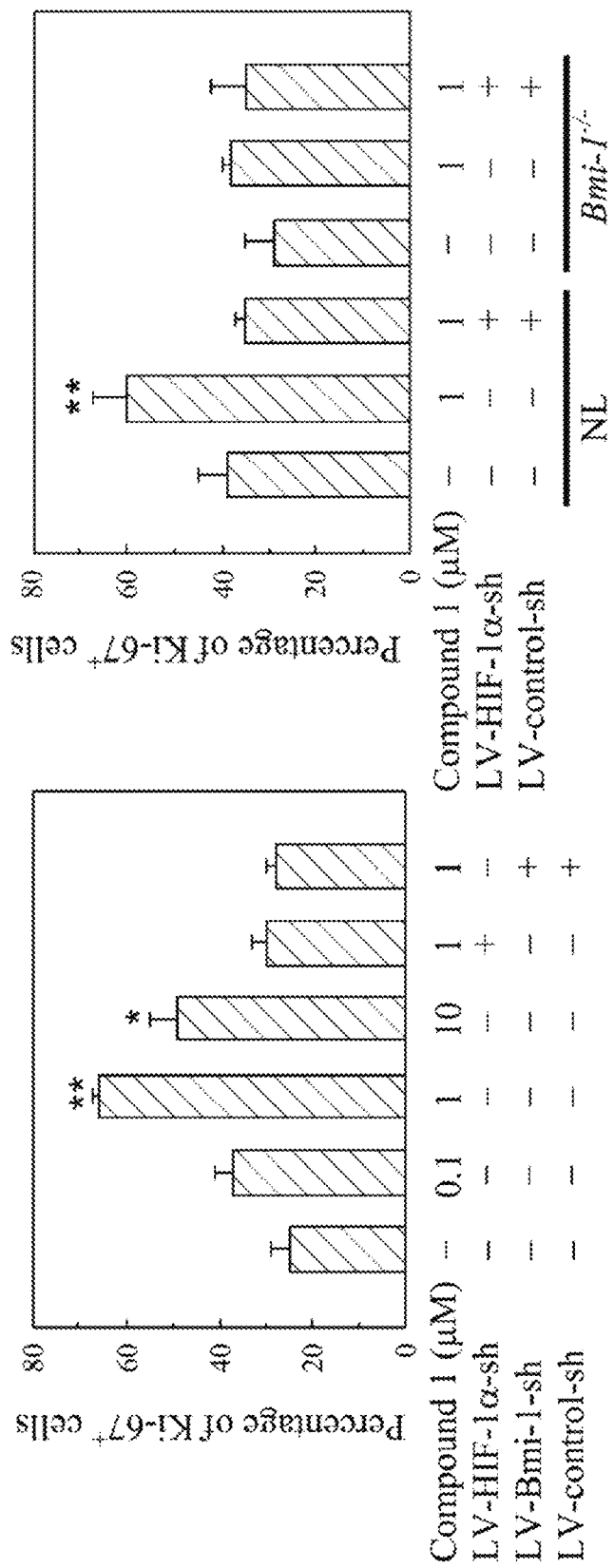
FIG. 12C is the quantitative diagram of the proportion of ki-67$^+$ cells in the neurosphere culture treated with different dosages of the Compound 1.

FIG. 12A shows the micrographs of the proliferation marker expressions of the NSCs detected by the immunofluorescence staining. FIG. 12B is the quantitative diagram of the proportion of the BrdU$^+$ cells in the neurosphere culture treated with different dosages of the Compound 1. FIG. 12C is the quantitative diagram of the proportion of the ki-67$^+$ cells in the neurosphere culture treated with different dosages of the Compound 1. The scales bar represents 50 μm. The results are represented by mean±SD values; n=8 per group, wherein * represents p<0.05 compared to the control group, and ** represents p<0.01 compared to the control group.

In FIG. 12A, the Nestin of the NSCs co-expresses with the proliferation markers (BrdU and ki-67). In FIGS. 12B and 12C, the administration of the Compound 1 increases the proportion of the BrdU$^+$ cells and the ki-67$^+$ cells, especially the NSCs treated with 1 μM of the Compound 1. These results indicate that the Compound 1 increases the proportion of the BrdU$^+$ cells and the ki-67$^+$ cells in the dose-dependent manner. However, the administrations of the LV-HIF-1α-sh or the LV-Bmi-1-sh abolish the increase of the BrdU incorporation and the ki-67 immunostaining in the NSCs. These results indicate that reducing the Bmi-1 expressions and the HIF-1α expressions inhibit the proliferation effect on the NSCs.

Taken together, these data imply that the HIF-1α-Bmi-1 pathway induced by the Compound 1 could augment the proliferation and the self renewal potential of NSCs in vitro.

4.2 Systemic Injection of the Compound 1 Enhanced NSC Proliferation In Vivo i. The Effect of the Compound on the HIF-1α Expressions and the Bmi-1 Expressions of the NSC in the Brains of the Ischemic Rats In order to study the self-renewal effect on the NSCs by the Compound 1 treatment, this example first examines whether the Compound 1 administration upregulates the HIF-1α expressions and the Bmi-1 expressions in the brains of the ischemic rats.

The ischemia-reperfusion model is established as described above. The ischemic rats are injected intraperitonealy with different dosages of the Compound 1 (0.1 mg/kg, 1 mg/kg and 10 mg/kg) at 4 hours after MCA ligation for three consecutive days. Sham rats undergo same protocol with the exception of the ligation of the bilateral CCAs and the right MCA. The rats only injected a vehicle are used as the control. The ischemic rats are decapitated at 4 hours, 16 hours, 24 hours, 36 hours and 72 hours after the Compound 1 injection. The Bmi-1 expressions and the HIF-1α expressions of the ischemic rats are detected by the Western blot analysis.

Figure 13A:
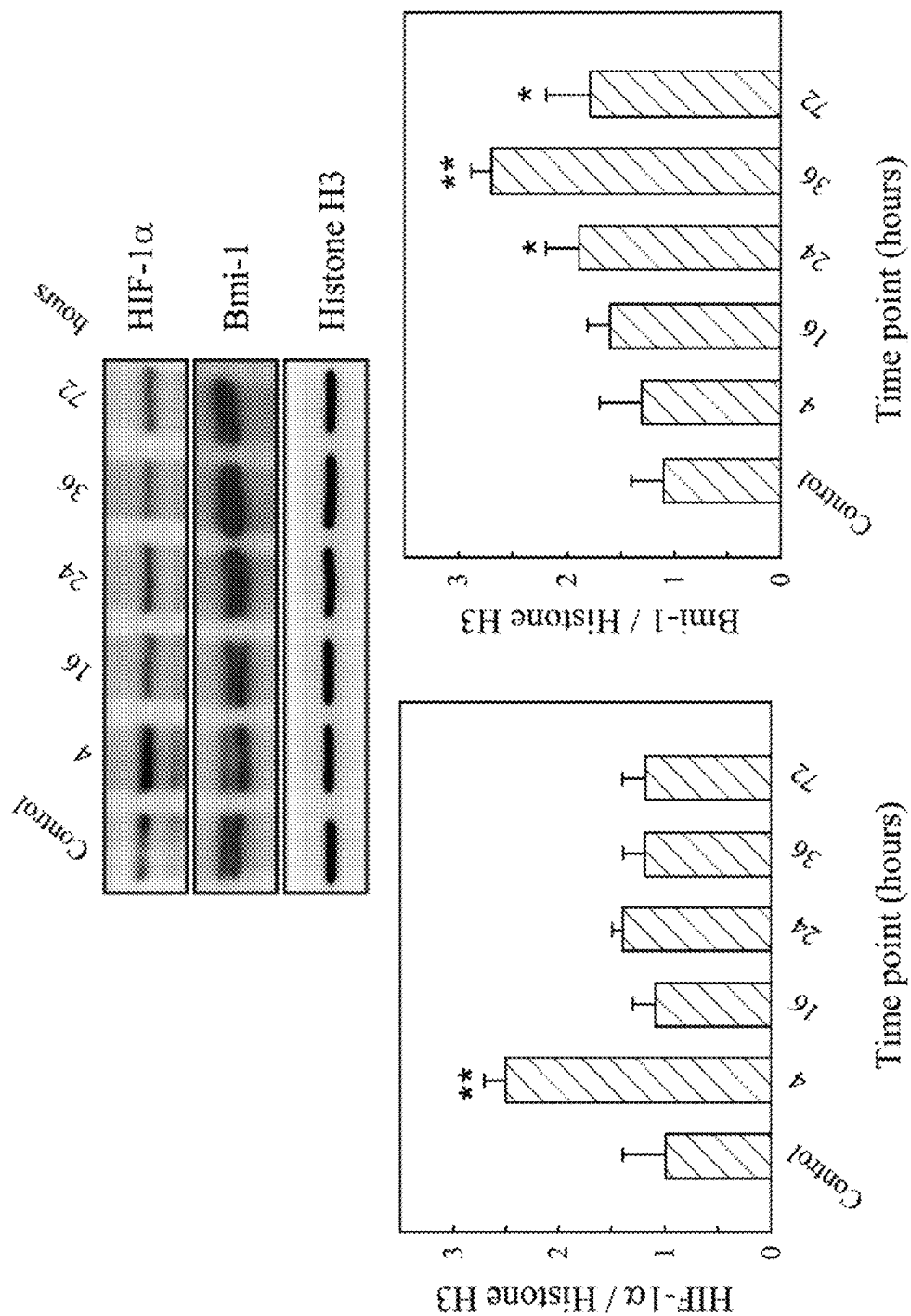
FIG. 13A shows the analytical results of the HIF-1α expressions and the Bmi-1 expressions in the brains of the ischemic rats treated with the Compound 1 with different lengths of time.
Figure 13B:
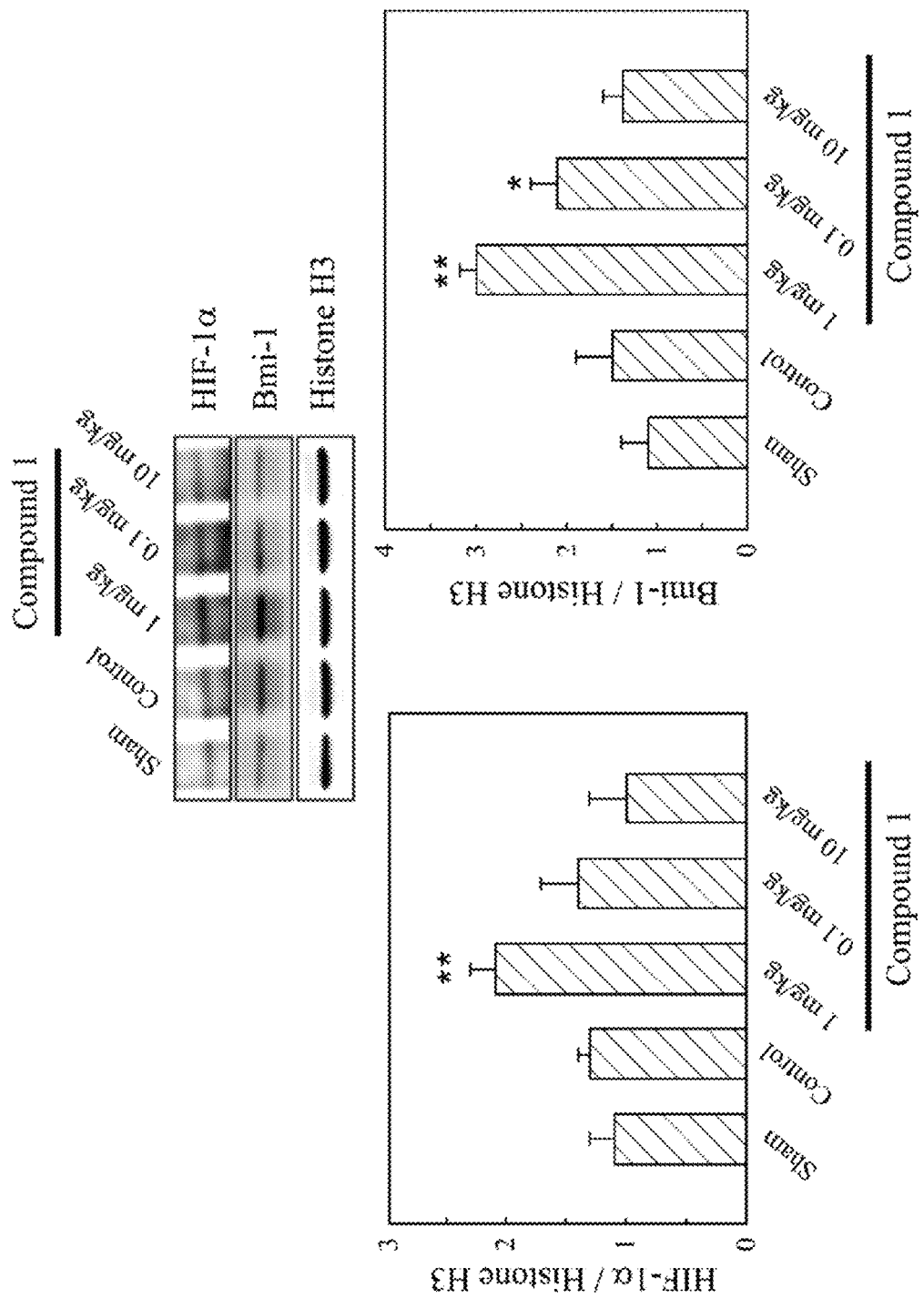
FIG. 13B shows the analytical results of the HIF-1α expressions and the Bmi-1 expressions in the brains of the ischemic rats treated with different dosages of the Compound 1.

FIG. 13A shows the analytical results of the HIF-1α expressions and the Bmi-1 expressions in the brains of the ischemic rats treated with the Compound 1 with different lengths of time, wherein the dosage of the Compound 1 used is 1 mg/kg. FIG. 13B shows the analytical results of the HIF-1α expressions and the Bmi-1 expressions in the brains of the ischemic rats treated with different dosages of the Compound 1, wherein the length of time treated with the Compound 1 is 36 hours. The results are represented by mean±SD values; n=8 per group, wherein * represents $p<0.05$ compared to the control, and ** represents $p<0.01$ compared to the control. In FIGS. 13A and 13B, the ischemic rats treated with the Compound 1 for 4 hours and the ischemic rats treated with 1 mg/kg of the Compound 1 have the highest HIF-1α expression, and the ischemic rats treated with the Compound 1 for 36 hours and the ischemic rats treated with 1 mg/kg of the Compound 1 have the highest Bmi-1 expression. Therefore the administration of the Compound 1 significantly increases the HIF-1α expressions and the Bmi-1 expressions in the brains of the ischemic rats compared with the control and the sham rats with the time-dependent manner and the dose-dependent manner.

The ischemic rats are further treated with 100 mg/kg of the 2-ME2 or stereotaxic injected with the LV-Bmi-1-sh or the LV-control-sh to inhibit the HIF-1α expressions and the Bmi-1 expressions, and then the ischemic rats are treated with 1 mg/kg of the Compound 1. The effect of the administration of the Compound 1 on the Bmi-1 expressions in the brains of the ischemic rats which are reduced the Bmi-1 expressions or the HIF-1α expressions are detected by the Western blot analysis.

Figure 13C:
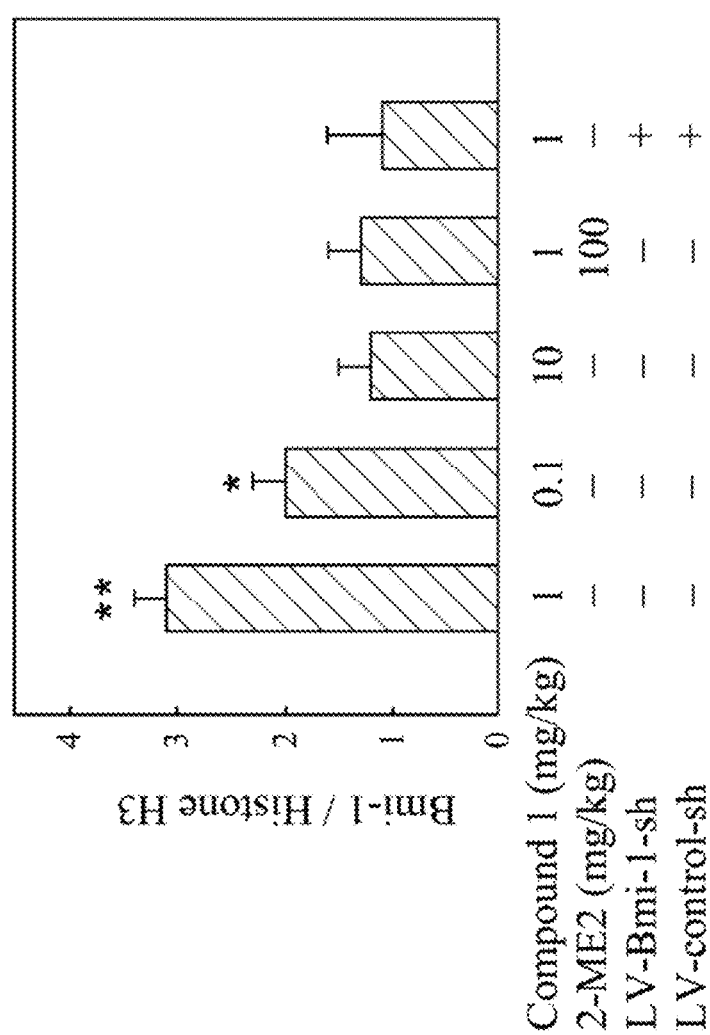
FIG. 13C shows the analytical results of the Bmi-1 expressions in the brains of the ischemic rats which are treated with the Compound 1 after reducing the Bmi-1 expressions or the HIF-1α expressions.

FIG. 13C shows the analytical results of the Bmi-1 expressions in the brains of the ischemic rats which are treated with the Compound 1 after reducing the Bmi-1 expressions or the HIF-1α expressions. The results are represented by mean±SD values; n=8 per group, wherein * represents $p<0.05$ compared to the control, and ** represents $p<0.01$ compared to the control. In FIG. 13C, the administration of the Compound 1 significantly increases the Bmi-1 expressions in the brains of the ischemic rats indeed, in particular the ischemic rats treated with 1 mg/kg of the Compound 1. However, increased Bmi-1 expressions by the Compound 1 treatment is inhibited by pharmacological HIF-1α inhibitor 2-ME2 or intracerebral injection of the LV-Bmi-1-sh.

To further prove that the Compound 1 injection enhances the proliferative ability of the NSCs, the ischemic rats are treated with different dosages of the Compound 1 (0.1 mg/kg, 1 mg/kg and 10 mg/kg) and then the brain tissues of the ischemic rats are performed the immunofluorescence staining to detect the Bmi-1 expressions (labelled by the Nestin) of the NSCs in the SVZ and the DG of the brains of the ischemic rats. Another group of the ischemic rats are inhibited the Bmi-1 expressions and the HIF-1α expressions and then injected with 1 mg/kg of the Compound 1. The effect of the administration of the Compound 1 on the Bmi-1 expressions in the brains of the ischemic rats which are reduced the Bmi-1 expressions or the HIF-1α expressions are detected by the Western blot analysis. In the group which is inhibited the HIF-1α expressions in the ischemic rats, the ischemic rats are intraperitoneal injected with 100 mg/kg of the 2-ME2. In the group which is inhibited the Bmi-1 expressions in the ischemic rats, the ischemic rats are stereotaxic injected with the LV-Bmi-1-sh or the Bmi-1 knockout mice (Bmi-1$^{-/-}$) are performed the ischemia-reperfusion model. The ischemic rats stereotaxic injected with the LV-control-sh and the littermates of the Bmi-1 knockout mice are used as the control.

Figure 14A:
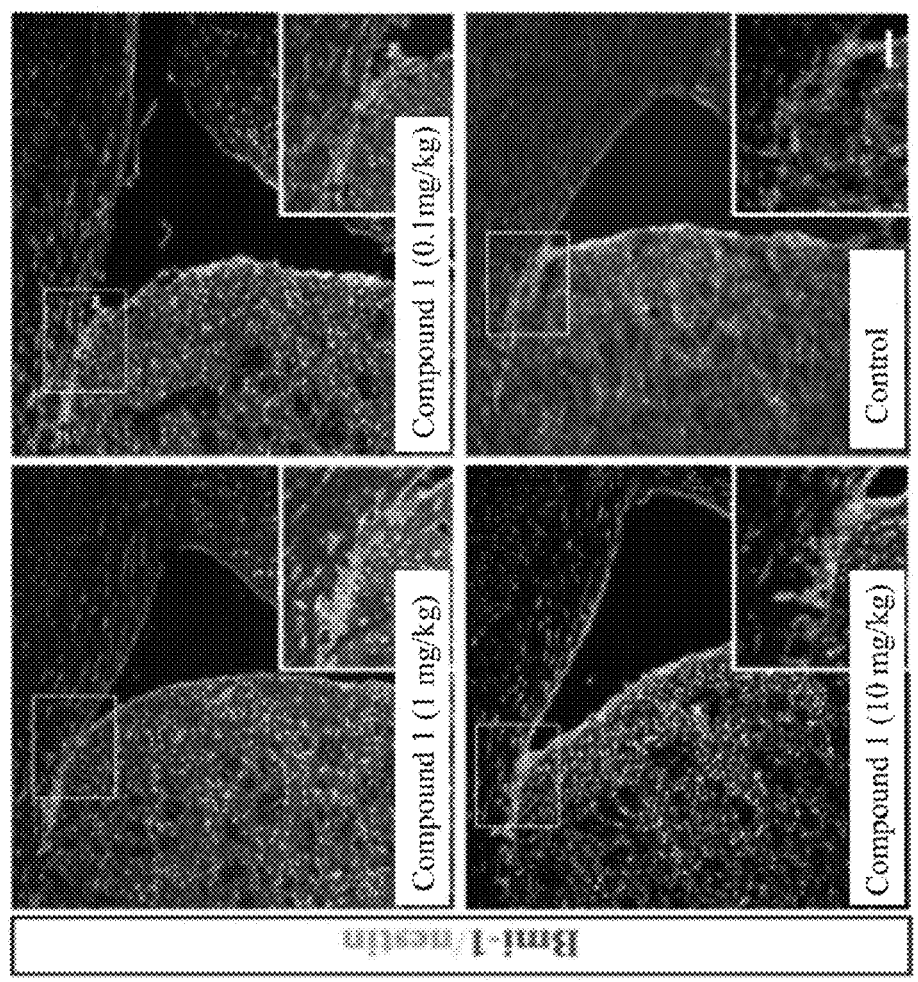
FIG. 14A shows micrographs of the Bmi-1 expressions of the NSCs it subventricular zones (SVZ) of the ischemic rats treated with different dosages of the Compound 1.
Figure 14B:
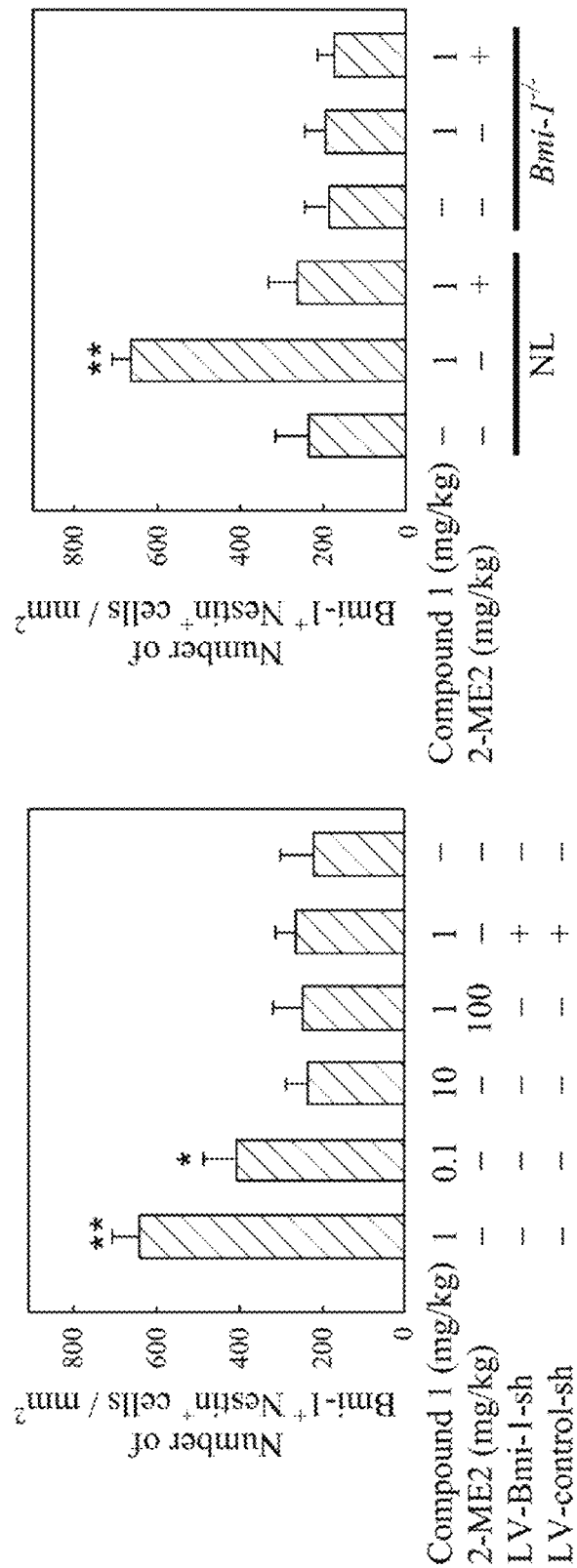
FIG. 14B shows the analytical results of the Bmi-1 expressions of the NSCs in the SVZ of the ischemic rats which are treated with the Compound 1 after reducing the Bmi-1 expressions or the HIF-1α expressions.
Figure 14C:
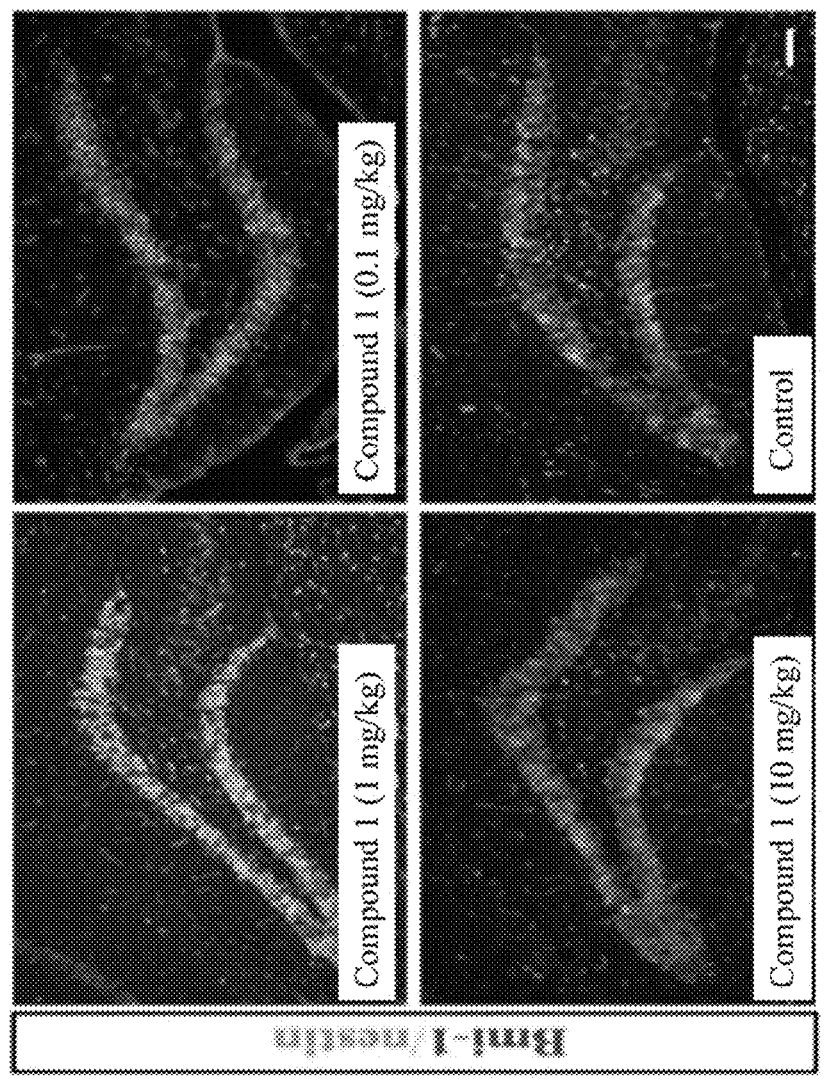
FIG. 14C shows the micrographs of the Bmi-1 expressions of the NSCs in a dentate gyrus (DG) of the ischemic rats treated with different dosages of the Compound 1.
Figure 14D:
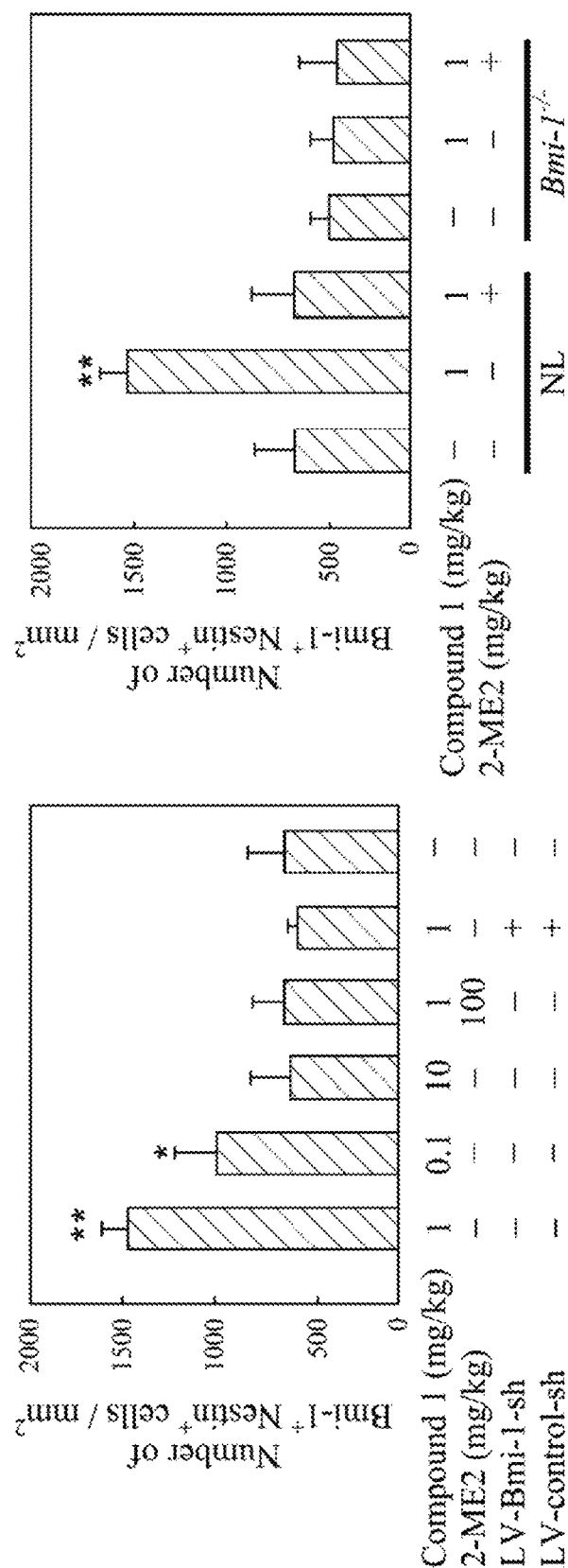
FIG. 14D shows the analytical results of the Bmi-1 expressions of the NSCs in the DG of the ischemic rats which are treated with the Compound 1 after reducing the Bmi-1 expressions or the HIF-1α expressions.

FIG. 14A shows the micrographs of the Bmi-1 expressions of the NSCs in the SVZ of the ischemic rats treated with different dosages of the Compound 1. FIG. 14B shows the analytical results of the Bmi-1 expressions of the NSCs in the SVZ of the ischemic rats which are treated with the Compound 1 after reducing the Bmi-1 expressions or the HIF-1α expressions. FIG. 14C shows the micrographs of the Bmi-1 expressions of the NSCs in the DG of the ischemic rats treated with different dosages of the Compound 1. FIG. 14D shows the analytical results of the Bmi-1 expressions of the NSCs in the DG of the ischemic rats which are treated with the Compound 1 after reducing the Bmi-1 expressions or the HIF-1α expressions. The results are represented by mean±SD values; n=8 per group, wherein * represents $p<0.05$ compared to the control, and ** represents $p<0.01$ compared to the control. The scales bar represents 50 μm. In FIGS. 14A to 14D, the administration of the Compound 1 significantly increases the number of Bmi-1$^+$Nestin$^+$ NSCs in the SVZ and the DG compared to the control, in particular the ischemic rats injected with 1 mg/kg of the Compound 1. These results indicate that the administration of the Compound 1 increases the Bmi-1 expressions of the NSCs in the dose-dependent manner. Conversely, pharmacological treatment with the 2-ME2 or the stereotaxic injection of the LV-Bmi-1-sh inhibits the Compound-1-induced enhancement of Bmi-1$^+$Nestin$^+$ NSCs numbers.

ii. The Effect of the Compound 1 on the Proliferation of the NSC in the Brain of the Ischemic Rats The ischemic rats treated with different dosages of the Compound 1 (0.1 mg/kg, 1 mg/kg and 10 mg/kg) and the ischemic rats reduced the Bmi-1 expressions or the HIF-1α expressions and then treated with 1 mg/kg of the Compound 1 are decapitated, and the brain tissues thereof are performed the immunofluorescence staining to detect the proliferation marker expressions (BrdU and ki-67) in the brains of the ischemic rats.

Figure 15A:
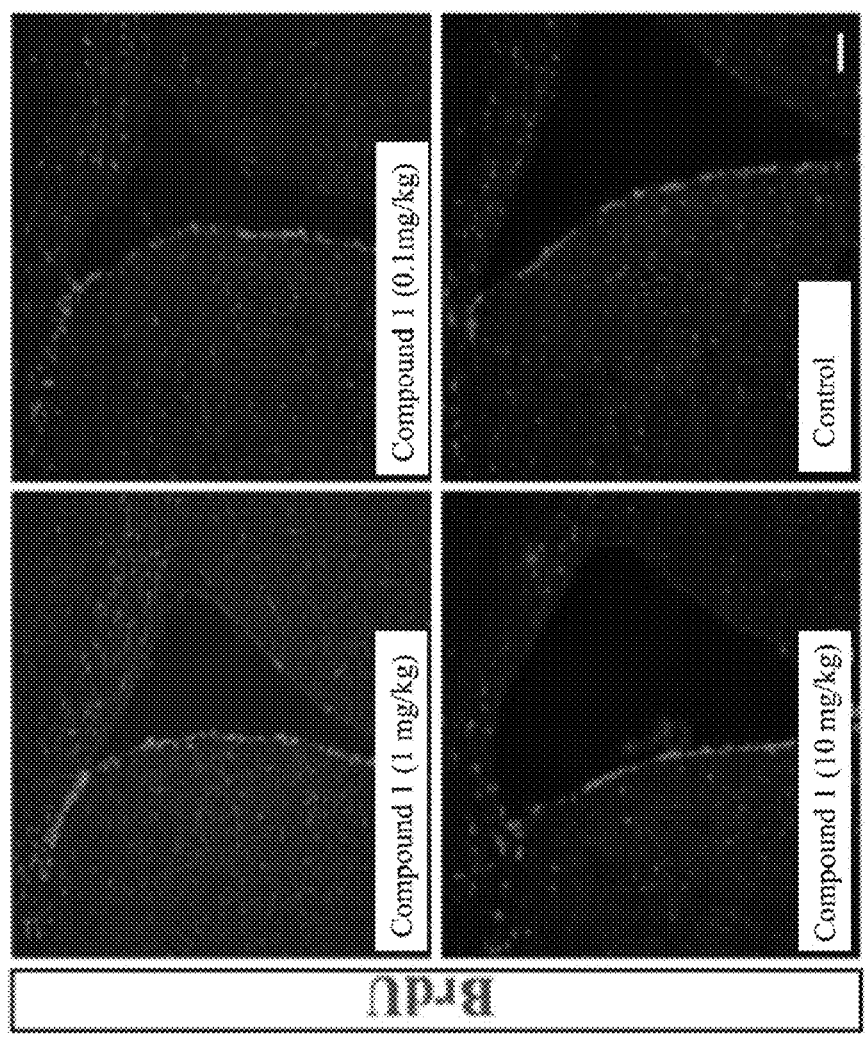
FIG. 15A shows micrographs of BrdU expressions of the SVZ of the ischemic rats treated with different dosages of the Compound 1.
Figure 15B:
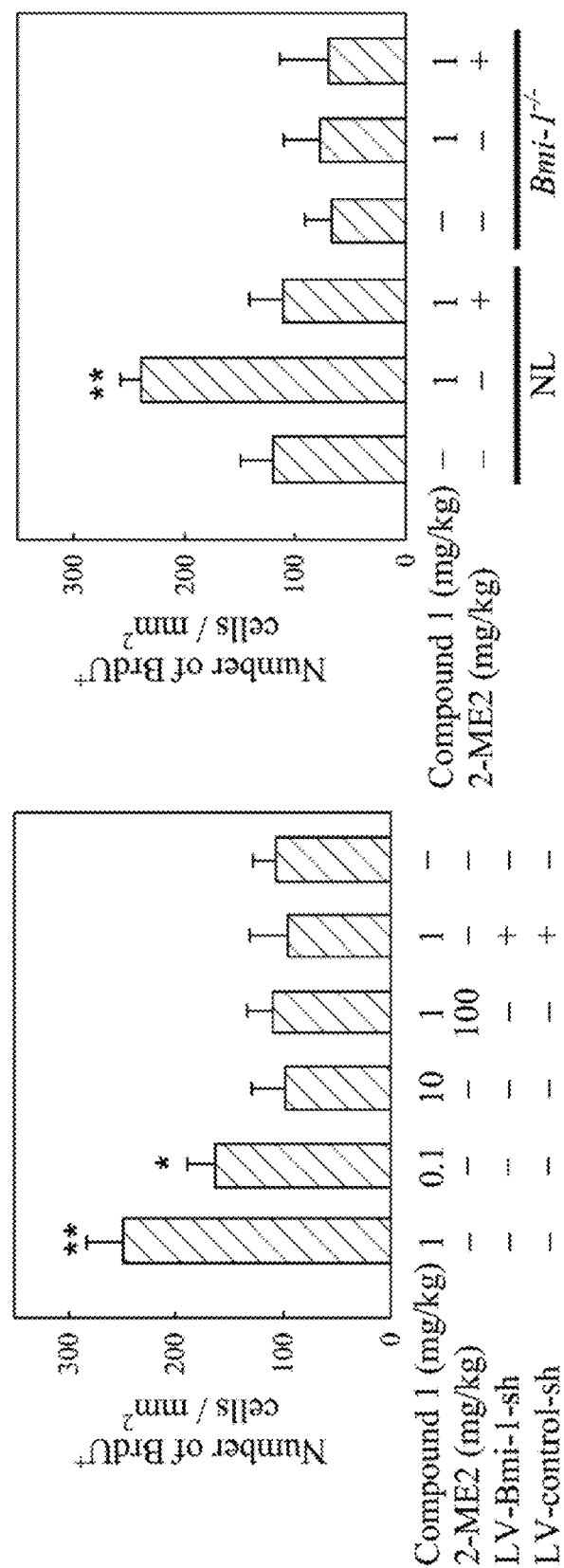
FIG. 15B is a quantitative diagram of the number of BrdU$^+$ cells in the SVZ of the ischemic rats which are treated with the Compound 1 after reducing the Bmi-1 expressions or the HIF-1α expressions.
Figure 15C:
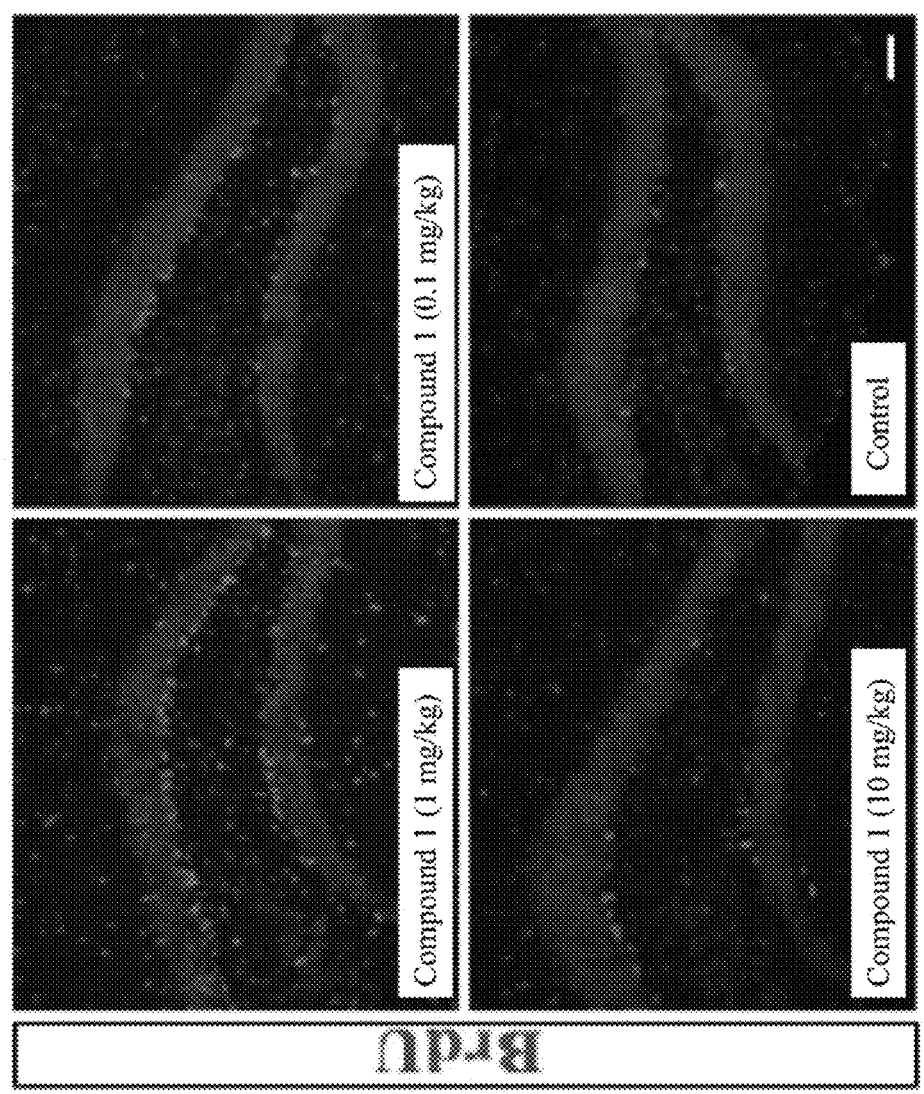
FIG. 15C shows micrographs of the BrdU expressions of the DG of the ischemic rats treated with different dosages of the Compound 1.
Figure 15D:
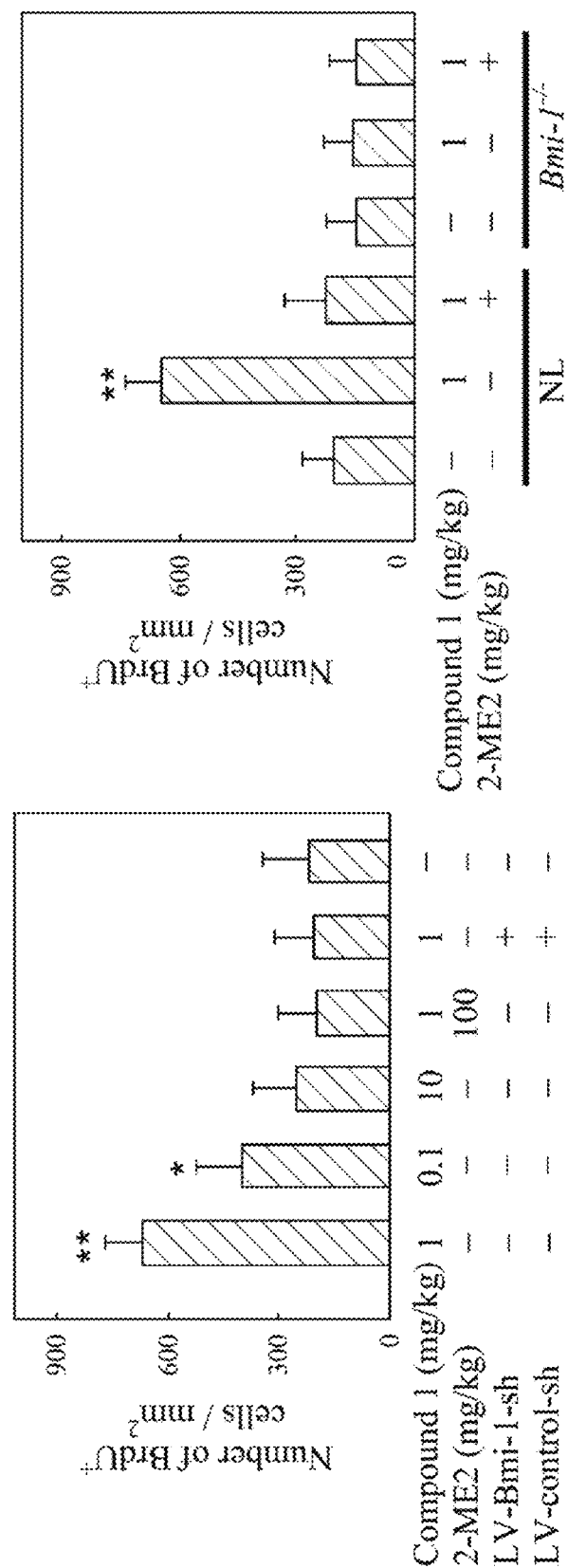
FIG. 15D is the quantitative diagram of the number of BrdU$^+$ cells in the DG of the ischemic rats which are treated with the Compound 1 after reducing the Bmi-1 expressions or the HIF-1α expressions.
Figure 15E:
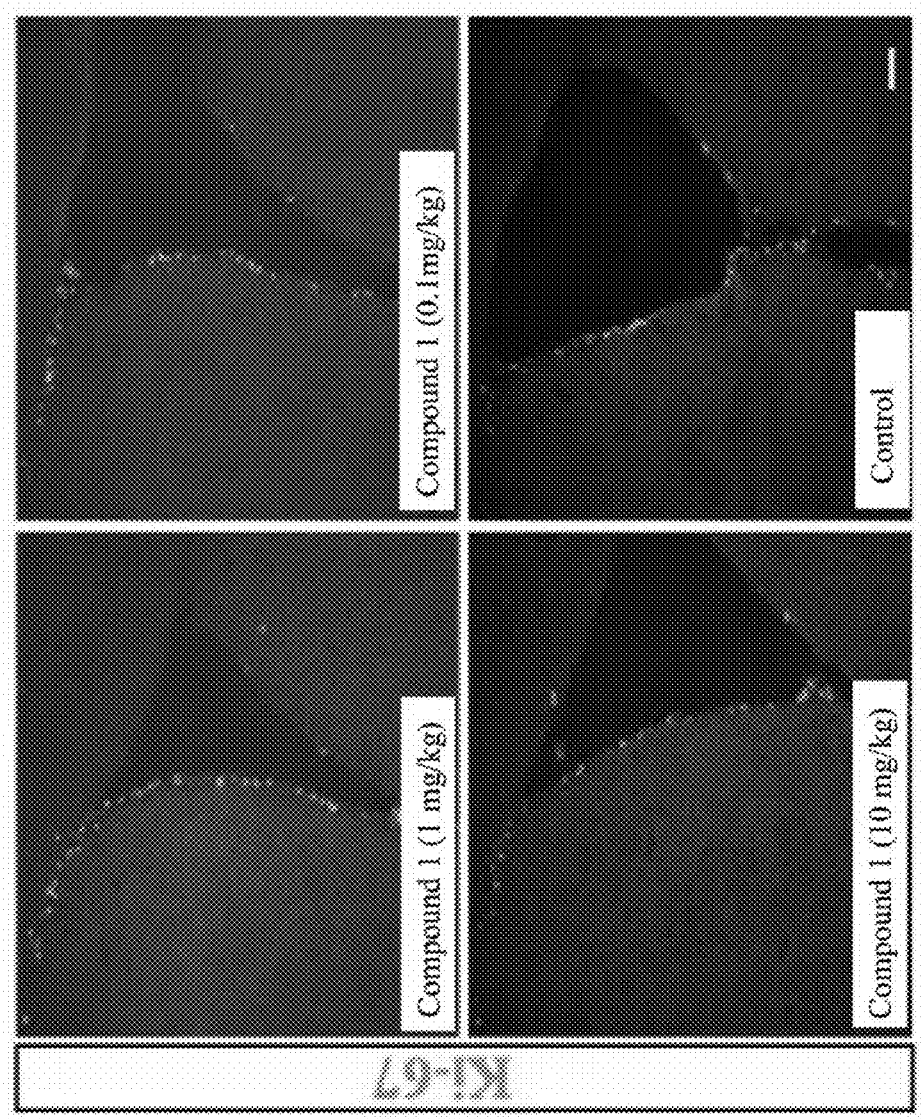
FIG. 15E shows micrographs of ki-67 expressions of the SVZ of the ischemic rats treated with different dosages of the Compound 1.
Figure 15F:
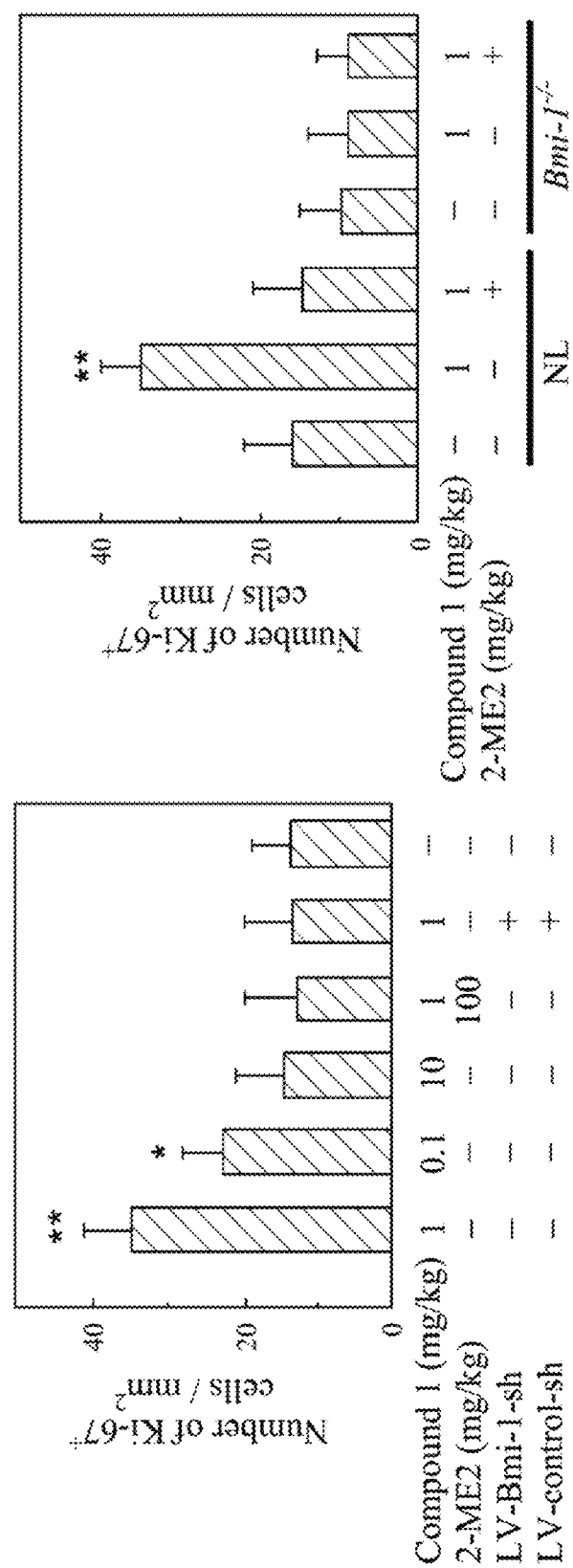
FIG. 15F is the quantitative diagram of the number of ki-67$^+$ cells in the SVZ of the ischemic rats which are treated with the Compound 1 after reducing the Bmi-1 expressions or the HIF-1α expressions.
Figure 15G:
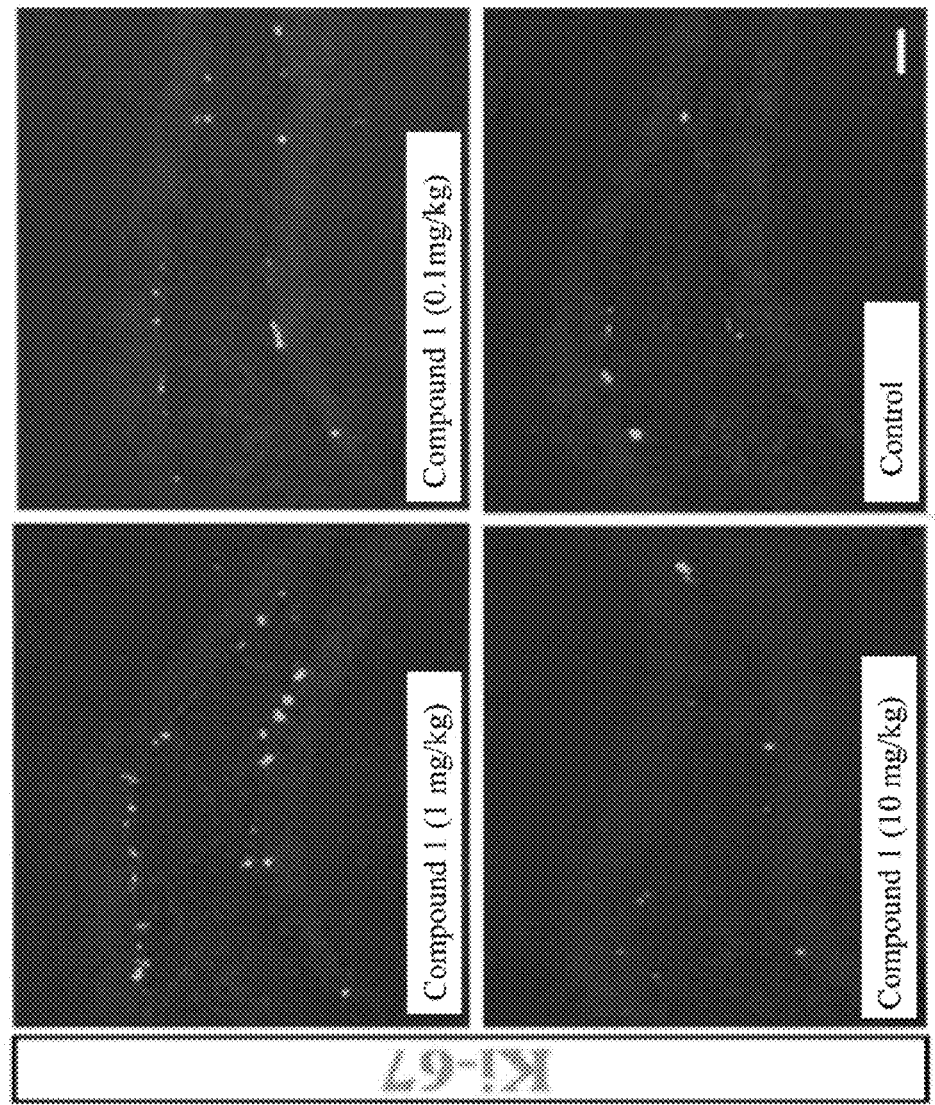
FIG. 15G shows the micrographs of the ki-67 expressions of the DG of the ischemic rats treated with different dosages of the Compound 1.
Figure 15H:
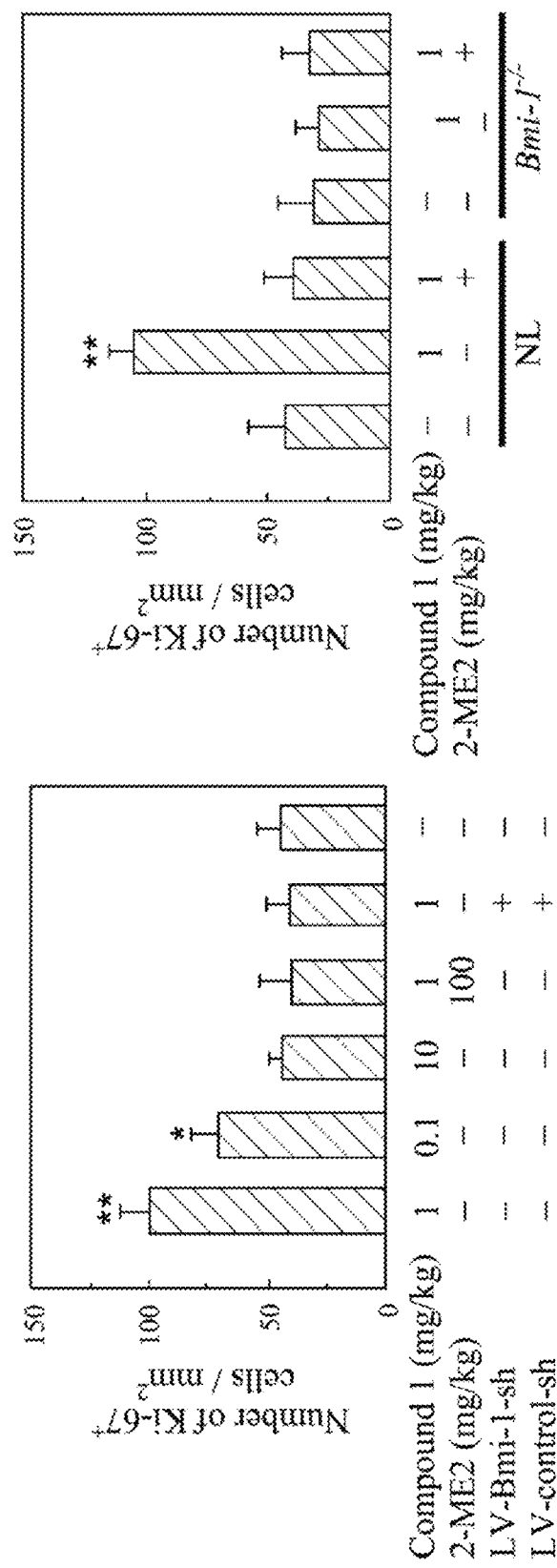
FIG. 15H is the quantitative diagram of the number of ki-67$^+$ cells in the DG of the ischemic rats which are treated with the Compound 1 after reducing the Bmi-1 expressions or the HIF-1α expressions.

FIG. 15A shows the micrographs of the BrdU expressions of the SVZ of the ischemic rats treated with different dosages of the Compound 1. FIG. 15B is the quantitative diagram of the number of BrdU$^+$ cells in the SVZ of the ischemic rats which are treated with the Compound 1 after reducing the Bmi-1 expressions or the HIF-1α expressions. FIG. 15C shows the micrographs of the BrdU expressions of the DG of the ischemic rats treated with different dosages of the Compound 1. FIG. 15D is the quantitative diagram of the number of BrdU$^+$ cells in the DG of the ischemic rats which are treated with the Compound 1 after reducing the Bmi-1 expressions or the HIF-1α expressions. FIG. 15E shows the micrographs of the ki-67 expressions of the SVZ of the ischemic rats treated with different dosages of the Compound 1. FIG. 15F is the quantitative diagram of the number of ki-67$^+$ cells in the SVZ of the ischemic rats which are treated with the Compound 1 after reducing the Bmi-1 expressions or the HIF-1α expressions. FIG. 15G shows the micrographs of the ki-67 expressions of the DG of the ischemic rats treated with different dosages of the Compound 1. FIG. 15H is the quantitative diagram of the number of ki-67$^+$ cells in the DG of the ischemic rats which are treated with the Compound 1 after reducing the Bmi-1 expressions or the HIF-1α expressions. The results are represented by mean±SD values; n=8 per group, wherein * represents $p<0.05$ compared to the control, and ** represents $p<0.01$ compared to the control. The scales bar represents 50 μm.

In FIGS. 15A to 15H, significant enhancement of numbers of BrdU$^+$ cells and ki-67$^+$ cells in the SVZ and the DG of the brains of the ischemic rats are observed in the Compound 1 injection compared to the control, in particular the ischemic rats injected with 1 mg/kg of the Compound 1. These results indicate that the administration of the Compound 1 can promote the proliferation of the cells in the brains of the ischemic rats. However, the 2-ME2 treatment or the LV-Bmi-1-sh injection abolishes the increase numbers of the BrdU$^+$ cells and the ki-67$^+$ cells in the SVZ and the DG of the brains of the ischemic rats.

In summary, these data show that the Compound-1-induced HIF-1α-Bmi-1 pathway can augment the proliferation and the self renewal potential of the NSCs.

4.3 Systemic Administration of the Compound 1 Reduced Volume of the Infarction After Cerebral Ischemia The data of aforementioned examples demonstrate that the Compound 1 can augment the proliferation and the self renewal potential of the NSCs in vitro and in vivo. The examples in this section further discuss the effect of the Compound 1 on the treatment of a brain tissue damage of a subject.

Figure 16:
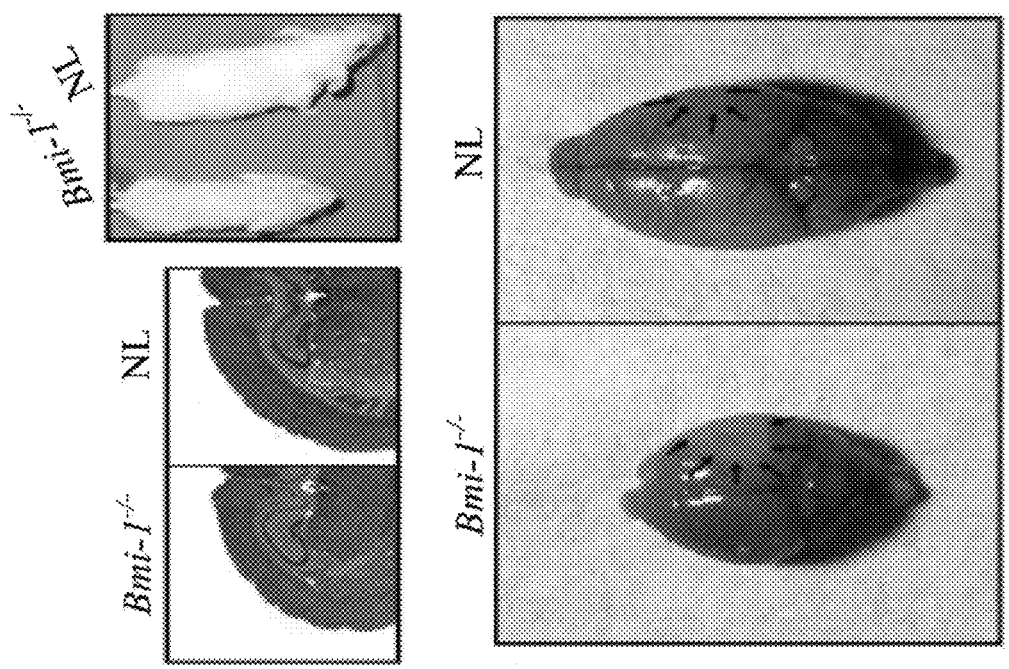
FIG. 16 are photographs showing infarction areas in the brains of an ischemic Bmi-1 knockout mouse and an ischemic NL mouse.

In attempting to emphasize that the Bmi-1 play a significant role in rescuing the brain from an ischemic injury, the Bmi-1 knockout mice (Bmi-1$^{-/-}$) and their NL are performed the ischemia-reperfusion model to compare the difference of stroke insult. At 2 days after cerebral ischemia, the mice are decapitated to obtain the brain tissues for observing infarction areas of the brains of the ischemic mice. FIG. 16 are photographs showing infarction areas in the brains of the ischemic Bmi-1 knockout mouse and the ischemic NL mouse, wherein the arrows indicate the infarction area. In FIG. 16, larger volume of infarction area is observed in the Bmi-1 knockout mouse (Bmi-1$^{-/-}$) than that in the NL mouse.

In addition, the ischemic rats are intraperitoneal injected with different dosages of the Compound 1 (0.1 mg/kg, 1 mg/kg and 10 mg/kg). The ischemic rats intraperitoneal injected with vehicle are used as the control. At 2 days after the Compound 1 treatment, the ischemic rats are intracardially perfused with PBS. The brain tissues are removed, immersed in cold PBS, and sliced into 2-mm-thick sections. The brain slices are performed triphenyltetrazolium chloride (TTC, Research Organics Inc) staining. After the TTC staining, the non-infarction area is stained dark red, and the infarction area is stained light yellow. The effect of the Compound 1 on protection the ischemic injury of the ischemic rats can be confirmed by observing the volume of the infarction.

Figure 17A:
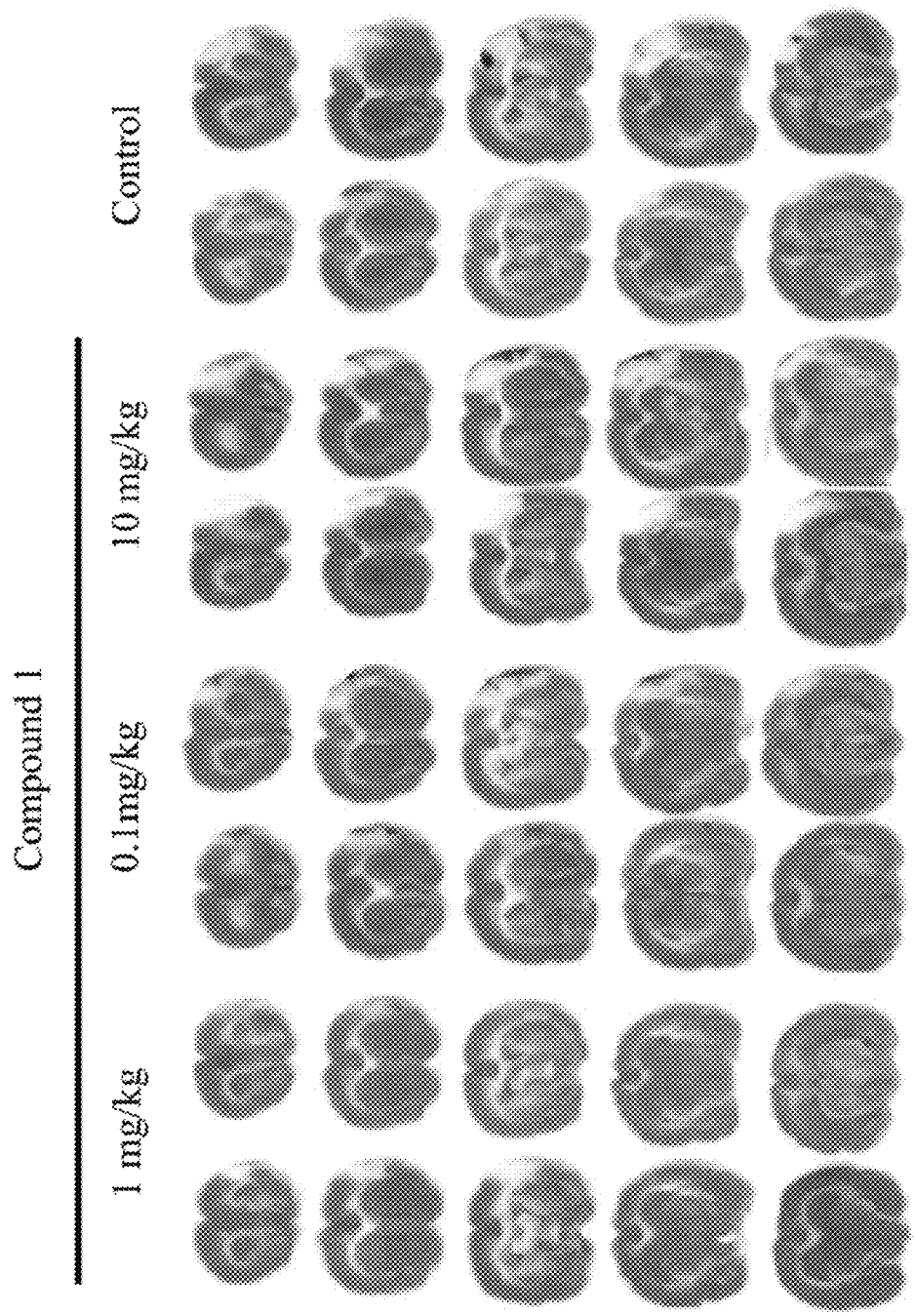
FIG. 17A are photographs showing the effect of the administration of the Compound 1 on the volume of the infarction in the brains of the ischemic rats.
Figure 17B:
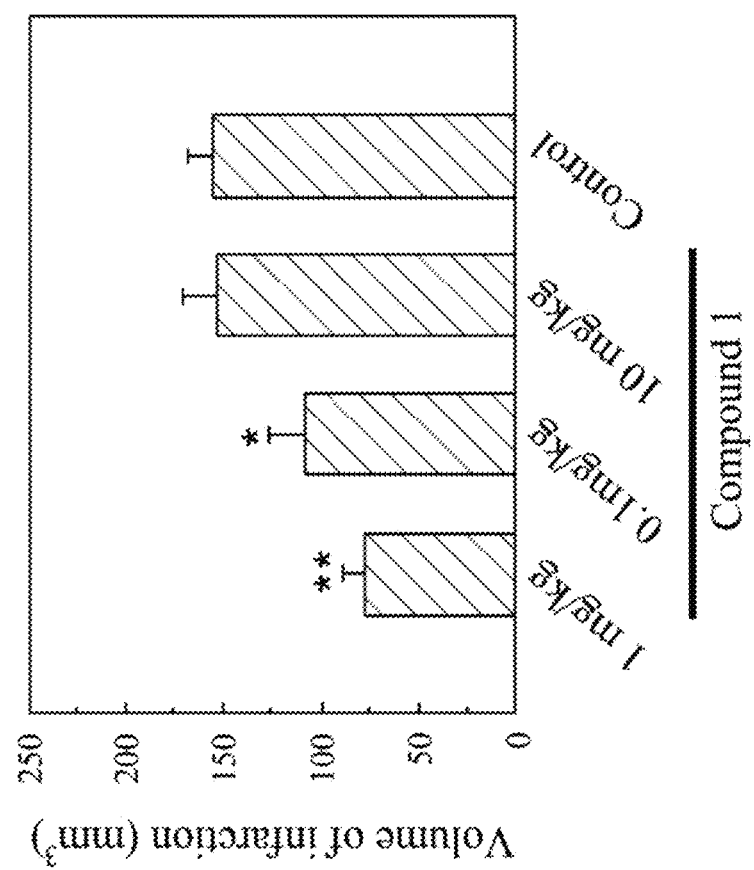
FIG. 17B is the quantitative diagram of the FIG. 17A.

FIG. 17A are the photographs showing the effect of the administration of the Compound 1 on the volume of the infarction in the brains of the ischemic rats. FIG. 17B is the quantitative diagram of the FIG. 17A. The results are represented by mean±SD values; n=8 per group, wherein * represents $p<0.05$ compared to the control, and ** represents $p<0.01$ compared to the control. In FIGS. 17A and 17B, the volume of the infarction of the ischemic rats treated with the Compound 1 is much smaller than the volume of the infarction of the control, in particular the ischemic rats treated with 1 mg/kg of the Compound 1.

Further, the ischemic rats are assigned into 5 groups, 4 test groups and 1 control group. The ischemic rats of the test groups are injected with 1 mg/kg of the Compound 1, 30 mg/kg of the genipin, 1 mg/kg of the Compound 1 and 100 mg/kg of 2-ME2, and 1 mg/kg of the Compound 1 and the LV-Bmi-1-sh, respectively. The ischemic rats of the control group are injected with the vehicle. At 7 days after the injection, the ischemic rats of the different groups are anesthetized, and the volume of the infarction thereof is assessed by a magnetic resonance imaging (MRI).

Figure 18A:
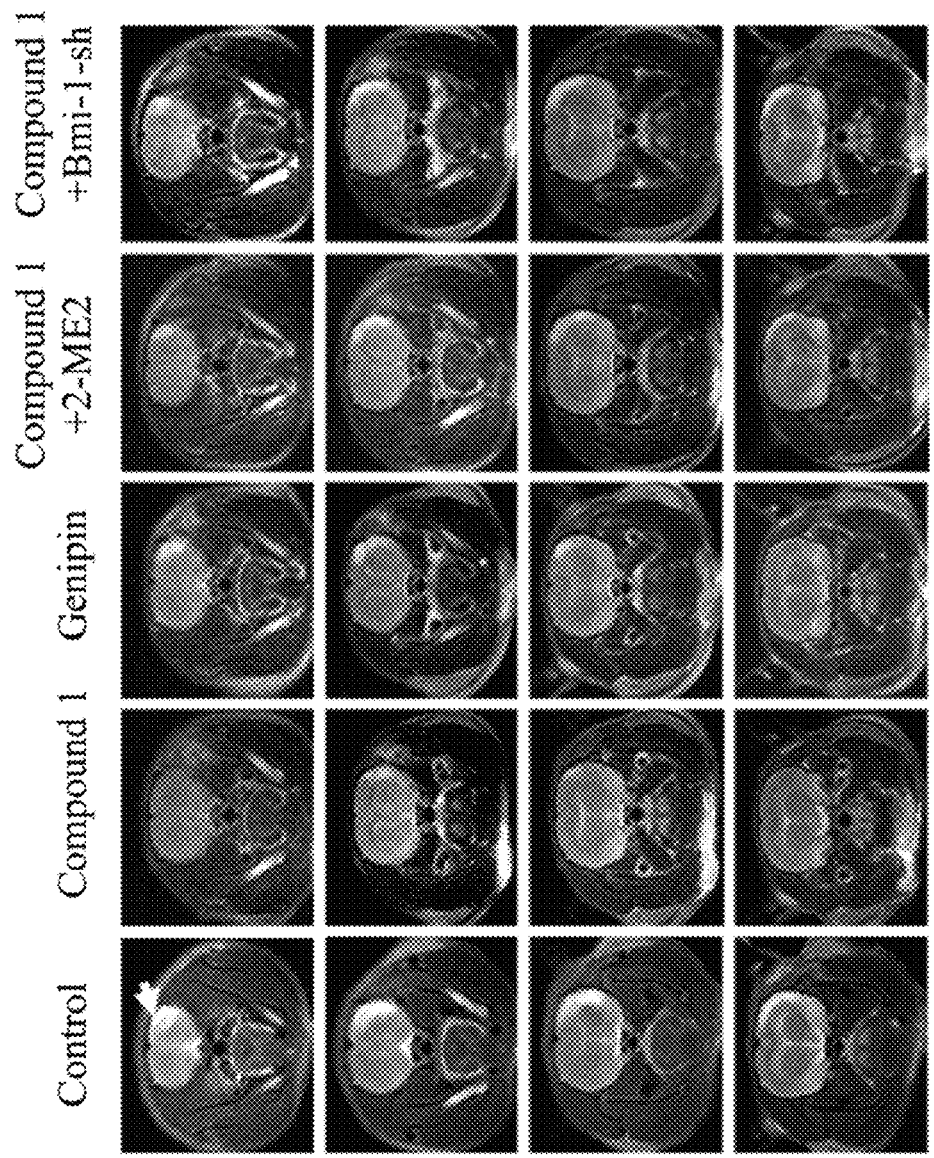
FIG. 18A shows analytical results of magnetic resonance imaging (MRI) in the ischemic rats treated with different conditions for 7 days.
Figure 18B:
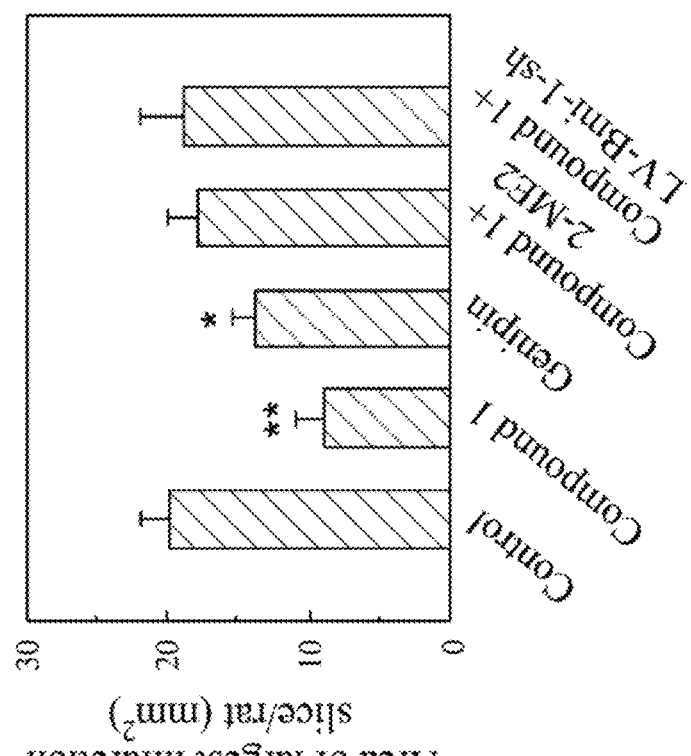
FIG. 18B is the quantitative diagram of the FIG. 18A.
Figure 18B:
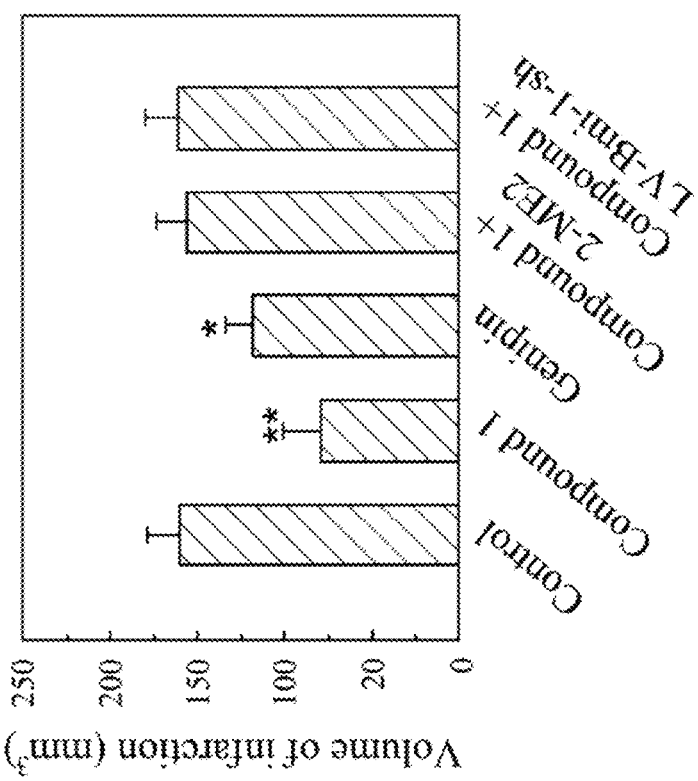

FIG. 18A shows the analytical results of the MRI in the ischemic rats treated with different conditions for 7 days. FIG. 18B is the quantitative diagram of the FIG. 18A. The results are represented by mean±SD values; n=8 per group, wherein * represents $p<0.05$ compared to the control group, and ** represents $p<0.01$ compared to the control group. In FIGS. 18A and 18B, the administration of the Compound 1 can significantly reduced the volume of the infarction and the area of the largest infarction in the brain of the ischemic rat. Although the administration of the genipin can reduced the volume of the infarction and the area of the largest infarction in the brain of the ischemic rat, the effect of the Compound 1 on the reduction of the infarction area in the ischemic rats is better than that of the genipin. However, the 2-ME2 treatment or the LV-Bmi-1-sh treatment abolishes the Compound-1-induced reduction of the volume of the infarction in the brains of the ischemic rats.

4.4 The Injection of the Compound 1 Promoted a Motor Improvement After the Cerebral Ischemia To evaluate the effect of the Compound 1 on the neurological recovery in the ischemic rats, neurological behavior of the ischemic rats before and after the cerebral ischemia are measured by three modalities of neurological deficits.

The ischemic rats are assigned into 4 groups, 3 test groups and 1 control group. The ischemic rats of the test groups are injected with 1 mg/kg of the Compound 1, 1 mg/kg of the Compound 1 and 100 mg/kg of 2-ME2, and 1 mg/kg of the Compound 1 and the LV-Bmi-1-sh, respectively. The ischemic rats of the control group are injected with the vehicle. Neurological behavioral assessments are performed at 5 day before the ischemia-reperfusion model, and at 1, 7, 14 and 28 days after the injection. The three modalities of neurological deficits measure body asymmetry, locomotor activity and grip strength of the ischemic rats.

i. A Body Swing Test

The body swing test is used to assess body asymmetry after MCA ligation. Initially, the ischemic rats are suspended by their tail 10 cm above the cage floor, and lateral body movements are recorded. Specifically, the frequency with which the initial head swing contra-lateral to the ischemic side is counted in twenty consecutive tests and is normalized to the baseline score.

Figure 19A:
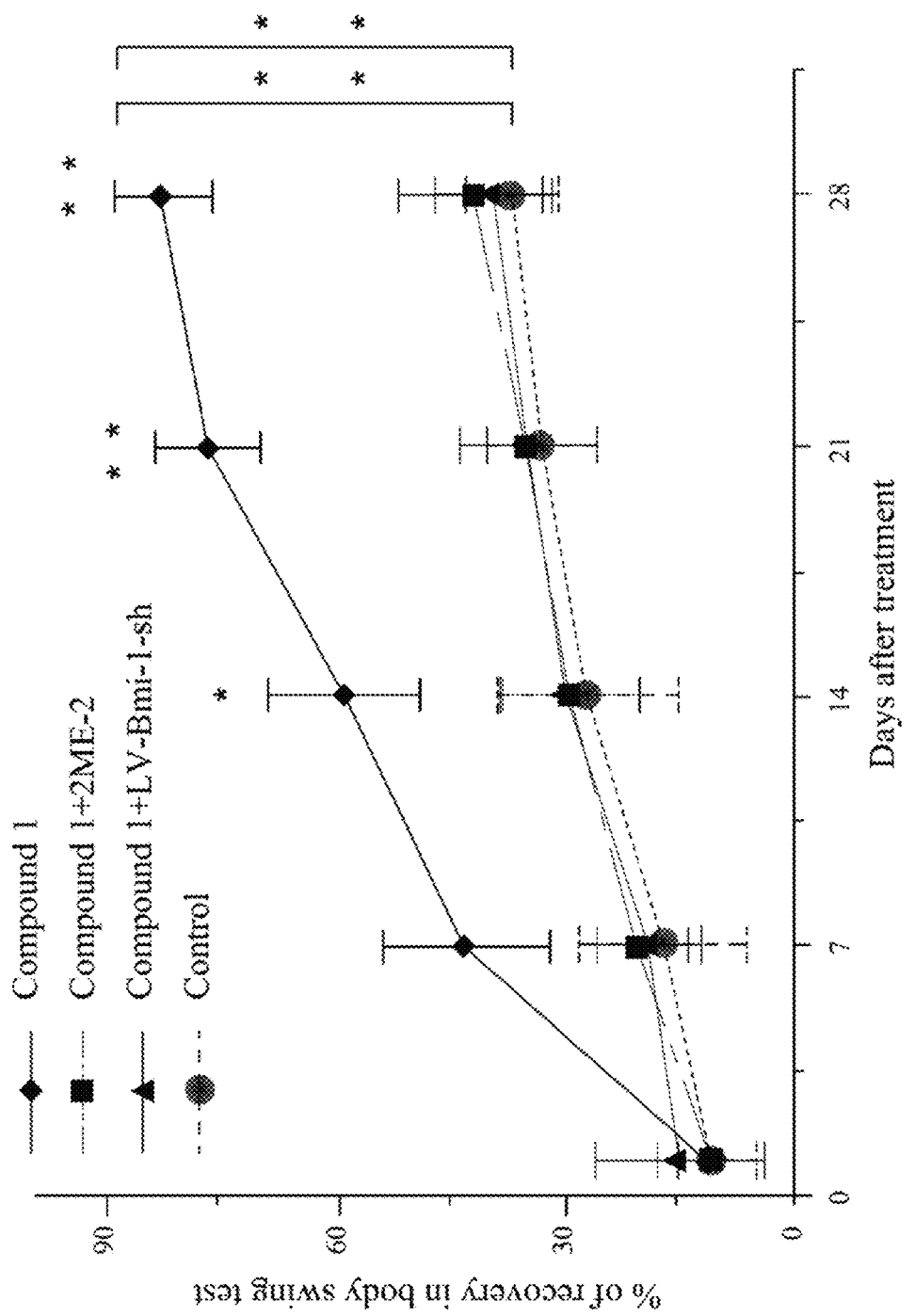
FIG. 19A shows analytical results of a body swing test of the ischemic rats.

FIG. 19A shows the analytical results of the body swing test of the ischemic rats. In FIG. 19A, the test group treated with the Compound 1 shows much more neurological recovery compared to the control group. However, the neurological recovery of the test group injected with the 2-ME2 for reducing the HIF-1α expressions or the test group injected with the LV-Bmi-1-sh for reducing the Bmi-1 expressions is similar to the control group. The results indicate that reduced HIF-1α expressions and reduced Bmi-1 expressions in the ischemic rats inhibit the treatment effect of the Compound 1.

ii. A Locomotor Activity Test

The locomotor activity test is measured for about 2 hours using VersaMax Animal Activity Monitoring System (Accuscan Instruments), which contains 16 horizontal infrared sensors and 8 vertical infrared sensors. The vertical sensors are situated 10 cm above the chamber floor and the locomotor activity is quantified by a number of a beam broken by the rat's movement in the chamber. Three vertical-movement parameters are measured: (i) vertical activity (ii) vertical time (iii) number of vertical movements by the manufacturer's instruction.

Figure 19B:
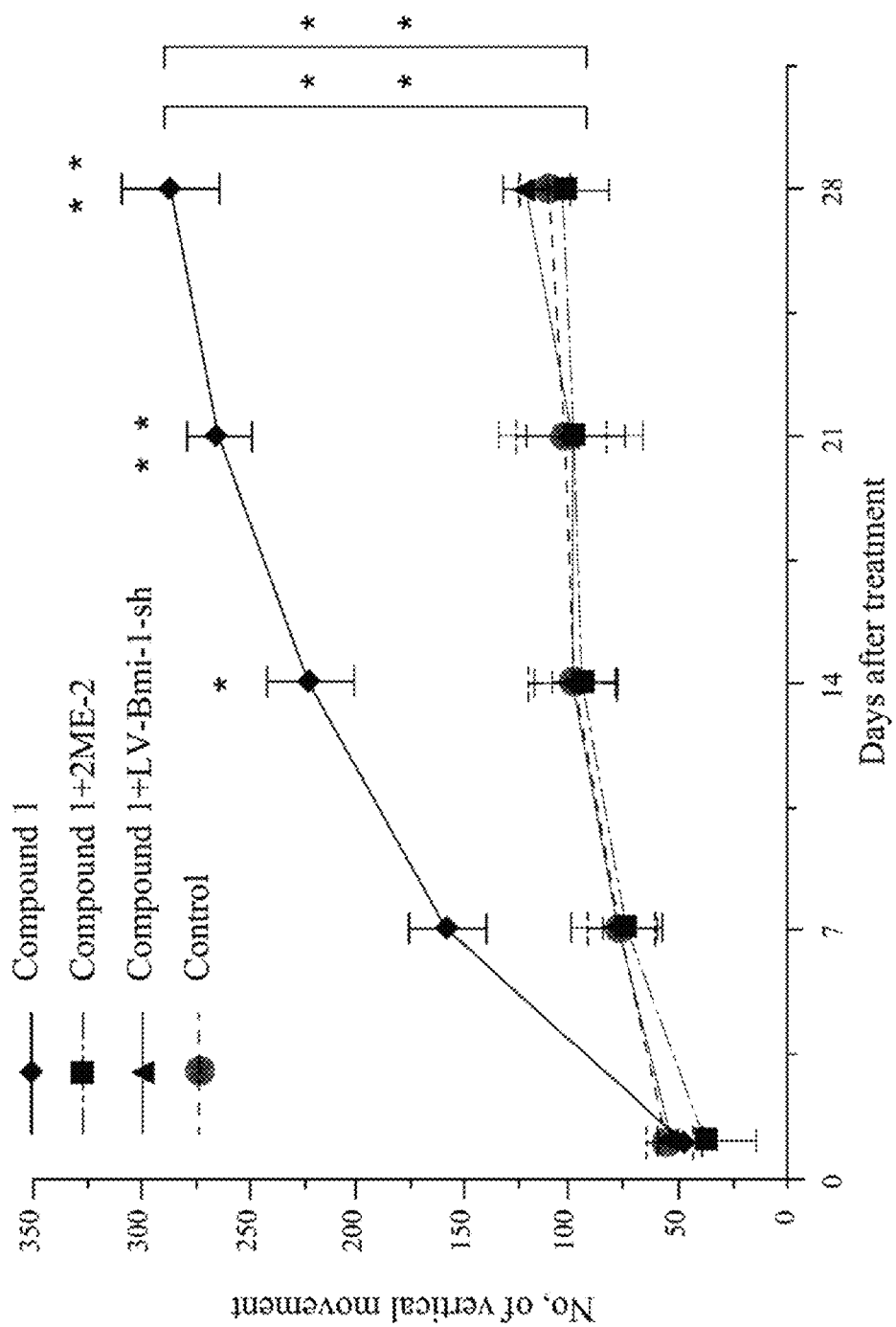
FIG. 19B shows analytical results of the number of the vertical movements in a locomotor activity test.
Figure 19C:
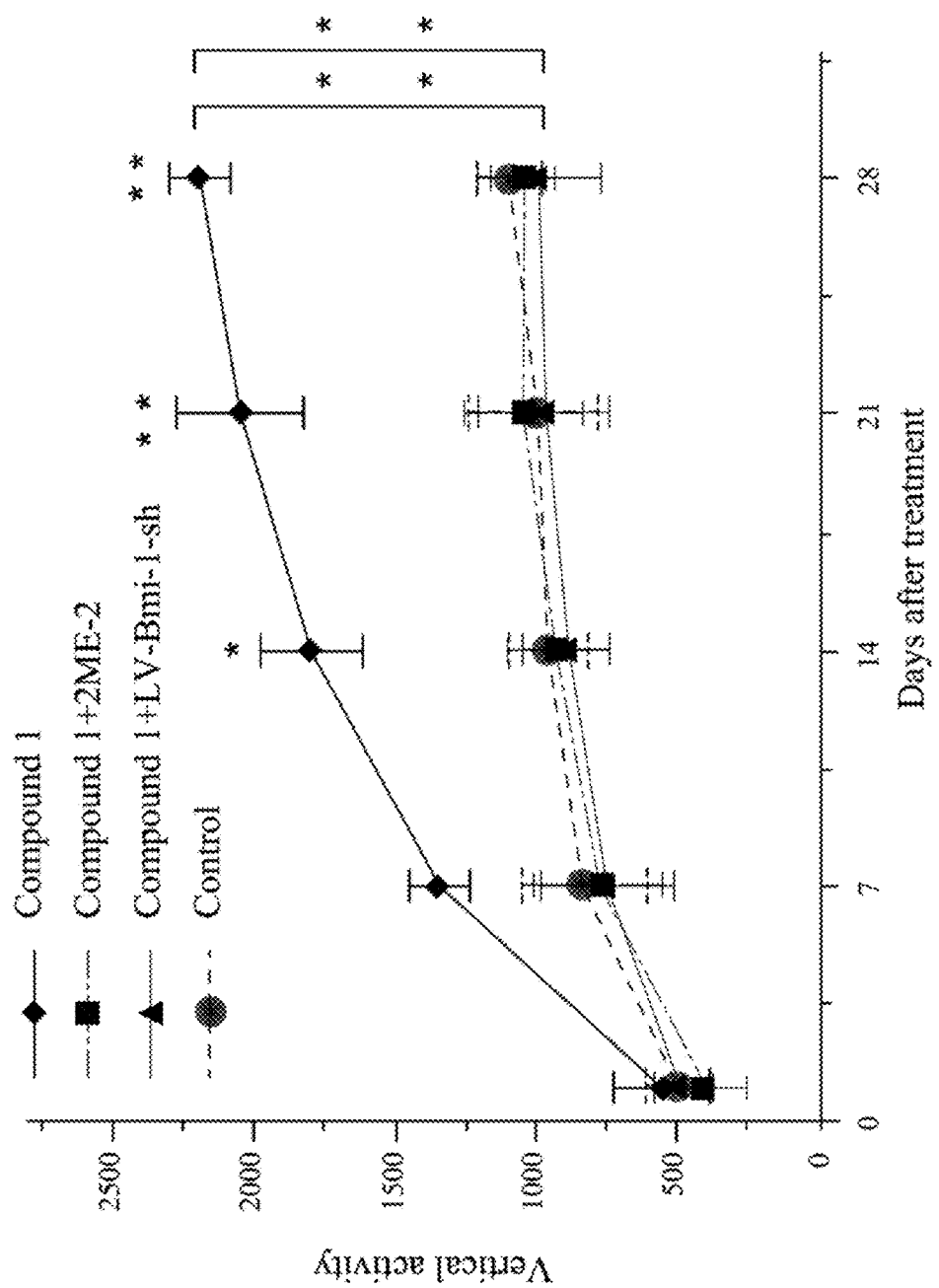
FIG. 19C shows analytical results of a vertical activity in the locomotor activity test.
Figure 19D:
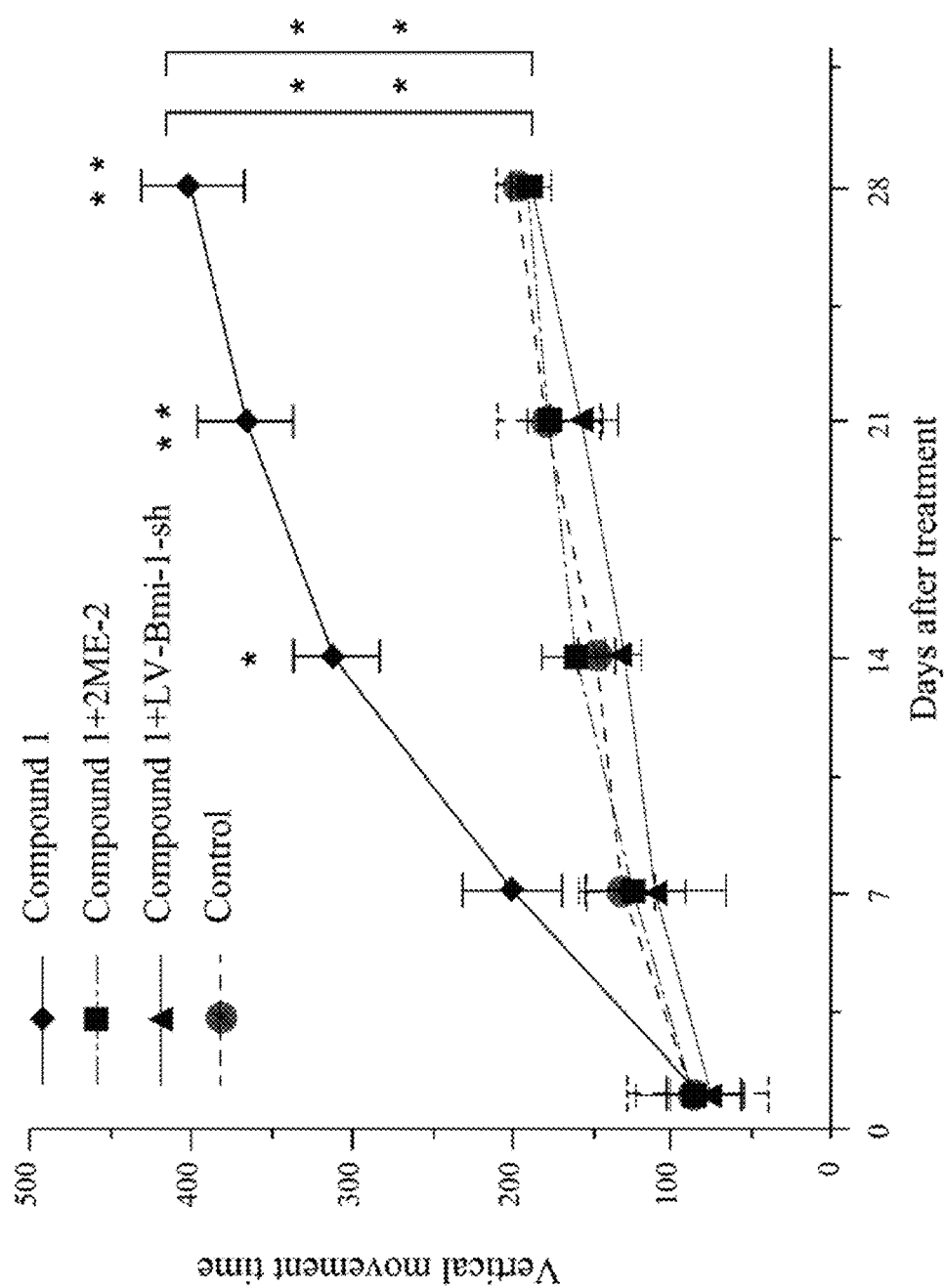
FIG. 19D shows analytical results of a vertical movement time in the locomotor activity test.

FIG. 19B shows the analytical results of the number of the vertical activity in the locomotor activity test. FIG. 19C shows analytical results of a vertical activity in the locomotor activity test. FIG. 19D shows analytical results of the vertical movement time in the locomotor activity test. In FIGS. 19B to 19C, the test group treated with the Compound 1 exhibit significant improvement in the locomotor activity compared to the control group. However, the locomotor activity of the test group injected with the 2-ME2 for reducing the HIF-1α expressions or the test group injected with the LV-Bmi-1-sh for reducing the Bmi-1 expressions is similar to the control group. The results indicate that reduced HIF-1α expressions and reduced Bmi-1 expressions in the ischemic rats inhibit the treatment effect of the Compound 1.

iii. A Grip Strength Test

The grip strength is analyzed using Grip Strength Meter (TSE-Systems). In brief, the grip strength of each forelimb of the ischemic rat is measured separately from the mean of 20 pulls, and the ratio of ipsilateral grip strength to contralateral grip strength is calculated. In addition, the ratio of grip strength post-cell-treatment and pre-cell-treatment is also calculated, and the changes are presented as a percentage of the pre-cell-treatment value.

Figure 20:
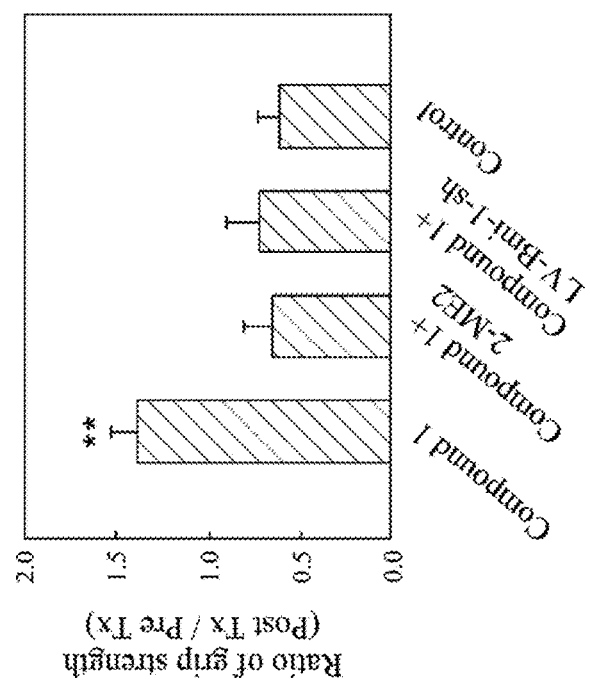
FIG. 20 shows analytical results of a grip strength test of the ischemic rats.

FIG. 20 shows the analytical results of the grip strength test of the ischemic rats. In FIG. 20, the test group treated with the Compound 1 has a much better grip strength ratio compared to the control group. However, the grip strength ratio of the test group injected with the 2-ME2 for reducing the HIF-1α expressions or the test group injected with the LV-Bmi-1-sh for reducing the Bmi-1 expressions is similar to the control group. The results indicate that reduced HIF-1α expressions and reduced Bmi-1 expressions in the ischemic rats inhibit the treatment effect of the Compound 1.

These results of three modalities of neurological deficits suggest that the administration of the Compound 1 can improve the neurological behaviors in the ischemic rats through the HIF-1α-Bmi-1 pathway.

To sum up, the present disclosure provides the bicyclic compound represented by Formula I or Formula II. The bicyclic compound of the present disclosure is a derivative of the genipin, an herbal drug, having a genipin backbone and chemically modified side chains. The bicyclic compound of the present disclosure improves defects of the genipin in chemical structure active unstability in aqueous environment, ready reaction with the amino ($-NH_2$) in aqueous solution or body tissue, and cross-linking between molecular structures. Therefore, the bicyclic compound of the present disclosure, having the genipin backbone and attaching specific structures of small molecules synthesized by chemical synthesis techniques to the genipin backbone, increases drug stability of the bicyclic compound of the present disclosure, improves drug efficacy and enhances affinity for the human body. Accordingly, the bicyclic compound of the present disclosure can reduce rejections and side effects of the new drugs on human body. The effect of the bicyclic compound of the present disclosure on the protection of neuronal cell death is better than the effect of the genipin. In addition, the bicyclic compound represented by Formula I or Formula II can reduce brain damage area to avoid the damage to brain tissue function. The bicyclic compound of the present disclosure can stimulate the proliferation and the self-renewal of the NSCs through the HIF-1α-Bmi-1 pathway, so that the bicyclic compound can induce neurogensis in the NSCs and movement to the damaged area in the brain of a stroke animal (particularly the ischemic stroke). Therefore, the bicyclic compound represented by Formula I or Formula II can be used as the drug or the pharmaceutical composition for treating the stroke.

The pharmaceuticals or pharmaceutical compositions, according to a conventional pharmaceutically process prepared, can includes pharmaceutically acceptable carriers which are compatible with the other ingredients of the formulation and is compatible with the living body. The term "pharmaceutically acceptable carrier" means a pharmaceutically acceptable material, composition or vehicle, such as liquid or solid filler, diluent, excipients, a solvent or an encapsulating material. It can be used in carrying or transporting the subject composition from the organ or part of the body to another organ or part of the body.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:
1. A bicyclic compound represented by:

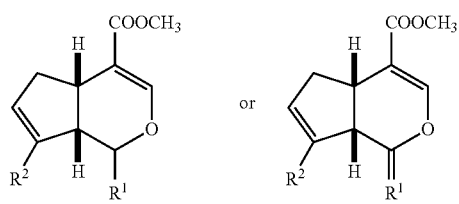

wherein —R$^1$ is —OH, —OCH$_2$CH$_3$, a substituent represented by Formula (i), a substituent represented by Formula (ii), a substituent represented by Formula (iii) or a substituent represented by Formula (iv);

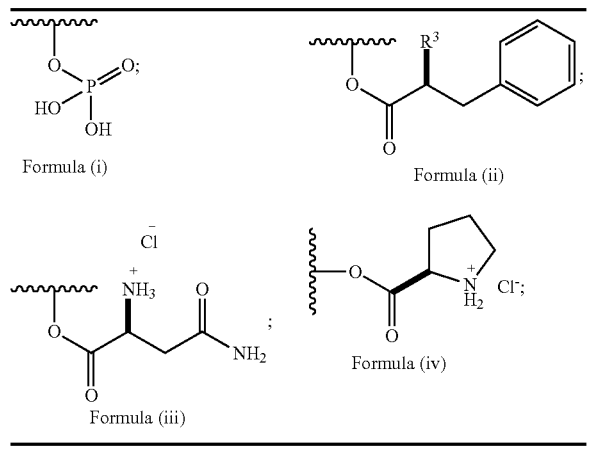

wherein in Formula (ii), R$^3$ is —NH$_2$, —NH$_3$$^+$Cl$^-$ or a substituent represented by Formula (vi):

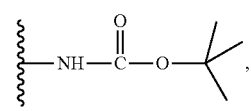

wherein R$^2$ is a substituent represented by Formula (vii):

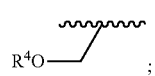

wherein R$^4$ is a substituent represented by Formula (viii), a substituent represented by Formula (ix) or a substituent represented by Formula (x):

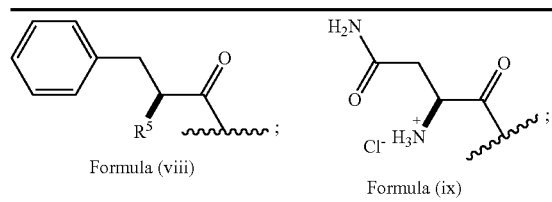

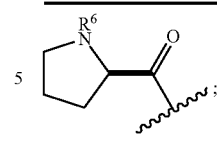

wherein in Formula (viii), R$^5$ is —NH$_2$, —NH$_3$$^+$Cl$^-$ or the substituent represented by Formula (vi);
and in Formula (x), R$^6$ is —H$_2$$^+$Cl$^-$ or the substituent represented by Formula (vi).

2. The bicyclic compound of claim 1 represented by a structural formula of the following table:

| Compound | Structural formula |
|---|---|
| 6 | |
| 7 | |
| 8 | |
| 9 | |
| 10 | |
| 11 | |
| 12 | |
| 14 | |
| 15 | |
| 16 | |
| 17 | |
3. The bicyclic compound of claim 1 represented by a structural formula 1:
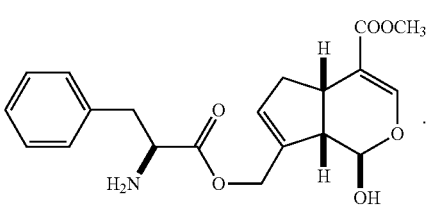 [SMILES: COC(=O)C1=CO[C@@H](O)[C@@H]2C(COC(=O)[C@@H](N)Cc3ccccc3)=CC[C@H]12]

4. The bicyclic compound of claim 1 represented by a structural formula 2:

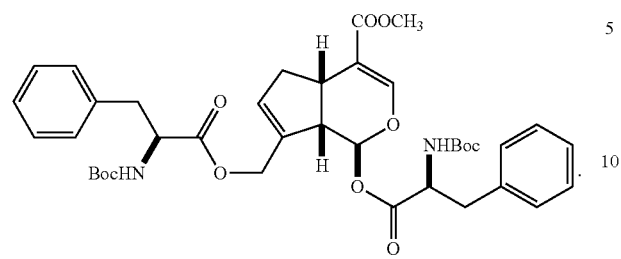

5. The bicyclic compound of claim 1 represented by a structural formula 3:

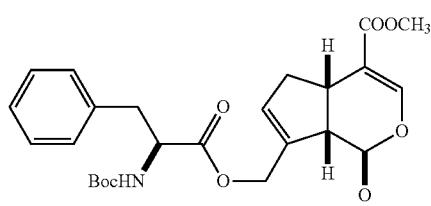

6. The bicyclic compound of claim 1 represented by a structural formula 4:

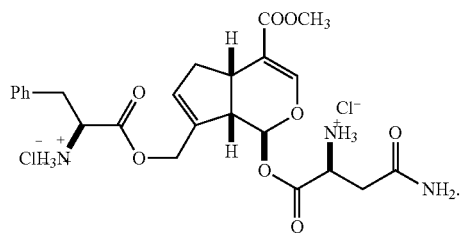

7. The bicyclic compound of claim 1 represented by a structural formula 5:

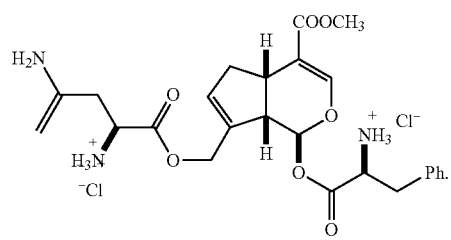

8. The bicyclic compound of claim 1 represented by a structural formula 6:

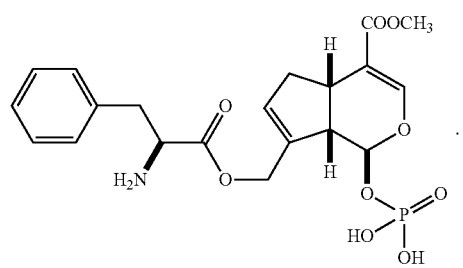 [SMILES: COC(=O)C1=CO[C@@H](OP(=O)(O)O)[C@@H]2C(COC(=O)[C@@H](N)Cc3ccccc3)=CC[C@H]12]

9. The bicyclic compound of claim 1 represented by a structural formula 7:

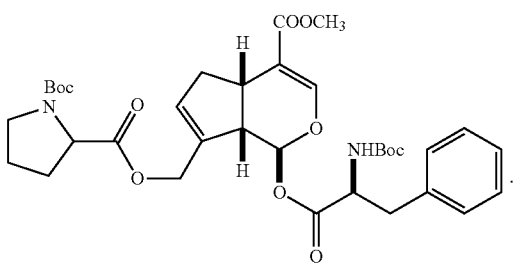 [SMILES: COC(=O)C1=CO[C@@H](OC(=O)[C@H](Cc2ccccc2)NC(=O)OC(C)(C)C)[C@@H]2C(COC(=O)C3CCCN3)=CC[C@H]12]

10. The bicyclic compound of claim 1 represented by a structural formula 8:

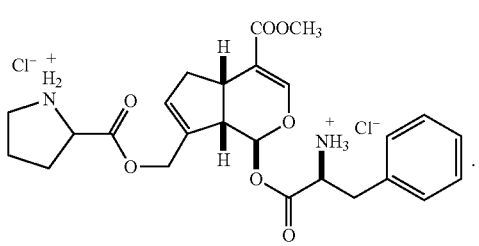

11. The bicyclic compound of claim 1 represented by a structural formula 9:

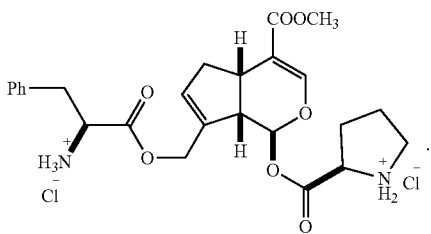

12. The bicyclic compound of claim 1 represented by a structural formula 10:

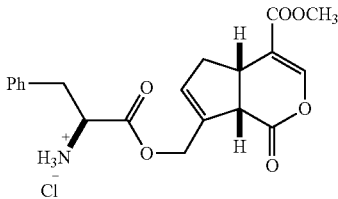

13. The bicyclic compound of claim 1 represented by a structural formula 11:

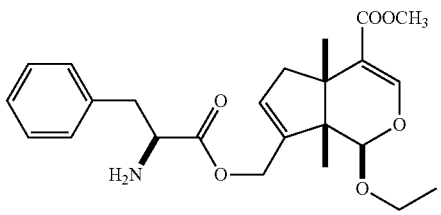

14. The bicyclic compound of claim 1 represented by a structural formula 12:

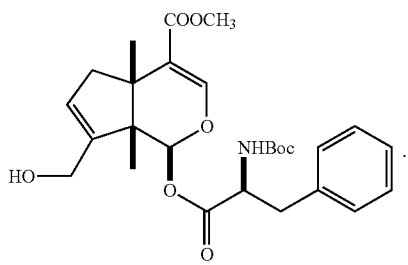 [SMILES: COC(=O)C1=CO[C@@H](OC(=O)[C@H](Cc2ccccc2)NC(=O)OC(C)(C)C)[C@]2(C)C(CO)=CC[C@]12C]

15. The bicyclic compound of claim 1 represented by a structural formula 14:

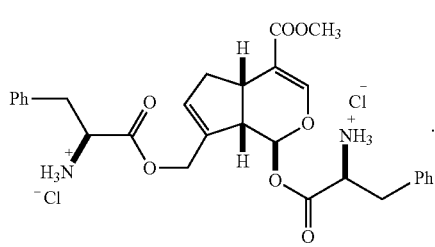

16. The bicyclic compound of claim 1 represented by a structural formula 15:

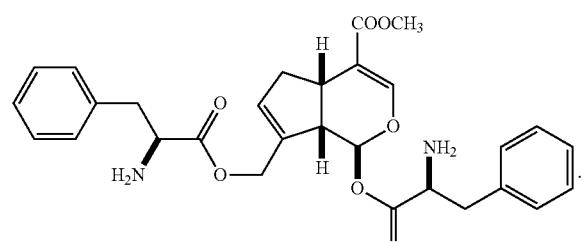

17. The bicyclic compound of claim 1 represented by a structural formula 16:

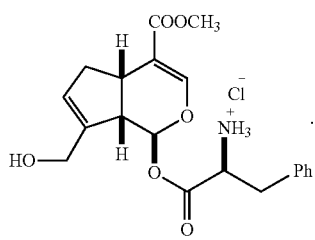

18. The bicyclic compound of claim 1 represented by a structural formula 17:

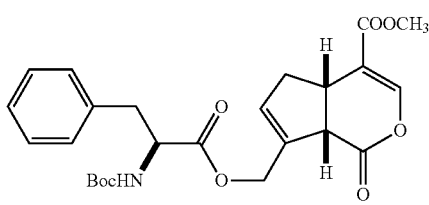

19. A pharmaceutical composition for treating a stroke comprising an effective amount of the bicyclic compound of claim 1 and a pharmaceutically acceptable carrier, wherein the effective amount is from 0.1 mg/kg to 10 mg/kg.

20. A method for treating an ischemic stroke comprising administering an effective amount of the bicyclic compound of claim 1 to a subject in need for a treatment of the stroke.

* * * * *